United States Patent
Tsimikas et al.

(10) Patent No.: US 12,351,649 B2
(45) Date of Patent: Jul. 8, 2025

(54) ANTIBODIES TO OXIDATION-SPECIFIC EPITOPES

(71) Applicant: The Regents of the University of California, Oakland, CA (US)

(72) Inventors: Sotirios Tsimikas, San Diego, CA (US); Joseph Witztum, San Diego, CA (US); Xuchu Que, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 620 days.

(21) Appl. No.: 17/500,794

(22) Filed: Oct. 13, 2021

(65) Prior Publication Data

US 2022/0135704 A1     May 5, 2022

Related U.S. Application Data

(63) Continuation of application No. 16/330,760, filed as application No. PCT/US2017/050566 on Sep. 7, 2017, now Pat. No. 11,168,148.

(60) Provisional application No. 62/384,694, filed on Sep. 7, 2016.

(51) Int. Cl.
| | | |
|---|---|---|
| *C07K 16/44* | (2006.01) | |
| *A61P 1/16* | (2006.01) | |
| *A61P 9/10* | (2006.01) | |
| *G01N 33/53* | (2006.01) | |

(52) U.S. Cl.
CPC .......... *C07K 16/44* (2013.01); *A61P 1/16* (2018.01); *A61P 9/10* (2018.01); *G01N 33/5308* (2013.01); *C07K 2317/21* (2013.01); *C07K 2317/24* (2013.01); *C07K 2317/565* (2013.01); *C07K 2317/622* (2013.01); *G01N 2800/085* (2013.01)

(58) Field of Classification Search
None
See application file for complete search history.

(56) References Cited

U.S. PATENT DOCUMENTS

| | | | |
|---|---|---|---|
| 6,814,951 B1 | 11/2004 | Thiele et al. | |
| 7,993,642 B2 * | 8/2011 | Tsunoda ................. | C07K 16/28 530/387.9 |
| 2012/0058906 A1 | 3/2012 | Smider et al. | |
| 2015/0056209 A1 | 2/2015 | Witztum et al. | |
| 2016/0145350 A1 | 5/2016 | Lonberg et al. | |

FOREIGN PATENT DOCUMENTS

| | | |
|---|---|---|
| WO | 2012/125582 A1 | 9/2012 |
| WO | 2013/158841 A1 | 10/2013 |

OTHER PUBLICATIONS

Hartvigsen et al. Arteriosclerosis, Thrombosis and Vascular Biology, (2009) vol. 29, No. 7, pp. e61. Abstract No. P275.*
https://www.ahajournals.org/data-sharing Jul. 7, 2024.*
Baharlou, Simin, International Preliminary Report on Patentability and Written Opinion, PCT/US17/50566, The International Bureau of WIPO, Mar. 21, 2019.
Carson et al., "Antibodies against malondialdehyde-acetalaldehyde adducts can help identify patients with abdominal aortic aneurysm," J. Vasc. Surg. 63:477-85, 2016.
De Pascalis et al., "Grafting of abbreviated complementarity determining regions containing specificity determining residues essential for ligand contact to engineer a less immunogenic humanized monoclonal antibody," J. of Immunol., 169:3076-3084, 2002.
Goel et al., "Plasticity within the Antigen-Combining Site May Manifest as Molecular Mimicry in teh Humoral Immune Response," J. Immunol. 173(12):7358-7367, 2004.
Kahn et al., "Adjustable Locks and Flexible Keys: Plasticity of Epitope-Paratope Interactions in Germline Antibodies," J. Immunol., 192:5398-5405, 2014.
MacCallum et al., "Antibody-antigen interactions: contact analysis and binding site topography," J. of Mol. Biol., 262:732-745, 1996.
Mariuzza et al., "The Structural Basis of Antigen-Antibody Recognition," Annu. Rev. Biophys. Biochem, 16:139-159, 1987.
Mikulis et al., "Enrichment of malondialdehyde acetalaldehyde antibody in the rheumatoid arthritis joint," Rheumatology, 56:1794-1803, 2017.
Poosarla et al., "Computational De Novo Design of Antibodies Binding to a Peptide With High Affinity," Biotech. Bioeng. 114(6):1331-1342, 2017.
Que, Xuchu et al., "IGHV1-69-Encoded Antibodies Expressed in Chronic Lymphocytic Leukemia React with Malondialdehyde-Acetaldehyde Adduct, an Immunodominant Oxidation-Specific Epitope", PLoS One, vol. 8, No. 6, Jun. 20, 2013, p. e65203.
Rudikoff S et al., "Single amino acid substitution altering antigen-binding specificity", Proceedings of the National Academy of Sciences, vol. 79, Mar. 1, 1982, pp. 1979-1983.
Klee, Barbara, Supplementary Search Report, European Patent Office, Application No. 17849567.7, Apr. 2, 2020.
Young, Lee W., International Search Report and Written Opinion, PCT/US17/50566, United States Patent and Trademark Office, Jan. 9, 2018.

* cited by examiner

*Primary Examiner* — Nora M Rooney
(74) *Attorney, Agent, or Firm* — Gavrilovich, Dodd & Lindsey LLP

(57) ABSTRACT

The disclosure provides for single chain variable fragments to MAA-oxidized specific epitopes (OSEs). The disclosure also provides single chain variable fragments that bind to MDA-OSEs or MAA-OSEs on oxidized phospholipids and methods of use thereof, including the production of transgenic animal models and the use of the fragments as therapeutic agents.

13 Claims, 31 Drawing Sheets

Specification includes a Sequence Listing.

```
LA25-Light Chain (Vλ2-14*01/J3*2)
  1   E  L  G  L  T  Q  P  P  S  V  S  G  S  P  G  Q  S  I  T  I
  1   GAGCTCGGCCTGACTCAGCCTCCCTCCGTGTCTGGGTCTCCTGGACAGTCGATCACCATC
 21   S  C  T  G  T  S  S  D  V  G  G  Y  N  Y  V  S  W  Y  Q  Q
 61   TCCTGCACTGGAACCAGCAGTGACGTTGGTGGTTATAACTATGTCTCCTGGTACCAACAG
 41   H  P  G  K  A  P  K  L  M  I  Y  E  V  S  N  R  P  S  G  V
121   CACCCAGGCAAAGCCCCCAAACTCATGATTTATGAGGTCAGTAATCGGCCCTCAGGGGTT
 61   S  N  R  F  S  G  S  K  P  G  N  T  A  S  L  T  I  S  G  L
181   TCTAATCGCTTCTCTGGCTCCAAGCCTGGCAACACGGCCTCCCTGACCATCTCTGGGCTC
 81   Q  A  E  D  E  A  D  Y  Y  C  S  S  Y  A  G  S  N  N  Y  W
241   CAGGCTGAGGATGAGGCTGATTATTACTGCAGCTCATATGCAGGCAGCAACAATTATTGG
101   V  F  G  G  G  T  K  L  T  V  L
301   GTGTTCGGCGGAGGGACCAAGCTGACCGTCCTA LA25 -Heavy Chain (VH3-33/D3-16/J2, 97% identify to germline)
  1   V  Q  R  Q  E  S  G  G  G  L  V  Q  P  G  S  S  L  R  L  S
  1   GTGCAGCGGCAGGAGTCGGGGGAGGCTTAGTTCAGCCTGGGGGGTCCCTGAGACTCTCC
 21   C  A  A  S  G  F  T  F  S  S  Y  G  M  H  W  V  R  Q  A  P
 61   TGTGCAGCCTCTGGATTCACCTTCAGTAGCTATGGCATGCACTGGGTCCGCCAGGCTCCA
 41   G  K  G  L  E  W  V  A  V  I  W  Y  D  G  S  N  K  Y  Y  A
121   GGCAAGGGGCTGGAGTGGGTGGCAGTTATATGGTATGATGGAAGTAATAAATACTATGCA
 61   D  S  V  K  G  R  F  T  I  S  R  D  N  S  K  N  T  L  Y  L
181   GACTCCGTGAAGGGCCGATTCACCATCTCCAGAGACAATTCCAAGAACACGCTGTATCTG
 81   Q  M  N  S  L  R  A  E  D  T  A  V  Y  Y  C  A  R  G  R  W
241   CAAATGAACAGCCTGAGAGCCGAGGACACGGCTGTGTATTACTGTGCAGAGGCCGCTGG
101   G  G  Y  F  D  L  W  G  R  G  T  L  V  T  V  S
301   GGGGGCTACTTCGATCTCTGGGGCCGTGGAACCCTGGTCACCGTCTCC
```

*FIG. 2*
*(Cont'd)*

```
>LA25 light chain
    1   A  G  S  L  R  G  Q  A  A  E  L  G  L  T  Q  P  P  S  V  S
   21   G  S  P  G  Q  S  I  T  I  S  C  T  G  T  S  S  D  V  G  G
   41   Y  N  Y  V  S  W  Y  Q  Q  H  P  G  K  A  P  K  L  M  I  Y
   61   E  V  S  N  R  P  S  G  V  S  N  R  F  S  G  S  K  P  G  N
   81   T  A  S  L  T  I  S  G  L  Q  A  E  D  E  A  D  Y  Y  C  S
  101   S  Y  A  G  S  N  N  Y  W  V  F  G  G  G  T  K  L  T  V  L
  121   G  Q  P  K  A  A  P  S  V  T  L  F  P  P  S  S  E  E  L  Q
  141   A  N  K  A  T  L  V  C  L  I  S  D  F  Y  P  G  A  V  T  V
  161   A  W  K  A  D  G  S  P  V  K  A  G  V  E  T  T  T  P  S  K
  181   Q  S  N  N  K  Y  A  A  S  S  Y  L  S  L  T  P  E  Q  W  K
  201   S  H  R  S  Y  S  C  Q  V  T  H  E  G  S  T  M  E  K  T  V
  221   A  P  T  E  C  S >LA25 Heavy Chain
    1   S  L  A  Q  V  Q  R  Q  E  S  G  G  G  L  V  Q  P  G  G  S
   21   L  R  L  S  C  A  A  S  G  F  T  F  S  S  Y  G  M  H  W  V
   41   R  Q  A  P  G  K  G  L  E  W  V  A  V  I  W  Y  D  G  S  N
   61   K  Y  Y  A  D  S  V  K  G  R  F  T  I  S  R  D  N  S  K  N
   81   T  L  Y  L  Q  M  N  S  L  R  A  E  D  T  A  V  Y  Y  C  A
  101   R  G  R  W  G  G  Y  F  D  L  W  G  R  G  T  L  V  T  V  S
  121   S  A  S  T  K  G  P  S  V  F  P  L  A  P  S  S  K  S  T  S
  141   G  G  T  A  A  L  G  C  L  V  K  D  Y  F  P  E  P  V  T  V
  161   S  W  N  S  G  A  L  T  S  G  V  H  T  F  P  A  V  L  Q  S
  181   S  G  L  Y  S  L  S  S  V  V  T  V  P  S  S  S  L  G  T  Q
  201   T  Y  I  C  N  V  N  H  K  P  S  N  T  K  V  D  K  K  V  E
  221   P  K  S  C  D  K  T  S  G  Q  A  G  Q  H  H  H  H  H  H  G
  241   A  Y  P  Y  D  V  P  D  Y  A  S
```

FIG. 3

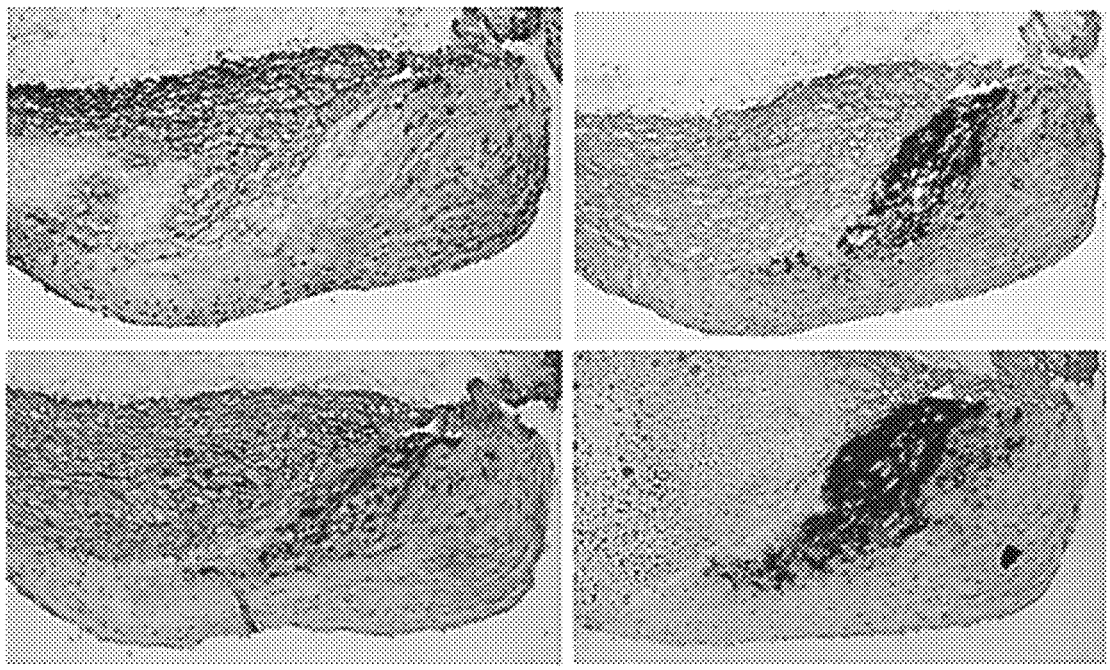

FIG. 4

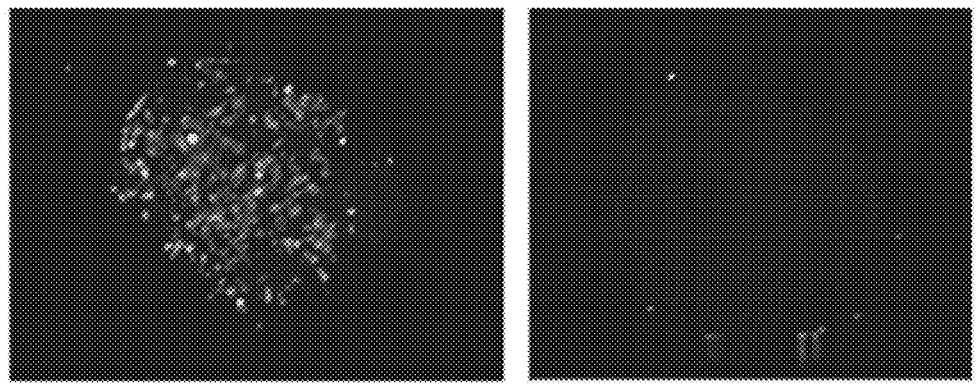
FIG. 7
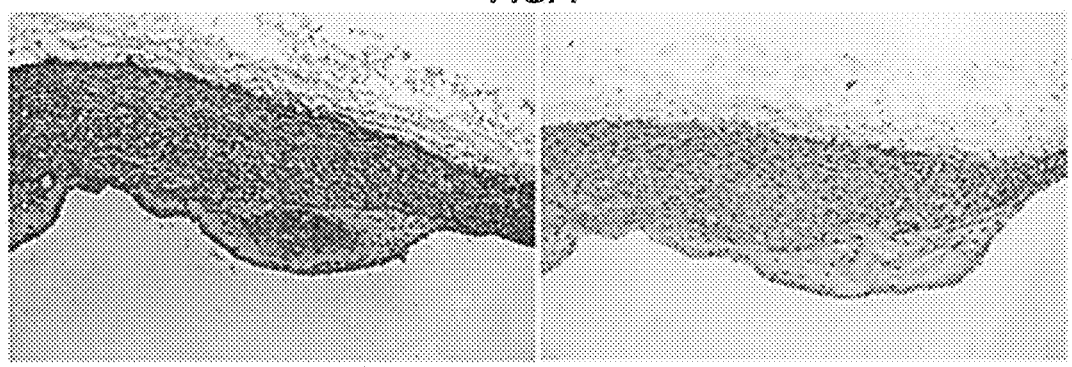
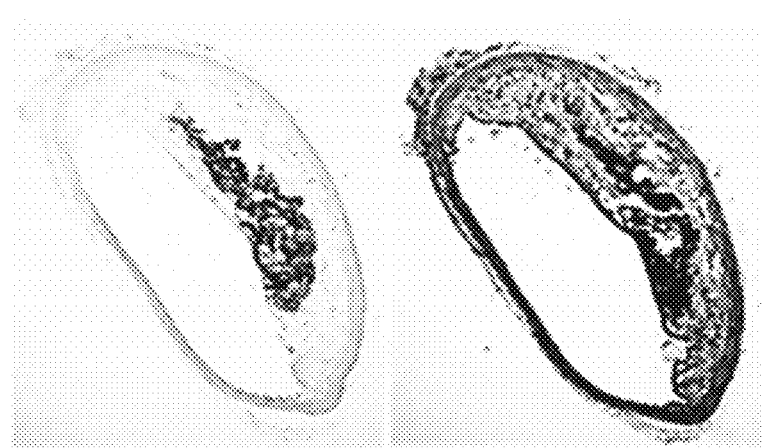
FIG. 8

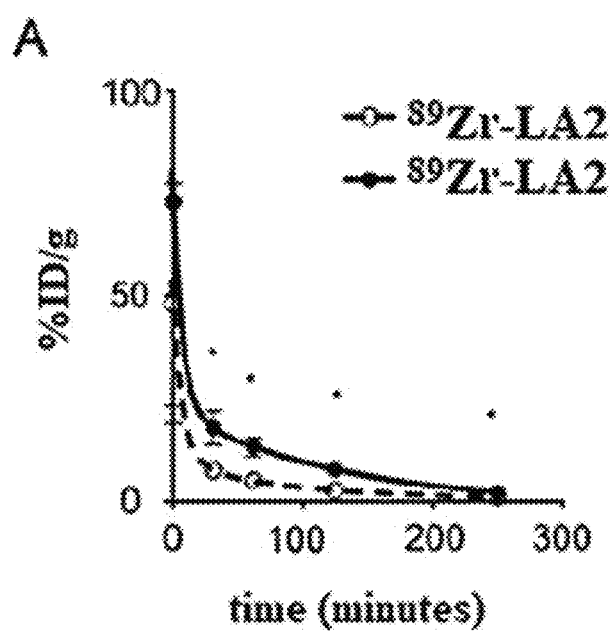
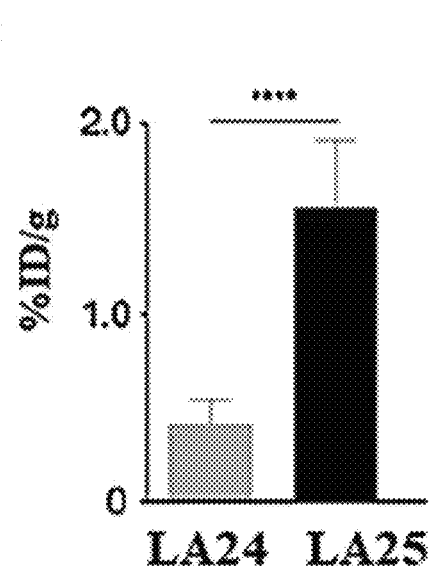
FIG. 22A
FIG. 22B
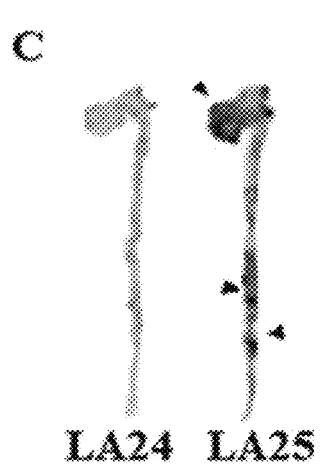
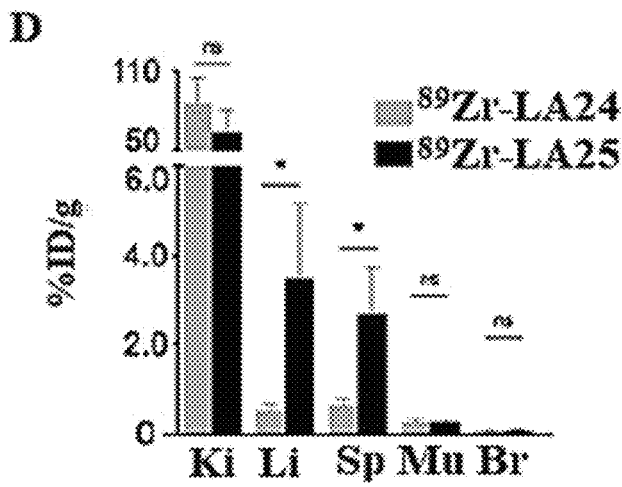
FIG. 22C
FIG. 22D

A
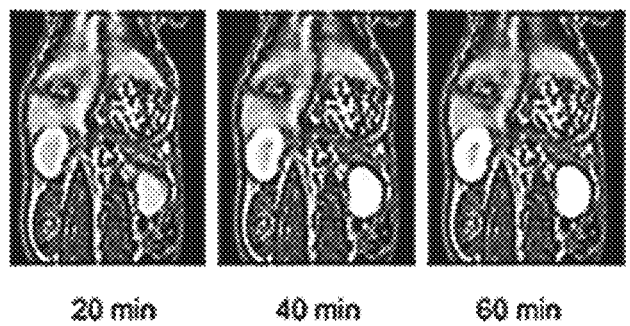
B
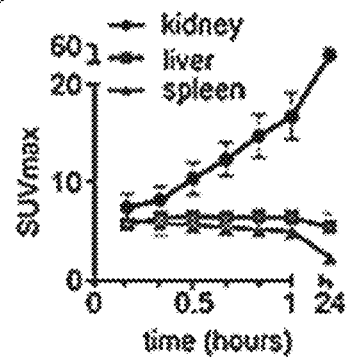
FIG. 23A
FIG. 23B
C
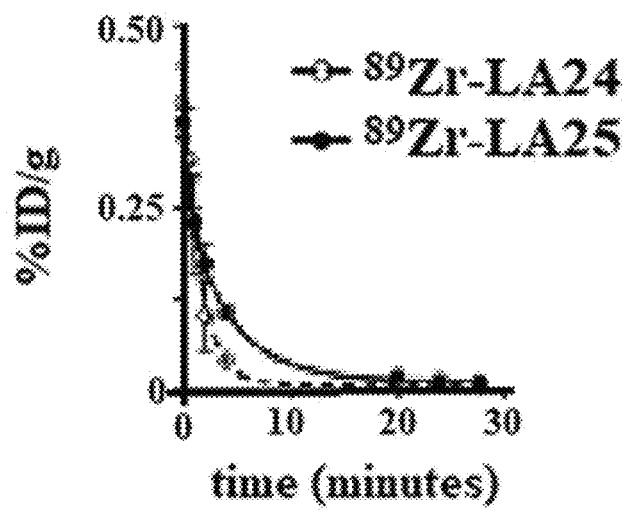
FIG. 23C

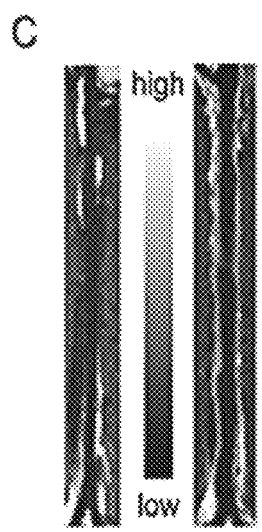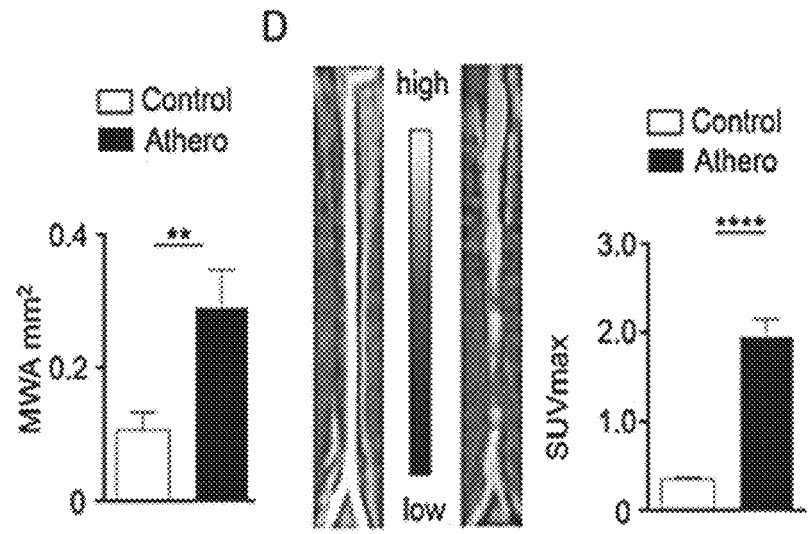
FIG. 24C
FIG. 24D
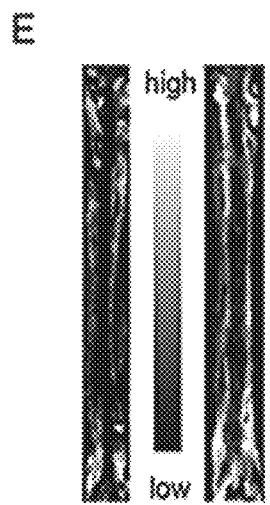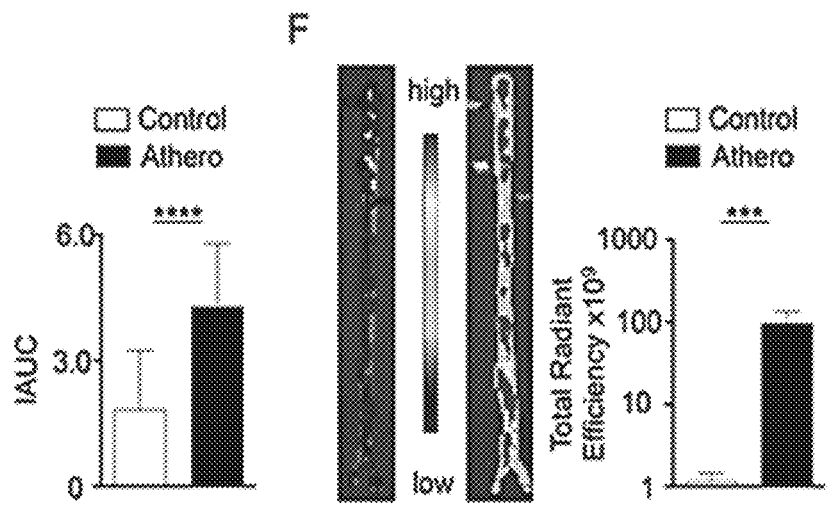
FIG. 24E
FIG. 24F

>LA25 light chain (IGVL 2-14*01, J3*2)(SEQ ID NO:1 and 2)
```
1   GAGCTCGGCCTGACTCAGCCTCCCTCCGTGTCTGGGTCTCCTGGACAGTCGATCACCATCTCCTGCACTGGAACC
    1   E   L   G   L   T   Q   P   P   S   V   S   G   S   P   G   Q   S   I   T   I   S   C   T   G   T
76  AGCAGTGACGTTGGTGGTTATAACTATGTCTCCTGGTACCAACAGCACCCAGGCAAAGCCCCCAAACTCATGATT
    26  S   S   D   V   G   G   Y   N   Y   V   S   W   Y   Q   Q   H   P   G   K   A   P   K   L   M   I
151 TATGAGGTCAGTAATCGGCCCTCAGGGGTTTCTAATCGCTTCTCTGGCTCCAAGTCTGGCAACACGGCCTCCCTG
    51  Y   E   V   S   N   R   P   S   G   V   S   N   R   F   S   G   S   K   F   G   N   T   A   S   L
226 ACCATCTCTGGGCTCCAGGCTGAGGATGAGGCTGATTATTACTGCAGCTCATATGCAGGCAGCAACAATTATTGG
    76  T   I   S   G   L   Q   A   E   D   E   A   D   Y   Y   C   S   S   Y   A   G   S   N   N   Y   W
301 GTGTTCGGCGGAGGGACCAAGCTGACCGTCCTA
    101 V   F   G   G   G   T   K   L   T   V   L
```

>LA25 Heavy Chain (IGHV 3-33/D3-16/J2)(SEQ ID NO:3 and 4)
```
1   CAGGTGCAGCGGCAGGAGTCGGGGGGAGGCTTAGTTCAGCCTGGGGGGTCCCTGAGACTCTCCTGTGCAGCCTCT
    1   Q   V   Q   R   Q   E   S   G   G   G   L   V   Q   P   G   G   S   L   R   L   S   C   A   A   S
76  GGATTCACCTTCAGTAGCTATGGCATGCACTGGGTCCGCCAGGCTCCAGGCAAGGGGCTGGAGTGGGTGGCAGTT
    26  G   F   T   F   S   S   Y   G   M   H   W   V   R   Q   A   P   G   K   G   L   E   W   V   A   V
151 ATATGGTATGATGGAAGTAATAAATACTATGCAGACTCCGTGAAGGGCCGATTCACCATCTCCAGAGACAATTCC
    51  I   W   Y   D   G   S   N   K   Y   Y   A   D   S   V   K   G   R   F   T   I   S   R   D   N   S
226 AAGAACACGCTGTATCTGCAAATGAACAGCCTGAGAGCCGAGGACACGGCTGTGTATTACTGTGCGAGAGGCCGC
    76  K   N   T   L   Y   L   Q   M   N   S   L   R   A   E   D   T   A   V   Y   Y   C   A   R   G   R
301 TGGGGGGGGTACTTCGATCTCTGGGGCCGTGGAACCCTGGTCACCGTCTCC
    101 W   G   G   Y   F   D   L   W   G   R   G   T   L   V   T   V   S
```

>KA2 light chain (IGKV2-28*01, IGKJ2*03 (SEQ ID NO:5 and 6)
```
1   GAGCTCGTGATGACTCAGTCTCCACTCTCCCTGCCCGTCACCCCTGGAGAGCCGGCCTCCATCTCCTGCAGGTCT
        E   L   V   M   T   Q   S   P   L   S   L   P   V   T   P   G   E   P   A   S   I   S   C   R   S
76  AGTCAGAGCCTCCTGCATAGTAATGGATACAACTATTTGGATTGGTACCTGCAGAAGCCAGGGCAGTCTCCACAG
        S   Q   S   L   L   H   S   N   G   Y   N   Y   L   D   W   Y   L   Q   K   P   G   Q   S   P   Q
151 CTCCTGATCTATTTGGGTTCTAATCGGGCCTCCGGGGTCCCTGACAGGTTCAGTGGCAGTGGATCAGGCACAGAT
        L   L   I   Y   L   G   S   N   R   A   S   G   V   P   D   R   F   S   G   S   G   S   G   T   D
226 TTTACACTGAAAATCAGCAGAGTGGAGGCTGAGGATGTTGGGGTTTATTACTGCATGCAAGCTCTACAAACTCAC
        F   T   L   K   I   S   R   V   E   A   E   D   V   G   V   Y   Y   C   M   Q   A   L   Q   T   H
301 AGTTTTGGCCAGGGGACCAAGCTGGAGATCAAAC
        S   F   G   Q   G   T   K   L   E   I   K
```

>KA2 heavy chain (IGHV3-74*01, D6-13*01, J4*02) (SEQ ID NO:7 and 8)
```
1   CAGGTGCAGCGGCAGGAGTCGGGGGGAGGCTTAGTTCAGCCTGGGGGGTCCCTGAGACTCTCCTGTGCAGCCTCT
        Q   V   Q   R   Q   E   S   G   G   G   L   V   Q   P   G   G   S   L   R   L   S   C   A   A   S
76  GGATTCACCTTCAGTAGCTACTGGATGCACTGGGTCCGCCAAGCTCCAGGGAAGGGGCTGGTGTGGGTCTCACGT
        G   F   T   F   S   S   Y   W   M   H   W   V   R   Q   A   P   G   K   G   L   V   W   V   S   R
151 ATTAATAGTGATGGGAGTAGCACAAGCTACGCGGACTCCGTGAAGGGCCGATTCACCATCTCCAGAGACAACGCC
        I   N   S   D   G   S   S   T   S   Y   A   D   S   V   K   G   R   F   T   I   S   R   D   N   A
226 AAGAACACGCTGTATCTGCAAATGAACAGTCTGAGAGCCGAGGACACGGCTGTGTATTACTGTGCAAGAGATTAT
        K   N   T   L   Y   L   Q   M   N   S   L   R   A   E   D   T   A   V   Y   Y   C   A   R   D   Y
301 AGCAGCAGCTGGTACTTTGACTACTGGGGCCAGGGAACCCTGG
        S   S   S   W   Y   F   D   Y   W   G   Q   G   T   L
```

*FIG. 27*

>LR04 Light Chain (Musmus IGKV2-137*01, IGKJ2*01) (SEQ ID NO:9 and 10)
```
  1 GACATTTTGATGACACAGGCTGCACCCTCTGTACCTGTCACTCCTGGAGAGTCAGTATCCATCTCCTGCAGGTCT
      D  I  L  M  T  Q  A  A  P  S  V  P  V  T  P  G  E  S  V  S  I  S  C  R  S
 76 AGTAAGAGTCTCCTGCATAGTAATGGAACACTTACTTGTATTGGTTCCTGCAGAGGCCAGGCCAGTCTCCTCAG
      S  K  S  L  L  H  S  N  G  N  T  Y  L  Y  W  F  L  Q  R  P  G  Q  S  P  Q
151 CTCCTGATATATCGGATGTCCAACCTTGCCTCAGGAGTCCCAGACAGGTTCAGTGGCAGTGGGTCAGGAACTGCT
      L  L  I  Y  R  M  S  N  L  A  S  G  V  P  D  R  F  S  G  S  G  S  G  T  A
226 TTCACACTGAGAATCAGTAGAGTGGAGGCTGAGGATGTGGGTGTTTATTACTGTATGCAACATCTAGAATATCCT
      F  T  L  R  I  S  R  V  E  A  E  D  V  G  V  Y  Y  C  M  Q  H  L  E  Y  P
301 TACACGTTCGGAGGGGGGACCAAGCTGGAAA
      Y  T  F  G  G  G  T  K  L  E
```

>LR04 Heavy Chain (Musmus IGHV9-3*01, D4-1*01, J3*01) (SEQ ID NO:11 and 12)
```
  1 CAGATCCAGTTGGTGCAGTCTGGACCTGAGCTGAAGAAGCCTGGAGAGACAGTCAAGATCTCCTGCAAGGCTTCT
      Q  I  Q  L  V  Q  S  G  P  E  L  K  K  P  G  E  T  V  K  I  S  C  K  A  S
 76 GGGTATACCTTCACAACCTATGGAATGAGCTGGGTGAAACAGGCTCCAGGAAAGGGTTTAAAGTGGATGGGCTGG
      G  Y  T  F  T  T  Y  G  M  S  W  V  K  Q  A  P  G  K  G  L  K  W  M  G  W
151 ATAAACACCTACTCTGGAGTGCCAACATATGCTGATGACTTCAAGGGACGGTTTGCCTTCTCTTTGGAAACCTCT
      I  N  T  Y  S  G  V  P  T  Y  A  D  D  F  K  G  R  F  A  F  S  L  E  T  S
226 GCCAGCACTGCCTATTTGCAGATCAACAACCTCAAAAATGAGGACACGGCTACATATTTCTGTGCAAAACTGGGG
      A  S  T  A  Y  L  Q  I  N  N  L  K  N  E  D  T  A  T  Y  F  C  A  K  L  G
301 TTTGCTTACTGGGGCCAAGGGACTCTGGTCACTGTCTCTGCAGAGAGTCAGTCCTTCCC
      F  A  Y  W  G  Q  G  T  L  V  T  V  S  A
```

>LA24 Light chain (IGKV3-20*01, IGKJ4*01) (SEQ ID NO:21 and 22)
```
  1 GAGCTCACACTCACGCAGTCTCCAGGCACCCTGTCTTTGTCTCCAGGGGAAAGAGCCACCCTCTCCTGCAGGGCC
      E  L  T  L  T  Q  S  P  G  T  L  S  L  S  P  G  E  R  A  T  L  S  C  R  A
 76 AGTCAGAGTGTTAGCAGCAGCTACTTAGCCTGGTACCAGCAGAAACCTGGCCAGGCTCCCAGGCTCCTCATCTAT
      S  Q  S  V  S  S  S  Y  L  A  W  Y  Q  Q  K  P  G  Q  A  P  R  L  L  I  Y
151 GGTGCATCCAGCAGGGCCACTGGCATCCCAGACAGGTTCAGTGGCAGTGGGTCTGGGACAGATTTCACTCTCACC
      G  A  S  R  A  T  G  I  P  D  R  F  S  G  S  G  S  G  T  D  F  T  L  T
226 ATCAGCAGCCTGCAGCCTGAAGATGTTGCAACTTATTACTGTCAAAAGTATAACAGTGCCCCGCTCACTTTCGGC
      I  S  S  L  Q  P  E  D  V  A  T  Y  Y  C  Q  K  Y  N  S  A  P  L  T  F  G
301 GGAGGGACCAAGGTGGAGATCAAACG
      G  G  T  K  V  E  I  K
```

>LA24 Heavy chain (IGHV3-30*02, IGHD2-8*02, J4*02) (SEQ ID NO:23 and 24)
```
  1 GAGGTGCAGCTGTTGGAGTCTGGGGGAGGCTTGGTAAAGCCTGGGGGGTCCCTTAGACTCTCCTGTGCAGCGTCT
      E  V  Q  L  L  E  S  G  G  G  L  V  K  P  G  G  S  L  R  L  S  C  A  A  S
 76 GGATTCACCTTCGGTAGCTATGGCATGCACTGGGTCCGCCAGGCTCCAGGCAAGGGGCTGGAGTGGGTGGCATTT
      G  F  T  F  G  S  Y  G  M  H  W  V  R  Q  A  P  G  K  G  L  E  W  V  A  F
151 ATACGGTATGATGGAAGTAATAAATACTATGCAGACTCCGTGAAGGGCCGATTCACCATCTCCAGAGACAATTCC
      I  R  Y  D  G  S  N  K  Y  Y  A  D  S  V  K  G  R  F  T  I  S  R  D  N  S
226 AAGAACACGCTGTATCTGCAAATGAACAGCCTGAGAGCTGAGGACACGGCTGTGTATTACTGTGCGAAACCCGGG
      K  N  T  L  Y  L  Q  M  N  S  L  R  A  E  D  T  A  V  Y  Y  C  A  K  P  G
301 CCCTGGGGCTGGTACTTTGACTACTGGGGCCAGGGAACCCTGGTCACCGTCTCCTCAG
      P  W  G  W  Y  F  D  Y  W  G  Q  G  T  L  V  T  V  S  S
```

*FIG. 27*
*(Cont'd)*

```
>ML7 light-chain (Homsap IGLV1-47*02, IGLJ3*02) (SEQ ID NO:13 and 14)
  1 GAGCTCGTGCTGACTCAGCCACCCTCAGCGTCTGGGACCCCCGGGCAGAGGGTCACCATCTCTTGTTCTGGAAGC
     E  L  V  L  T  Q  P  P  S  A  S  G  T  P  G  Q  R  V  T  I  S  C  S  G  S
 76 AGCTCCAACATCGGAAGTAATTATGTATATTGGTACCAGCAGCTCCCAGGAACGGCCCCCAAACTCCTCATCTAT
     S  S  N  I  G  S  N  Y  V  Y  W  Y  Q  Q  L  P  G  T  A  P  K  L  L  I  Y
151 AGTAATAATCAGCGGCCCTCAGGGGTCCCTGACCGATTCTCTGGCTCCAAGCCTGGCACCTCAGCCTCCCTGGCC
     S  N  N  Q  R  P  S  G  V  P  D  R  F  S  G  S  K  P  G  T  S  A  S  L  A
226 ATCAGTGGGCTCCAGTCTGACGATGAGGCTGATTATTATTGTGCAGCGTGGGACGTCAGCCTGAGACAATGGCTG
     I  S  G  L  Q  S  D  D  E  A  D  Y  Y  C  A  A  W  D  V  S  L  R  Q  W  L
301 TTCGGCGGAGGGACCAAGCTGACCGTCCTAG
     F  G  G  G  T  K  L  T  V  L >ML7 heavy-chain (IGHV3-33*01, IGHD3-16*02, IGHJ6*02) (SEQ ID NO:15 and 16)
  1 CAGGTGGAGCGGGTGCAGTCTGGGGGAGGCGTGGTCCAGCCTGGGAGGTCCCTGAGACTCTCCTGTGCAGCGTCT
     Q  V  E  R  V  Q  S  G  G  G  V  V  Q  P  G  R  S  L  R  L  S  C  A  A  S
 76 GGATTCACCTTCAGTAGCTATGGCATGCACTGGGTCCGCCAGGCTCCAGGCAAGGGGCTGGAGTGGGTGGCAGTT
     G  F  T  F  S  S  Y  G  M  H  W  V  R  Q  A  P  G  K  G  L  E  W  V  A  V
151 ATATGGTATGATGGAAGTAATAAATACTATGCAGACTCCGTGAAGGGCCGATTCACCATCTCCAGAGACAATTCC
     I  W  Y  D  G  S  N  K  Y  Y  A  D  S  V  K  G  R  F  T  I  S  R  D  N  S
226 AAGAACACGCTGTATCTGCAAATGAACAGCCTGAGAGCCGAGGACACGGCTGTGTATTACTGTGCGAGAGGTTCA
     K  N  T  L  Y  L  Q  M  N  S  L  R  A  E  D  T  A  V  Y  Y  C  A  R  G  S
301 TTATCCGGGCTGGACGTCTGGGGCCAAGGAACCCTGGTCACCGTCTCCT
     L  S  G  L  D  V  W  G  Q  G  T  L  V  T  V  S >MK17 light-chain (IGKV1-9*01, IGKJ3*01) (SEQ ID NO:17 and 18)
  1 GAGCTCGTGTTGACGCAGTCTCCATCCTTCCTGTCTGCATCTATAGGAGACAGAGTCACCATCACTTGCCGGGCC
     E  L  V  L  T  Q  S  P  S  F  L  S  A  S  I  G  D  R  V  T  I  T  C  R  A
 76 AGTCAGGGCATTGGCAATTATTTAGCCTGGTATCAGCAAAAACCAGGGAAAGCCCCTAAGCTCCTGATTTATGCT
     S  Q  G  I  G  N  Y  L  A  W  Y  Q  Q  K  P  G  K  A  P  K  L  L  I  Y  A
151 GCATCCACTTTGCAAAGTGGGGTCCCATCAAGGTTCAGCGGCAGTAAATCTGGGACAGAGTTCACTCTCACAATC
     A  S  T  L  Q  S  G  V  P  S  R  F  S  G  S  K  S  G  T  E  F  T  L  T  I
226 AGCAGCCTTCAGCCTGAGGATTCTGCAACTTATTACTGTCAGCAACTTAACGGTTACCCTCTCACTTTCGGCCCT
     S  S  L  Q  P  E  D  S  A  T  Y  Y  C  Q  Q  L  N  G  Y  P  L  T  F  G  P
301 GGGACCAAAGTGGATATCAAAC
     G  T  K  V  D  I  K >MK17 Heavy-chain (Homsap IGHV3-33*01, IGHD6-19*01, IGHJ4*03) (SEQ ID NO:19 and
20)
  1 CAGCTGGTGCAGTCTGGGGGAGGCGTGGTCCAGCCTGGGCGGTCCCTGAGACTCTCCTGTGCAGCGTCTGGATTC
     Q  L  V  Q  S  G  G  G  V  V  Q  P  G  R  S  L  R  L  S  C  A  A  S  G  F
 76 ACCTTCAGTAGCTATGGCATGCACTGGGTCCGCCAGGCTCCAGGCAAGGGGCTGGAGTGGGTGGCAGTTATATGG
     T  F  S  S  Y  G  M  H  W  V  R  Q  A  P  G  K  G  L  E  W  V  A  V  I  W
151 TATGATGGAAGTAATAAATACTATGCAGACTCCGTGAAGGGCCGATTCACCATCTCCAGAGACAATTCCAAGAAC
     Y  D  G  S  N  K  Y  Y  A  D  S  V  K  G  R  F  T  I  S  R  D  N  S  K  N
226 ACGCTGTATCTGCAAATGAACAGCCTGAGAGCCGAGGACACGGCTGTGTATTACTGTGCGAGAGATCGGGGTTAT
     T  L  Y  L  Q  M  N  S  L  R  A  E  D  T  A  V  Y  Y  C  A  R  D  R  G  Y
301 CCGTGGCTACGATCCCGGGGCGGTATGGACGTCTGGGGCCAAGGCACCCTGGTCACCGTCTCCCCTG
     P  W  L  R  S  R  G  G  M  D  V  W  G  Q  G  T  L  V  T  V  S
```

*FIG. 27*
*(Cont'd)*

ANTIBODIES TO OXIDATION-SPECIFIC EPITOPES

CROSS REFERENCE TO RELATED APPLICATIONS

This application is a continuation of U.S. application Ser. No. 16/330,760, filed Mar. 5, 2019, which application is a U.S. National Phase Application filed under 35 U.S.C. § 371 and claims priority to International Application No. PCT/US2017/050566, filed Sep. 7, 2017, which application claims priority under 35 U.S.C. § 119 from Provisional Application Ser. No. 62/384,694, filed Sep. 7, 2016, the disclosures of which are incorporated herein by reference.

GOVERNMENT LICENSE RIGHTS

This invention was made with Government support under HL119828, HL056989, and HL088093 awarded by the National Institutes of Health. The government has certain rights in the invention.

INCORPORATION BY REFERENCE OF SEQUENCE LISTING

Accompanying this filing is a Sequence Listing entitled "Sequence ST25.txt", created on Sep. 7, 2017 and having 40.4 kB of data, machine formatted on IBM-PC, MS-Windows operating system. The sequence listing is hereby incorporated by reference in its entirety for all purposes.

TECHNICAL FIELD

This invention provides monoclonal antibodies directed to oxidation-specific epitopes, specifically malondialdehyde-acetaldehyde (MAA) that is involved in a variety of diseases, including cardiovascular disease, liver disease and neurological diseases. The disclosure also provides methods of using the antibody as a molecular imaging agent and therapeutic ("biotheranostic") in these disease states. The invention also provides a method of "passive vaccination" to prevent diseases, i.e. atherosclerosis or liver disease.

BACKGROUND

Atherosclerosis is the underlying cause of cardiovascular diseases. The main pathways that drive this disease are the accumulation of lipids and concomitant immune cell infiltration in the vessel wall. Oxidized low-density lipoprotein (oxLDL) plays a major role in initiation and progression of so-called atherosclerotic plaques. To detect (sub)clinical atherosclerosis, a variety of imaging techniques are available. However, current clinical techniques do not characterize the atherosclerotic plaque, but merely predict the risk of future events based on the level of stenosis. In the past decade, molecular imaging has provided new insights in pathophysiology at a cellular and molecular level. It therefore allows phenotyping and identifying features of plaque progression that precede a possible rupture.

SUMMARY

The disclosure provides an isolated antibody or antibody fragment that recognizes and binds to an MAA oxidized specific epitope (OSE)(MAA-OSE), wherein the antibody or antibody fragment comprises a variable heavy chain ($V_H$) domain and/or a variable light chain ($V_L$) domain, and wherein, (a) the $V_H$ domain comprises a sequence selected from the group consisting of (i) at least one CDR selected from the group consisting of SEQ ID NO:25, 26 and 27; (ii) at least one CDR selected from the group consisting of 28, 29 and 30; (iii) at least one CDR selected from the group consisting of SEQ ID NO:31, 32 and 33; (iv) at least one CDR selected from the group consisting of SEQ ID NO:34, 35 and 36; and (v) at least one CDR selected from the group consisting of SEQ ID NO:37, 38 and 39; and/or (b) the $V_L$ domain comprises a sequence selected from the group consisting of: (i) at least one CDR selected from the group consisting of SEQ ID NO:40, 41 and 42; (ii) at least one CDR selected from the group consisting of SEQ ID NO:43, 44 and 45; (iii) at least one CDR selected from the group consisting of SEQ ID NO:46, 47 and 48; (iv) at least one CDR selected from the group consisting of SEQ ID NO:49, 50 and 52; and (v) at least one CDR selected from the group consisting of SEQ ID NO:52, 53 and 54. In one embodiment, the antibody or antibody fragment comprises a variable heavy chain sequence of (a) selected from the group consisting of (1) SEQ ID NO:4; (2) SEQ ID NO:8; (3) SEQ ID NO:12; (4) SEQ ID NO:16; and (5) SEQ ID NO:20. In another or further embodiment, the antibody comprises a variable light chain sequence of (b) selected from the group consisting of: (6) SEQ ID NO:2; (7) SEQ ID NO:6; (8) SEQ ID NO:10; (9) SEQ ID NO:14; and (10) SEQ ID NO:18. In another embodiment, the antibody comprise a variable light chain sequence that is at least 98% identical to SEQ ID NO:2 and a variable heavy chain sequence that is at least 98% identical to SEQ ID NO:4. In yet another embodiment, the antibody comprise a variable light chain sequence that is at least 98% identical to SEQ ID NO:6 and a variable heavy chain sequence that is at least 98% identical to SEQ ID NO:8. In still another embodiment, the antibody comprise a variable light chain sequence that is at least 98% identical to SEQ ID NO:14 and a variable heavy chain that is at least 98% identical to SEQ ID NO:16. In another embodiment, the antibody comprise a variable light chain that is at least 98% identical to SEQ ID NO:18 and a variable heavy chain that is at least 98% identical to SEQ ID NO:20. In yet another embodiment, the antibody is non-human and comprises a variable light chain that is at least 98% identical to SEQ ID NO:10 and a variable heavy chain that is at least 98% identical to SEQ ID NO:12. In a further embodiment, the antibody is humanized. In still another embodiment of any of the foregoing, the heavy and light chain domains are linked to an Fc region.

The disclosure also provides a single chain variable fragment ("scFv") that recognizes an MAA-OSE and comprises (A) a $V_H$ domain containing a sequence selected from the group consisting of (i) at least one CDR selected from the group consisting of SEQ ID NO:25, 26 and 27; (ii) at least one CDR selected from the group consisting of 28, 29 and 30; (iii) at least one CDR selected from the group consisting of SEQ ID NO:31, 32 and 33; (iv) at least one CDR selected from the group consisting of SEQ ID NO:34, 35 and 36; and (v) at least one CDR selected from the group consisting of SEQ ID NO:37, 38 and 39; and (B) a $V_L$ domain containing a sequence selected from the group consisting of (i) at least one CDR selected from the group consisting of SEQ ID NO:40, 41 and 42; (ii) at least one CDR selected from the group consisting of SEQ ID NO:43, 44 and 45; (iii) at least one CDR selected from the group consisting of SEQ ID NO:46, 47 and 48; (iv) at least one CDR selected from the group consisting of SEQ ID NO:49, 50 and 52; and (v) at least one CDR selected from the group consisting of SEQ ID NO:52, 53 and 54. In one embodiment, the scFv is soluble under physiological conditions.

The disclosure also provides an antibody comprising a variable light chain and variable heavy chain sequence selected from the group consisting of (a) SEQ ID NO:2 and 4; (b) SEQ ID NO:6 and 8; (c) SEQ ID NO:10 and 12; (d) SEQ ID NO:14 and 16; and (e) SEQ ID NO:18 and 20. In one embodiment, the variable light chain comprises SEQ ID NO:10 and the variable heavy chain comprise SEQ ID No:12 and an Fc region is human or humanized. In another embodiment, the variable light chain and variable heavy chain are human or humanized and the Fc region is non-human.

The disclosure also provides a polynucleotide that encodes an antibody, antibody fragment, variable light chain, variable heavy chain or scFv as described herein.

The disclosure also provides a vector comprising a polynucleotide sequence selected from the group consisting of (a) SEQ ID NO:1 and/or 3; (b) SEQ ID NO:5 and/or 7; (c) SEQ ID NO:9 and/or 11; (d) SEQ ID NO:13 and/or 15; and (e) SEQ ID NO:17 and/or 19.

The disclosure also provides host cells transfected or transformed with a vector or polynucleotide of the disclosure.

The disclosure also provide a transgenic animal, comprising a polynucleotide of the disclosure wherein the non-human transgenic organism expresses an antibody or antibody fragment of the disclosure.

The disclosure also provides a method of treating a subject with an MAA-related disease or disorder comprising administering an antibody or antibody fragment as described herein to the subject, wherein the antibody or antibody fragment binds to and inhibits the biological effect caused by an MAA adduct. In one embodiment, the antibody or antibody fragment comprises a sequence selected from the group consisting of: (a) SEQ ID NO:2 and 4; (b) SEQ ID NO:6 and 8; (c) SEQ ID NO:14 and 16; and (d) SEQ ID NO:18 and 20. In one embodiment, the subject is a human. In another embodiment, the subject has a cardiovascular disease or disorder, a fatty liver disease or disorder, an acute lung injury disease or disorder, or rheumatoid arthritis disease or disorder.

The disclosure also provides a method of treating oxidative stress in a subject comprising administering an antibody or antibody fragment of the disclosure to the subject, wherein the antibody binds to and inhibits the biological effect caused by an MAA adduct.

The disclosure also provides a method of diagnosing an inflammatory fatty liver disease or disorder comprising contacting a subject with an antibody or antibody fragment of as described herein, wherein the antibody is labeled with a detectable label and imaging the subject to determine the amount or presence of the antibody in the liver of the subject. In one embodiment, if the amount of the antibody in the liver exceeds a normal control amount then the subject has an inflammatory liver disease. In another embodiment, the inflammatory liver disease is non-alcoholic fatty liver disease. In a further embodiment, the inflammatory liver disease is non-alcoholic steatohepatitis (NASH).

The disclosure also provides a method of diagnosing a MAA-related disease or disorder in a subject comprising obtaining a sample from the subject and contacting the sample with an antibody or antibody fragment as described herein and measuring the amount of antibody or antibody fragments bound to and MAA adduct in the sample compared to a normal control sample, wherein an amount of antibody or antibody fragment bound to an MAA adduct in the sample is greater than the control, the subject has an MAA-related disease or disorder.

The disclosure also provides a method of treating or inhibiting atherogenesis in a subject, the method comprising administering to the subject an antibody or antibody fragment of the disclosure, wherein the antibody binds to an inhibits that uptake and/or inflammatory response caused by an MAA adduct. In one embodiment, the MAA adduct is associated with a molecule in an atherosclerotic plaque.

The disclosure also provides a method for treating atherosclerosis and/or fatty liver disease in a subject, the method comprising administering to the subject antibodies or antibody fragments as described herein that specifically bind an MAA adduct, wherein the antibodies or antibody fragments are in a pharmaceutically acceptable carrier.

The disclosure also provides a method of inhibiting the progression of non-alcoholic fatty liver disease to non-alcoholic steatoheptatis (NASH) comprising administering to a subject in need of such treatment and antibody or antibody fragment of the disclosure in an amount to reduce inflammation and to improve biomarkers of liver function.

DESCRIPTION OF DRAWINGS

FIGS. 2-3 shows sequences (nucleic acid and polypeptide) for the variable light and heavy domains of an antibodies of the disclosure. FIG. 2 provides SEQ ID Nos:1-4, while FIG. 3 provides SEQ ID Nos: 55-56.

FIG. 4 presents the staining of atherosclerotic lesions from rabbit aorta with selected Fab clones ($2^{nd}$ antibody: anti-HA-biotin conjugate clone HA-7).

FIG. 7 presents deconvolution microscopy of LA25 binding to apoptotic Jurkat cells but not normal cells. (Blue—nuclei stained with Hoechst dye; Green—FITC-labeled anti-Fab).

FIG. 8 displays staining of atherosclerotic lesions from WHHL rabbits and high fat cholesterol diets fed LDLR−/− mice with LA25 and LA24 control Fab.

FIG. 22A-D shows pharmacokinetics of $^{89}$Zr-LA25; radioactivity half-life of 29 min, and 13 min for $^{89}$Zr-LA24 (A). Gamma counting and autoradiography of $^{89}$Zr-LA24 (grey) and $^{89}$Zr-LA25 (black) in Apoe$^{-/-}$ mouse aortas (B, C). Biodistribution in Apoe$^{-/-}$ mice (D). **** P<0.0001, * P<0.01.

FIG. 23A-E shows representative coronal fused PET/MR images at 20, 40 and 60 min post injection (p.i.) of $^{89}$Zr-LA25 (top) and $^{89}$Zr-LA24 (bottom) (A). Radioactivity quantification in major organs in atherosclerotic rabbits based on PET/MR imaging (10-60 min), and 24 hours p.i. (B). SUV=Standardized uptake values. Pharmacokinetics in atherosclerotic rabbits for $^{89}$Zr-LA24 and $^{89}$Zr-LA25, with half-lives of 1.1 and 2.2 hours, respectively (C). Ex vivo radioactivity concentration (D) and autoradiography (E) for $^{89}$Zr-LA24 and $^{89}$Zr-LA25 in aortas from rabbits with atherosclerosis 28 hours post injection.

FIG. 24A-F shows representative coronal aortic fused PET/MR imaging 24 hours post injection. (A), autoradiography and gamma counting (whole aortas) 28 hours p.i. of $^{89}$Zr-LA25 (B). MR T2-weighted imaging (C), $^{18}$F-FDG PET/MRI (D), DCE-MRI after (E) and Cy5-rHDL near infrared fluorescence imaging (F). All in healthy control (white) and atherosclerotic rabbit abdominal aortas (black). ****P<0.0001.

FIG. 27 shows sequences of the VH and VL antibody domains of the various anti-MAA antibodies of the disclosure. The bolded/underlined sequence correspond to CDR domains.

DETAILED DESCRIPTION

Figure 1A:
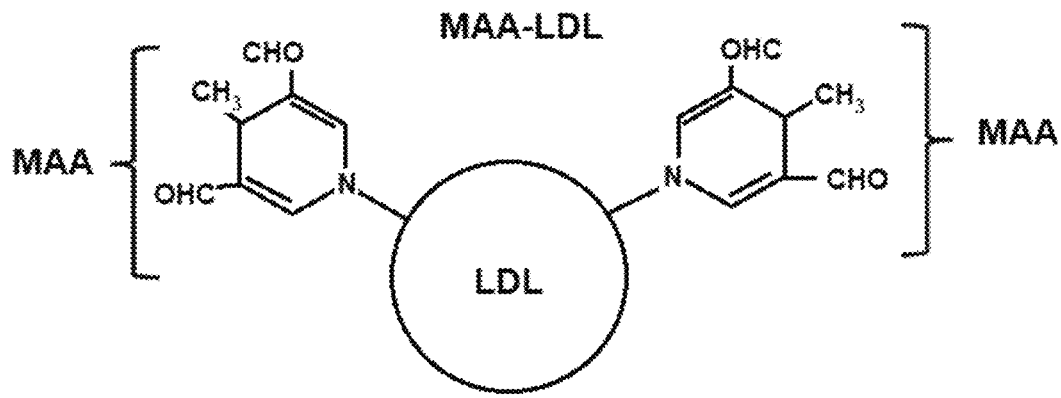
FIG. 1A-D shows pictorial depiction of MAA-LDL (A). The configuration of soluble LA25 Fab antibody fragment. The LA25 lambda light-chain and heavy-chain with a hexa-histidine and the influenza hemagglutinin (HA) epitope tag for detection and purification were expressed under the direction of lacZ promoter for phage display or Fab production in $E.\ coli$. Proteolysis of the ompA and pelB signal peptides in the periplasm generated the native amino terminus of Fab and facilitated the joining of heavy- and light-chains together by disulfide bonds as bio-active soluble Fab (B). Binding of LA25 to a variety of oxidation-specific epitopes, while LA24 does not (C). Competition assays for the specificity of LA25 binding to MAA-LDL. LA25 was incubated in the absence and presence of increasing amounts of indicated competitors, and the extent of binding to plated MAA was determined. Data are expressed as a ratio of binding in the presence of competitor (B) divided by absence of competitor ($B_0$) (D).

As used herein and in the appended claims, the singular forms "a," "an," and "the" include plural referents unless the context clearly dictates otherwise. Thus, for example, reference to a "single-chain variable fragment" or "scFv" includes a plurality of single-chain variable fragments and reference to "oxidized phospholipid" includes reference to one or more oxidized phospholipids and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Atherosclerosis is a chronic and multifocal inflammatory disease of medium and large arteries and the major underlying cause of cardiovascular disease (CVD). Despite a decline in mortality in the Western World, the prevalence of CVD has not declined and remains the leading global cause of death. Progression of atherosclerosis is driven by the accumulation, modification and oxidation of circulating lipids, which drives the influx of immune cells in the vessel wall, leading to chronic inflammation and the development of advanced atherosclerotic plaques. Progressing plaques are prone to develop erosion and/or rupture, resulting in the release of thrombotic material into the circulation that may lead to luminal occlusion and acute cardiovascular events, e.g., myocardial infarction, stroke and acute ischemic injury. A large subset of such plaques continue to grow until they cause myocardial ischemia, leading to angina pectoris.

Clinical practice relies on detecting ischemia of obstructive lesions to diagnose risk, leaving features like plaque burden and outward remodeling underappreciated. There is a need for accurate imaging methods to assess the extent of disease burden and to identify high-risk lesions, including those with superficial plaque erosion. Moreover, an emerging paradigm focusing on superficial plaque erosion, departing from the classical thrombotic rupture has been suggested.

Non-alcoholic fatty liver disease (NAFLD) is the most common cause of chronic liver disease in children. NAFLD includes a range of disease states from benign steatosis to non-alcoholic steatohepatitis (NASH). The disease may cause cirrhosis with the need for liver transplantation as well as other problems such as metabolic and cardiovascular disease. Although the pathogenesis of NAFLD is still unclear it is likely that insulin resistance, increased oxidative stress and lipid peroxidation play roles. Levels of intracellular glutathione, which protects against oxidative stress, are low in NAFLD. Two distinct histological forms of NASH have been described.

Type 1 NASH occurs in adults and some children and is characterized by steatosis, lobular inflammation, ballooning degeneration and perisinusoidal fibrosis. Type 2 NASH is found most commonly in children and is characterized by steatosis, portal inflammation, and portal fibrosis. Schwimmer et al. (Hepatgology, 42(3):641-649, 2005; incorporated herein by reference) described various criteria and biomarkers used to differentiate NASH Type 1 from NASH Type 2. In particular, Schwimmer et al. discloses that subjects with NASH Type 1 had higher AST, ALT and triglyceride levels compared to patients with NASH Type 2. However, the strongest factor demonstrating a difference in the two types of NASH are best found upon histological examination. As stated above, Type 1 NASH demonstrates a prevalent lobular inflammation in the liver in contrast with a prevalent portal inflammation in Type 2 NASH. Thus, the disclosure contemplates that one of the key differentiating factors that can be used in the methods disclosed herein is identifying, by histological examination, the presence of Type 1 vs. Type 2 NASH.

As mentioned non-alcoholic fatty liver disease (NAFLD) represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). The increased generation of free fatty acids for hepatic re-esterification and oxidation results in accumulation of intrahepatic fat and increases the liver's vulnerability to secondary insults. NAFLD is linked to insulin resistance, it causes liver disease in adults and children and may ultimately lead to cirrhosis (Skelly et al., J Hepatol 2001; 35: 195-9; Chitturi et al., Hepatology 2002; 35(2):373-9). The severity of NAFLD ranges from the relatively benign isolated predominantly macrovesicular steatosis (i.e., nonalcoholic fatty liver or NAFL) to non-alcoholic steatohepatitis (NASH) (Angulo et al., J Gastroenterol Hepatol 2002; 17 Suppl:S186-90). NASH is characterized by the histologic presence of steatosis, cytological ballooning, scattered inflammation and pericellular fibrosis (Contos et al., Adv Anat Pathol 2002; 9:37-51). Hepatic fibrosis resulting from NASH may progress to cirrhosis of the liver or liver failure, and in some instances may lead to hepatocellular carcinoma. Because OSEs are inflammatory their presence in liver tissue can lead to increased inflammation and contribute to the progression of liver disease including NASH.

For example, NASH subjects have evidence of increased oxidative stress in the liver, often driven by Kupfer cells and non-enzymatic pathways. In addition, NASH subject have a reduced level of IgM antibodies to OSE compared to normal control (Hendrikxx et al., BMC Med. 14:107, 2016). In addition, Bieghs et al. shows that immunization with heat-inactivated pneumococci, which induce the production of anti-OxLDL antibodies due to molecular mimicry, led to a reduction in hepatic inflammation in NASH-induced mice (Hepatol., 56(3):894-903, 2012). In addition, protection from MDA epitopes resulted in decreased hepatic inflammation in Ldlr$^{-/-}$ mice fed a western diet and treated with a murine anti-MDA antibody (LR04).

The LDL particle is exquisitely sensitive to oxidative damage due to its complex lipid-protein composition and a large number of polyunsaturated acyl chains. The mechanisms of LDL oxidation in vivo include reactions catalyzed by 12/15-lipoxygenase (12/15-LO), myeloperoxidase (MPO), nitric oxide synthases and NADPH oxidases, as well as those mediated by heme and hemoglobin (Hb). Small amounts of Hb are constantly leaking from damaged erythrocytes, particularly in the vascular regions with turbulent flow, such as arterial bifurcations and aortic curvatures, within the intima of the atrial wall and in vasa vasorum of atherosclerotic lesions. The presence of OSEs in clinically relevant human lesions provides a strong rationale to target such epitopes in plasma and in atherosclerotic plaques for clinical applications.

Oxidation of low-density lipoprotein (LDL), as well as oxidized phospholipids on apolipoprotein B-100 (OxPL-apoB), which mainly reflect oxidized phospholipids associated with lipoprotein(a), have been identified as hallmarks of high cardiovascular risk (see, e.g., WO2014/018643, the disclosure of which is incorporated herein by reference). When LDL undergoes oxidation, the byproducts of lipid peroxidation generate many pro-inflammatory chemical modifications of both the lipid and protein moieties, collectively termed oxidation-specific epitopes (OSEs). Several of these OSEs, such as oxidized phospholipids and malondialdehyde epitopes, are well defined chemically and immunologically. They represent danger-associated molecular patterns (DAMPs) and induce a pro-inflammatory response. DAMPs are recognized by the innate immune system via pattern recognition receptors, including scavenger receptors IgM natural antibodies and complement factor H (CFH), that bind, neutralize and/or facilitate their clearance. Additionally, prior work has shown that OSEs can be imaged in zebrafish, mice, and rabbit lipid/atherosclerosis models with murine or human OSE-targeted antibodies using nuclear and MRI techniques. However, the potential immunogenicity of these approaches may limit clinical application.

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb E06, which binds the phosphocholine (PC) headgroup in oxidized phospholipids (OxPL), blocks uptake of OxLDL by macrophages. However, MDA-OSEs are not recognized by E06 and provide the ability for additional diagnostics or therapeutics with respect to those disease or disorders with more prevalent MDA-related-OSEs.

The term "oxidized LDL" is used to describe a wide variety of LDL preparations that have been oxidatively modified ex vivo under defined conditions, or isolated from biological sources.

Malondialdehyde (MDA) is a prominent aldehyde product of lipid peroxidation, as well as of eicosanoid metabolism, which can form adducts with the lysine residues of apoB or other proteins. MDA-modified LDL has also been isolated and characterized from the plasma of patients with coronary heart disease. Malondialdehyde-acetaldehyde (MAA) is a stable and dominant adduct that can form on various proteins and on OxLDL molecules. MAA adducts form an antigenic epitope recognized by antibodies of the disclosure.

The detection of early forms of oxidized LDL in the plasma has been facilitated by the development of monoclonal antibodies (mAbs) specific for the epitopes of oxidized Apo B or oxidized lipids bound to Apo B. The three well-established mAbs used for immunoassays of oxidized LDL are: (i) FOH1a/DLH3, which was generated by immunizing mice against human coronary atheroma, and which recognizes the phosphorylcholine moiety of oxidized PC, but not of normal, PC; (ii) 4E6, which was generated by immunizing mice with $Cu^{2+}$-oxidized LDL, and which recognizes the MDA-modified lysine epitopes of Apo B; and (iii) E06, which was established from the B cell clones of nonimmunized Apo E-deficient mice, and also recognizes the phosphocholine moiety of oxidized but not normal PC. MDA-OSEs are not recognized by the mAb E06, which has specificity for PC.

The disclosure provides an antibody and antibody fragment that recognize MAA-adducts found on various biological molecules including proteins, peptides and, e.g., on MAA-LDL adducts. These antibody and/or antibody fragments can be used as therapies for fatty liver disease including NASH as antibodies to OSEs in subjects having fatty liver disease are decreased compared to normal healthy subjects. Moreover, the antibody and/or antibody fragments can be used in the diagnosis of diseases including but not limited to atherosclerotic disease and disorders and fatty liver disease and disorders.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments. An antibody can be human, humanized and/or affinity matured.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called $\alpha$, $\delta$, $\varepsilon$, $\gamma$, and $\mu$, respectively. The subunit structures and three-dimensional configurations of different classes of immunoglobulins are well known.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

"Antibody fragments" comprise only a portion of an intact antibody, wherein the portion typically retains at least one, more commonly most or all, of the functions normally associated with that portion when present in an intact antibody. Examples of antibody fragments include Fab, Fab', $F(ab')_2$, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

An "antigen" is a predetermined antigen to which an antibody can selectively bind. The target antigen may be polypeptide, carbohydrate, nucleic acid, lipid, hapten or other naturally occurring or synthetic compound. Antigens comprise epitopes that are recognized by antibodies. In a specific embodiment of the disclosure the epitope is a malondialdehyde-acetaldehyde (MAA) adducts. Such MAA adducts may be present on a number of biological factors or molecules including polypeptides and phospholipids and lipoproteins.

The term "anti-OxPL antibody" or "an antibody that binds to OxPL" refers to an antibody that is capable of binding OxPL with sufficient affinity such that the antibody is useful as a diagnostic and/or therapeutic agent in targeting OxPL.

The term "anti-MDA-derived-OxPL" or "anti-MAA-derived-OxPL" refers to antibodies that bind to unique epitopes on OxPL that comprise MDA and/or MAA epitopes.

The term "anti-MAA-adduct" refers to an antibody or antibody fragment that binds to MAA adducts that can be present on proteins, polypeptides, OxPL and other biological molecules.

A "blocking" antibody or an "antagonist" antibody is one which inhibits or reduces biological activity of the antigen it binds. Certain blocking antibodies or antagonist antibodies substantially or completely inhibit the biological activity of the antigen.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

A "disorder" or "disease" is any condition that would benefit from treatment with a substance/molecule or method of the disclosure. This includes chronic and acute disorders or diseases including those pathological conditions that predispose the mammal to the disorder in question. Non-limiting examples of disorders to be treated herein include cardiovascular disease, atherosclerotic disease and disorders, fatty liver disease including NASH, stenosis, disease and disorders that are induced by OxLDL, disease and disorders that are induced by MAA or oxidative stress, and diseases and disorders that lead to ischemic injury due to atherosclerotic plaques.

Antibody "effector functions" refer to those biological activities attributable to the Fc region of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" as used herein refers to the C-terminal region of an immunoglobulin heavy chain, including native sequence Fc regions and variant Fc regions.

A "functional Fc region" possesses an "effector function" of a native sequence Fc region. Such effector functions generally require the Fc region to be combined with a binding to domain (e.g., an antibody variable domain) and can be assessed using various assays as disclosed, for example, in definitions herein.

A "native sequence Fc region" comprises an amino acid sequence that is identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

"Fc receptor" or "FcR" describes a receptor that binds to the Fc region of an antibody. In some embodiments, an FcR is a native human FcR. In some embodiments, an FcR is one that binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

Fc receptor also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

"Fv" is the minimum antibody fragment, which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the $V_H$-$V_L$ dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

A Fab fragment contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains have a free thiol group. $F(ab')_2$ antibody fragments originally were produced as pairs of Fab' fragments which have hinge cysteines between them. Other chemical couplings of antibody fragments are also known.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409. LR04 is a murine antibody of the disclosure that can be humanized as described herein. In contrast, it will be understood that LA25, MK17, KA2 and ML7 are human antibodies.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584). See also, for example, Li et al., Proc. Natl. Acad. Sci. USA, 103:3557-3562 (2006) regarding human antibodies generated via a human B-cell hybridoma technology.

"Human effector cells" are leukocytes that express one or more FcRs and perform effector functions. In certain embodiments, the cells express at least FcγRIII and perform ADCC effector function(s). Examples of human leukocytes that mediate ADCC include peripheral blood mononuclear cells (PBMC), natural killer (NK) cells, monocytes, cytotoxic T cells, and neutrophils. The effector cells may be isolated from a native source, e.g., from blood.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and typically more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated antibody includes the antibody in situ within recombinant cells since at least one component of the antibody's natural environment will not be present. Ordinarily, however, an isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels, a magnetic metal (e.g., paramagnetic) or fluorescent labels) or, in the case of an enzymatic label, may catalyze chemical alteration of a substrate compound or composition which is detectable.

The "light chains" of antibodies (immunoglobulins) from any vertebrate species can be assigned to one of two clearly distinct types, called kappa (κ) and lambda (λ), based on the amino acid sequences of their constant domains.

An "MAA-related disease or disorder" refers to a disease or disorder that is associated or caused by an MAA adduct. Such disease or disorders include inflammatory disease or disorders such as, but not limited to, arthersclerotic diseases or disorder, rheumatoid disease or disorder (e.g., rheumatoid arthritis), lung disease or disorder (e.g., resulting from toxic inhalants and smoking), cancers (e.g., brain cancer such as glioblastoma, skin cancer, colon cancer, breast cancer, prostate cancer, lung cancer, liver cancer etc.), and liver disease and disorders including fatty liver disease, alcoholic liver diseases, non-alcoholic fatty liver disease, non-alcoholic steatohepatitis and the like. Moreover, the MAA-related disease and disorders tend to be related to oxidative stress, which is associated with cardiovascular disease, metabolic syndrome and obesity, autoimmune disease including rheumatoid arthritis, multiple sclerosis, cancer and condition caused by cancer treatment, age related macular degeneration, Alzheimer's disease, senescence, alcoholic liver disease, ischemic reperfusion injury, diabetic nephropathy, nephritis, acute lung injury and invention diseases or any inflamatory condition associated or caused by the foregoing. The antibodies and antibody fragments of the disclosure can specifically bind MAA adducts in such disease and disorder and diagnose the existence of, the prognosis or or treat the disease by inhibiting the inflammatory mediation of such MAA adducts.

The term cardiovascular diseases, is intended to include but is not limited to atherosclerosis, acute coronary syndrome, acute myocardial infarction, myocardial infarction (heart attack), stable and unstable angina pectoris, aneurysms, coronary artery disease (CAD), ischemic heart disease, ischemic myocardium, cardiac and sudden cardiac death, cardiomyopathy, congestive heart failure, heart failure, stenosis, peripheral arterial disease (PAD), intermittent claudication, critical limb ischemia, and stroke. The term fatty liver disease is intended to include non-alcoholic fatty liver disease, steatohepatitis, non-alcoholic steatohepatitis (NASH) and the like.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, a monoclonal antibodies to be used in accordance with the disclosure may be made by a variety of techniques, including, for example, the hybridoma method (e.g., Kohler and Milstein, Nature, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661, 016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include antibodies wherein the antigen-binding region of the antibody is derived from an antibody produced by, e.g., immunizing macaque monkeys with the antigen of interest. For example, LR04 is a murine antibody. A chimeric LR04 antibody would include (a) the murine VH and VL chains (e.g., or Fab region) while including a human Fc region.

"Oligonucleotide," as used herein, refers to short, typically single stranded polynucleotides that are generally, but not necessarily, less than about 200 nucleotides in length. The terms "oligonucleotide" and "polynucleotide" are not mutually exclusive. The description for polynucleotides is equally and fully applicable to oligonucleotides.

"Oxidized phospholipids (OxPL)" refer to phospholipids with a phosphocholine (PC) headgroup. OxPL are highly pro-inflammatory and proatherogenic. Phosphocholine, a polar head group on certain phospholipids, has been extensively implicated in cardiovascular disease. Reactive oxygen species generated during coronary inflammation causes the oxidation of low density lipoprotein (LDL) to generate oxidized LDL (OxLDL). In fact, cardiovascular diseases (CVD) such as atherosclerosis, unstable angina, or acute coronary syndrome have been shown to be associated with elevated plasma levels of OxLDL (Itabe and Ueda. 2007). LDL is a circulating lipoprotein particle that contains lipids with a PC polar head group and proteins, an apoB100 protein.

During oxidation of LDL, PC containing neo-epitopes that are not present on unmodified LDL are generated. Newly exposed PC on OxLDL is recognized by scavenger receptors on macrophages, such as CD36, and the resulting macrophage-engulfed oxLDL proceeds towards the formation of proinflammatory foam cells in the vessel wall. Oxidized LDL is also recognized by receptors on endothelial cell surfaces and has been reported to stimulate a range of responses including endothelial dysfunction, apoptosis, and the unfolded protein response. PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD.

Oxidized phospholipids (OxPL) (phospholipids with a phosphocholine (PC) headgroup) are highly pro-inflammatory and proatherogenic. They are present in a wide spectrum of inflammatory diseases, including atherosclerosis, rheumatoid arthritis, diabetic nephropathy, CNS diseases including multiple sclerosis, fatty liver diseases including non-alcoholic fatty liver disease (NAFLD) and non-alcoholic steatohepatitis (NASH), and a spectrum of acute and chronic pulmonary diseases. For example, OxPL are present in the lungs of both mice and humans infected with a wide variety of viral and bacterial pathogens. OxPL are abundant in bronchial alveolar lavage (BAL) of mice with these infections as well as in acute respiratory distress syndrome following acid installation, or in BAL of mice with COPD secondary to smoking. OxPL are proinflammatory mediators for macrophages, by inducing IL-6 for example, or alternatively inhibit the capacity of macrophages to phagocytize bacteria. OxPL are prevalent in livers of patients and mice with NASH, and have been shown to be involved in the pathogenesis in murine models of NASH. OxPL are also extensively present in atherosclerotic lesions, and in vulnerable plaques of human coronary arteries. They are also released into the circulation during interventional procedures such as PCI and stenting, where they likely mediate downstream proinflammatory and vasoactive effects.

Antibodies towards phosphocholine (PC) have been shown to bind oxidized, or otherwise modified, LDL and block the pro-inflammatory activity of OxLDL in in vivo models or in vitro studies (Shaw et al. 2000; Shaw et al. 2001).

A "polynucleotide," or "nucleic acid," as used herein, refer to polymers of nucleotides of any length, and include DNA and RNA. The nucleotides can be deoxyribonucleotides, ribonucleotides, modified nucleotides or bases, and/or their analogs that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.). The preceding description applies to all polynucleotides referred to herein, including RNA and DNA.

"Single-chain Fv" or "scFv" antibody fragments comprise the $V_H$ and $V_L$ domains of antibody, wherein these domains are present in a single polypeptide chain. Generally, the scFv polypeptide further comprises a polypeptide linker between the $V_H$ and $V_L$ domains, which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, and/or less than about 10% as a function of the reference/comparator value.

The phrase "substantially reduced," "substantially increased," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a (3-sheet configuration, connected by three HVRs, which form loops connecting, and in some cases forming part of, the (3-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and replicate along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies and tetrabodies are also described in Hudson et al., Nat. Med. 9:129-134 (2003).

A "variant Fc region" comprises an amino acid sequence, which differs from that of a native sequence Fc region by virtue of at least one amino acid modification, typically one or more amino acid substitution(s). Typically, the variant Fc region has at least one amino acid substitution compared to a native sequence Fc region or to the Fc region of a parent polypeptide, e.g. from about one to about ten amino acid substitutions, and typically from about one to about five amino acid substitutions in a native sequence Fc region or in the Fc region of the parent polypeptide. The variant Fc region of a disclosure possesses at least about 80% homology with a native sequence Fc region and/or with an Fc region of a parent polypeptide, at least about 90% homology therewith, and typically at least about 95% homology therewith.

This disclosure describes the generation of a monoclonal antibody and antibody fragments directed to oxidation-specific epitopes, specifically malondialdehyde-acetaldehyde (MAA) epitopes that are involved in a variety of diseases, including cardiovascular disease, liver disease and neurological diseases. The antibody or antibody fragment can be used as a biomarker, molecular imaging agent and therapeutic ("biotheranostic") in these disease states. This antibody or antibody fragment can be used as a "passive vaccination" approach to prevent diseases, e.g., atherosclerosis or liver disease.

The antibodies and antibody fragments of the disclosure were generated by screening a phage display library for antibodies and then documenting appropriate properties for binding the antigen (MAA). The screening process, antigen selection, its specificity for its target and resulting sequences provides an antibody that is useful for treating humans.

The antibodies of the disclosure can be used in a variety of settings, including immunoassays in plasma in clinical and research assays, immunostaining of tissues, molecular imaging after adding appropriate tags and as an infusion for therapeutic purposes in humans.

The disclosure also provides for single chain variable antibody fragments ("scFv"), $V_H$, $V_L$ and complementarity determining regions that selectively bind to MAA-OSEs. The scFvs of the disclosure are soluble and can be readily synthesized. Further, vectors comprising sequences encoding the scFvs disclosed herein enabled the production of a transgenic murine model as well as production in a variety of host cell lines and organisms.

The disclosure provides sequences associated with the light and heavy chains or the antibodies of the disclosure (see, FIG. 27 and SEQ ID Nos:1-20).

The disclosure provides antibodies, antibody fragments, human and humanized antibodies that bind to MAA-OSE. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tumors, plaques and diseased tissue. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. Coli, thus allowing the facile production of large amounts of these fragments. Antibody fragments can be isolated from the antibody phage libraries. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No.

5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

The disclosure, although providing specific antibody sequences and antibody sequence fragments having biological activity, further disclose that these sequence can be used to generate improved variants. Accordingly, in some instances an antibody or antibody fragment may have a percent identity to the sequences of the disclosure (e.g., 99%-99.9% identity to SEQ ID NO:1-19 or 20).

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis (e.g., modifications of the sequences set forth in FIG. 27 and SEQ ID Nos:1-20). Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as Arg, Asp, His, Lys, and Glu) and replaced by a neutral or negatively charged amino acid (e.g., Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody. Polyhistidine tags are also useful for purification.

In certain embodiments, an antibody of the disclosure is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn of the $CH_2$ domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al.), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions that further improve ADCC. Such substitutions may occur in combination with any of the variations described above.

In certain embodiments, the disclosure contemplates an antibody variant that possesses some but not all effector functions, which make it a desirable candidate for many applications in which the half-life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks a particular binding but retains other binding. Non-limiting examples of in vitro assays to assess ADCC activity of a molecule of interest is described in U.S. Pat. No. 5,500,362 (see, e.g. Hellstrom, I., et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, for example, Petkova, S. B. et al., Int'l. Immunol. 18(12):1759-1769 (2006)).

Other antibody variants having one or more amino acid substitutions are provided. Sites of interest for substitutional mutagenesis include the hypervariable regions, but FR alterations are also contemplated. Conservative substitutions can also be performed. Amino acid substitutions may be introduced into an antibody of interest and the products screened, e.g., for a desired activity, such as improved antigen binding, decreased immunogenicity, improved ADCC or CDC, etc.

The disclosure provides an antibody or antibody fragment capable of binding to MAA-OSEs or other MAA related adducts, wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from Table 1, wherein only one CDR is selected from each column of CDR1, CDR2 and CDR3; and (b) the $V_L$ domain comprises an amino acid sequence that includes one, two or three complementarity determining regions (CDRs) selected from Table 1, wherein only one CDR is selected from each column of CDR1, CDR2 and CDR3.

TABLE 1

| Antibody Designation | CDR1 (SEQ ID NO:) | CDR2 (SEQ ID NO:) | CDR3 (SEQ ID NO:) |
| --- | --- | --- | --- |
| KA2 VH | GFTFSSYW (25) | INSDGSST (26) | CARDYSSSWYFDYW (27) |
| LR04 VH | GYTFTTYG (28) | INTYSGVP (29) | CAKLGFAYW (30) |
| ML7 VH | GFTFSSYG (31) | IWYDGSNK (32) | CARGSLSGLDVW (33) |
| MK17 VH | GFTFSSYG (34) | IWYDGSNK (35) | CARDRGYPWLRSRGGMDV (36) |
| LA25 VH | GFTFSSYG (37) | IWYDGSNK (38) | CARGRWGGYFDLW (39) |

TABLE 2

| Antibody Designation | CDR1 (SEQ ID NO:) | CDR2 (SEQ ID NO:) | CDR3 (SEQ ID NO:) |
| --- | --- | --- | --- |
| KA2 VL | QSLLHSNGYNY (40) | LGS (41) | CMQALQTHSF (42) |
| LR04 VL | KSLLHSNGNTY (43) | RMS (44) | CMQHLEYPYTF (45) |
| ML7 VL | SSNIGSNY (46) | SNN (47) | CAAWDVSLRQWLF (48) |
| MK17 VL | QGIGNY (49) | AAS (50) | CQQLNGYPLTF (51) |
| LA25 VL | SSDVGGYNY (52) | EVS (53) | CSSYAGSNNYWV (54) |

In one embodiment, the antibody or antibody fragment comprises a $V_H$ and/or $V_L$ domain comprises (a) an amino acid sequence as set forth in SEQ ID NO:2 and/or 4), (b) SEQ ID NO:6 and/or 8, (c) SEQ ID NO:10 and/or 12, (d) SEQ ID NO:14 and/or 16, (e) SEQ ID NO:18 and/or 20, (f) sequences that are at least 98-99.9% identical thereto or fragments thereof containing at least one CDR from each antibody designation in Table 1 and/or 2 and wherein the antibody or antibody fragment binds to an MAA adduct.

In one embodiment, the disclosure provides an antibody or an scFv with heavy and light chain domains comprising the complementarity determining regions contained in the amino acid sequences of FIG. 27 (or sequences that are 98-99.9% identical thereto). In one embodiment the scFv are linked to an Fc region.

In one embodiment, the disclosure provides an antibody comprising a light-chain variable region as set forth in SEQ ID NO:2, 6, 10, 14, or 18; or a sequence that is 98, 99 or 99.9% identical thereto). In another embodiment, the disclosure provides an antibody with a humanized light chain variable region of SEQ ID NO:10 (LRO4). In another embodiment, the disclosure provides an antibody that comprises a heavy chain variable region comprising a sequence as set forth in SEQ ID NO:4, 8, 12, 16 or 20; or a sequence that is 98, 99 or 99.9% identical thereto). In another embodiment, the disclosure provides an antibody that comprises a humanized heavy chain variable region of SEQ ID NO:12 (LRO4).

In another embodiment, the disclosure provides a chimeric antibody comprising, for example, a VH and/or VL of SEQ ID NO:10 and/or 12, respectively, and a human Fc region.

In one embodiment, the disclosure provides an scFv comprising a linker between the light change variable region and the heavy-chain variable region. The linker can be any number of commonly used peptide linkers. In one embodiment, the linker comprises a repeating unit of GGGS (SEQ ID NO:57). The repeat of GGGS may be 2, 3, 4 or more times.

In another embodiment, the disclosure comprises a scFv comprising a light chain variable region as set forth in FIG. 27 (e.g., SEQ ID NO:2, 6, 10, 14 or 18) linked by a peptide linker to it's corresponding heavy chain variable region as set forth in FIG. 27 (e.g., SEQ ID NO:4, 8, 12, 16 or 20), respectively. In a further embodiment, the disclosure provides for an scFv that has a polypeptide sequence that has at least 75%, at least 80%, at least 85%, at least 90%, at least 95%, at least 98%, at least 99% or at least 99.9% sequence identity to the sequences set forth in FIG. 27 and which selectively binds to an MAA-OSE on an oxidized phospholipid.

Nucleic acid molecules encoding the amino acid sequences of the antibodies, antibody fragments and variants of the antibody are prepared by a variety of methods known in the art. Nucleic acid coding sequences for the antibodies and antibody fragments described herein are provided in FIG. 27 and SEQ ID Nos:1, 3, 5, 7, 9, 11, 13, 15, 17 and 19.

In a particular embodiment, the disclosure provides for a scFv which is encoded by a polynucleotide sequence provided in FIG. 27 (e.g., SEQ ID NO:1 and/or 3; SEQ ID NO:5 and/or 7; SEQ ID NO:9 and/or 11; SEQ ID NO:13 and/or 15; or SEQ ID NO:17 and/or 19). In a further embodiment, the disclosure provides for a scFv which is encoded by a polynucleotide sequence that has at least 75%, at least 80%, at least 85%, at least 90%, at least 95%, at least 98%, at least 99% or at least 99.9% sequence identity to the sequences in FIG. 27 and which produces a polypeptides that selectively binds to MAA-OSEs.

The disclosure also encompasses humanized antibodies containing sequence from SEQ ID NO:10 and 12 (LRO4). Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The disclosure further provides for a scFv disclosed herein that further comprises a fragment crystallizable region ("Fc") of an antibody. In a particular embodiment, the Fc region is from a human or humanized antibody. The Fc region is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. The other part of an antibody, called the Fab region, contains variable sections that define the specific target that the antibody can bind. The scFv of the disclosure are comprised of elements from the Fab region. By contrast, the Fc region of all antibodies in a class are the same for each species; they are constant rather than variable. The Fc region is, therefore, sometimes termed the "fragment constant region". Accordingly, the polynucleotide and polypeptide sequences which encode the Fc regions for countless species have already been determined and would be known by one of skill in the art.

Polynucleotide sequences encoding polypeptide components of the antibody or antibody fragments of the disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of nucleic acids differing in their nucleotide sequences can be used to encode a given antibody of the disclosure.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage vectors may be utilized in making a recombinant vector which can be used to transform susceptible host cells such as *E. coli* LE392.

The expression vector of the disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one embodiment, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another embodiment, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the disclosure include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the disclosure. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 (U.S. Pat. No. 5,639,635). Other strains and derivatives thereof, such as *E. coli* 294 (ATCC 31,446), *E. coli* B, *E. coli* X 1776 (ATCC 31,537) and *E. coli* RV308 are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well-known plasmids such as pBR322, pBR325, pACYC177, or pKN410 are used to supply the replicon.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures.

In one embodiment, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Large scale or small scale fermentation can be used and can be optimized using skills well known in the art.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration.

The disclosure further provides for an expression vector which encodes a scFv or humanized antibody disclosed herein that is transferred into a suitable host organism. The suitable host organism is a microorganism, yeast or a mammalian cell system. Typically, the mammalian cell system is monocyte-derived (e.g., macrophages, monocytes, and neutrophils), lymphocyte-derived (e.g., myeloma, hybridoma, and a normal immortalized B cell), parenchymal (e.g., hepatocytes) and non-parenchymal cells (e.g., stellate cells).

Additionally, the disclosure also provides for a unique transgenic animal model that expresses a scFv disclosed herein from both the liver and from macrophages. This animal model allows for a systematic study of the therapeutic effects of the scFvs of the disclosure in a wide variety of physiological and pathophysiological settings. The methods and compositions presented herein can be equally as well be applied to create transgenic models in any number of animals including, but not limited to, rats, rabbits, pigs, sheep, goats, and horses. The disclosure, therefore, provides methods that can be performed in vivo to study the therapeutic possibilities of a scFv of the disclosure or an antibody of the disclosure in a highly defined manner. For example, a desirable scFv can be produced during cell culturing or in a transgenic animal. The availability of a transgenic animal model expressing a scFv disclosed herein allows for in-depth preclinical testing for myriad of potential applications. For example, interventions can be done on the transgenic animals to test the impact of scFv expression, including, by breeding the animals into a variety of backgrounds.

The antibody and antibody fragments disclosed herein bind to MAA adducts and can block their pro-inflammatory effects. Such proinflammatory effects include MAA-related disease and disorders and are relevant to, for example, cardiovascular disease, artherosclerosis, rheumatoid arthritis, lung tissue injury (e.g., caused by smoking), brain lesions, apoptosis, senescence and fatty liver disease (e.g., NASH). The in vivo use of an antibody fragment (humanized, human and non-humanized) of the disclosure or a human, humanized and non-human antibody of the disclosure can be used to (a) block inflammation from MAA adducts, (b) treat any one or more of cardiovascular disease, arthersclerosis, rheumatoid arthritis, lung tissue injury (e.g., cause by smoking), brain lesions, apoptosis, senescence and fatty liver disease (e.g., NASH) by blocking the inflammatory effects of MAA adducts, (c) detect and/or diagnose inflammatory disease or disorders by detecting MAA adducts in a sample from or tissue in a subject. For example, the antibody or antibody fragments of the disclosure can be used to treat atherosclerotic diseases and disorders and fatty liver disease including NASH. In addition, the antibody or antibody fragments of the disclosure can be labeled and used as diagnostics wherein their binding can be imaged or analyzed to determine the location and/or severity of MAA adducts. Such diagnostics can be used to determine the presence of atherosclerotic disease and disorders as well as fatty liver disease including NASH etc.

An embodiment of the disclosure is a method of treating NASH or NAFLD in a patient in need of such therapy, with a human, or humanized antibody targeting MAA, or fragment thereof, wherein the treatment decreases liver fat, or inflammation or disease. Such a decrease in liver fat can be measured, e.g., by magnetic resonance imaging-proton density fatty fraction (MRI-PDFF). An embodiment of the disclosure is a method of treating NASH or NAFLD in a patient in need of such therapy, with a human, or humanized antibody targeting MAA, or fragment thereof as disclosed herein, wherein the treatment decreases liver fibrosis as measured by magnetic resonance elastography (MRE) and/or decreases inflammation and/or provide a return of liver function biomarkers to within normal ranges. In another embodiment, the one or more markers of liver function are selected from the group consisting of alanine aminotransferase (ALT), alkaline phosphatase (ALP), aspartate aminotransferase (AST), gamma-glutamyl transpeptidase (GGT), triglycerides, and lipoproteins (e.g., LDL). In a further embodiment, an ALT level of about 60-150 units/liter is indicative of fatty liver disease. In yet another or further embodiment, an ALP level of about 150-250 units/liter is indicative of fatty liver disease. In yet another of further embodiment, an AST level of about 40-100 units/liter is indicative of fatty liver disease. In still another or further embodiment, a GGT level of 50-100 units/liter is indicative of fatty liver disease. In still another of further embodiment, a triglyceride level above 150 mg/dL and/or high LDL level is indicative of fatty liver disease. In yet another or further embodiment, a resistin level of greater than 8 ng/ml is indicative of fatty liver disease. In still yet another or further embodiment, an adiponectin level decreased by at least about 20% from age and sex matched normal subjects is indicative of fatty liver disease. An effective therapy using an antibody or fragment of the disclosure would decrease the levels of AST to between 10 to 40 units/L, ALT to between 7 and 56 units/L, ALP to between 44 and 147 units/L etc. An embodiment of the disclosure is a method of treating NASH or NAFLD in a patient in need of such therapy, with a human, or humanized antibody targeting MAA, or fragment thereof, wherein the treatment decreases liver fibrosis as measured by MRE or decreases liver fat as measured MRI-PDFF accompanied by an improvement in liver function as measured by ALT, AST, AST/ALT ratios, bilirubin or GGT. In one embodiment of the disclosure, a method of treating NASH or NAFLD in a patient in need of such therapy, with a human, or humanized antibody targeting MAA, or fragment thereof, wherein the treatment decreases liver fibrosis as measured by MRE or decreases liver fat as measured MRI-PDFF accompanied by an improvement in insulin sensitivity, for example, as measured by HbA1c.

The antibodies, antibody fragments and polypeptides of the disclosure may be used to inhibit or reduce the formation of a senescent cell in a clinically significant or biologically significant manner. As discussed in detail herein, the antibodies, antibody fragments and polypeptides of the disclosure are used in an amount and for a time sufficient that prohibit or reduce the formation of senescent cells in a clinically significant or biologically significant manner. The antibodies, antibody fragments and polypeptides of the disclosure can prohibit or reduce the formation of one or more types of senescent cells (e.g., senescent preadipocytes, senescent endothelial cells, senescent fibroblasts, senescent neurons, senescent epithelial cells, senescent mesenchymal cells, senescent smooth muscle cells, senescent macrophages, or senescent chondrocytes).

A senescent cell may exhibit any one or more of the following seven characteristics. (1) Senescence growth arrest is essentially permanent and cannot b e reversed by known physiological stimuli. (2) Senescent cells increase in size, sometimes enlarging more than twofold relative to the size of non-senescent counterparts. (3) Senescent cells express a senescence-associated b-galactosidase (SAP-gal), which partly reflects the increase in lysosomal mass. (4) Most senescent cells express p16INK4a, which is not commonly expressed by quiescent or terminally differentiated cells. (5) Cells that senesce with persistent DDR signaling harbor persistent nuclear foci, termed DNA segments with chromatin alterations reinforcing senescence (DNA-SCARS). These foci contain activated DDR proteins and are distinguishable from transient damage foci. DNA-SCARS include dysfunctional telomeres or telomere dysfunction-induced foci (TIF). (6) Senescent cells express and may secrete molecules associated with senescence, which in certain instances may be observed in the presence of persistent DDR signaling, which in certain instances may be dependent on persistent DDR signaling for their expression. (7) The nuclei of senescent cells lose structural proteins such as Lamin B 1 or chromatin-associated proteins such as histones and HMGB1. See, e.g., Freund et al, Mol. Biol. Cell 23:2066-75 (2012); Davalos et al, J. Cell Biol. 201:613-29 (2013); Ivanov et al, J. Cell Biol. DOI:10. 1083/jcb. 2012121 10, page 1-15; published online Jul. 1, 2013; Funayama et al, J. Cell Biol. 175:869-80 (2006)).

Senescent cells and senescent cell associated molecules can be detected by techniques and procedures described in the art. For example, the presence of senescent cells in tissues can be analyzed by histochemistry or immunohistochemistry techniques that detect the senescence marker, SA-beta galactosidase (SA-Pgal) (see, e.g., Dimri et al, Proc. Natl. Acad. Sci. USA 92: 9363-9367 (1995)). The presence of the senescent cell-associated polypeptide p16 can be determined by any one of numerous immunochemistry methods practiced in the art, such as immunoblotting analysis. Expression of p16 mRNA in a cell can be measured by a variety of techniques practiced in the art including quantitative PCR. The presence and level of senescent cell associated polypeptides (e.g., polypeptides of the SASP) can be determined by using automated and high throughput assays, such as an automated Luminex array assay described in the art (see, e.g., Coppe et al., PLoS Biol 6: 2853-68 (2008)).

The presence of senescent cells can also be determined by detection of senescent cell-associated molecules, which include growth factors, proteases, cytokines (e.g., inflammatory cytokines), chemokines, cell-related metabolites, reactive oxygen species (e.g., $H_2O_2$), oxidation specific epitopes, such as MAA, and other molecules that stimulate inflammation and/or other biological effects or reactions that may promote or exacerbate the underlying disease of the subject. Senescent cell-associated molecules include those that are described in the art as comprising the senescence-associated secretory phenotype (SASP, i.e., which includes secreted factors which may make up the pro-inflammatory phenotype of a senescent cell), senescent-messaging secretome, and DNA damage secretory program (DDSP). These groupings of senescent cell associated molecules, as described in the art, contain molecules in common and are not intended to describe three separate distinct groupings of molecules. Senescent cell-associated molecules include certain expressed and secreted growth factors, proteases, cytokines, and other factors that may have potent autocrine and paracrine activities (see, e.g., Coppe et al., supra; Coppe et al. J. Biol. Chem. 281:29568-74 (2006); Coppe et al., PLoS One 5:39188 (2010); Krtolica et al. Proc. Natl. Acad. Sci. U.S.A. 98:12072-77 (2001); Parrinello et al., J. Cell Sci. 118:485-96 (2005). ECM associated factors include inflammatory proteins and mediators of ECM remodeling and which are strongly induced in senescent cells (see, e.g., Kuilman et al., Nature Reviews 9:81-94 (2009)). Other senescent cell-associated molecules include extracellular polypeptides (proteins) described collectively as the DNA damage secretory program (DDSP) (see, e.g., Sun et al., Nature Medicine 18:1359-1368 (2012)). Senescent cell-associated proteins also include cell surface proteins (or receptors) that are expressed on senescent cells, which include proteins that are present at a detectably lower amount or are not present on the cell surface of a nonesenescent cell.

Senescence cell-associated molecules include secreted factors which may make up the pro-inflammatory phenotype of a senescent cell (e.g., SASP). These factors include, without limitation, GM-CSF, GROa, GRC-a,b,g, IGFBP-7, IL-1a, IL-6, IL-7, IL-8, MCP-1, MCP-2, MIP-1a, MMP-1, MMP-10, MMP-3, Amphiregulin, ENA-78, Eotaxin-3, GCP-2, GITR, HGF, ICAM-1, IGFBP-2, IGFBP-4, IGFBP-5, IGFBP-6, IL-13, IL-I b, MCP-4, MIF, MIP-3a, MMP-12, MMP-13, MMP-14, NAP2, Oncostatin M, osteoprotegerin, PIGF, RANTES, sgp130, TIMP-2, TRAIL-R3, Acrp30, angiogenin, Axl, bFGF, BLC, BTC, CTACK, EGF-R, Fas, FGF-7, G-CSF, GDNF, HCC-4, 1-309, IFN-g, IGFBP-1, IGFBP-3, IL-1 R1, IL-1 1, IL-15, IL-2R-a, IL-6 R, ITAC, Leptin, LIF, MMP-2, MSP-a, PAI-1, PAI-2, PDGF-BB, SCF, SDF-1, sTNF RI, sTNF RII, Thrombopoietin, TIMP-1, tPA, uPA, uPAR, VEGF, MCP-3, IGF-1, TGF-b3, MIP-1-delta, IL-4, FGF-7, PDGF-BB, IL-1 6, BMP-4, MDC, MCP-4, IL-10, TIMP-, Fit-3 Ligand, ICAM-1, Axl, CNTF, INF-g, EGF, BMP-6. Additional identified factors, which include those sometimes referred to in the art as senescence messaging secretome (SMS) factors, some of which are included in the listing of SASP polypeptides, include without limitation, IGF1, IGF2, and IGF2R, IGFBP3, IDFBP5, IGFBP7, PA11, TGF-b, WNT2, IL-1a, IL-6, IL-8, and CXCR2-binding chemokines. Cell-associated molecules also include without limitation the factors described in Sun et al, Nature Medicine, supra, and include, including, for example, products of the genes, MMPI, WNT16B, SFRP2, MMP12, SPINK1, MMP10, ENPP5, EREG, BMP6, ANGPTL4, CSGALNACT, CCL26, AREG, ANGPT1, CCK, THBD, CXCL14, NOV, GAL, NPPC, FAM150B, CST1, GDNF, MUCL1, NPTX2, TMEM155, EDN1, PSG9, ADAMTS3, CD24, PPBP, CXCL3, MMP3, CST2, PSG8, PCOLCE2, PSG7, INFSF15, Cl7orf67, CALCA, FGF18, IL8, BMP2, MATN3, TFP1, SERPINI 1, TNFRSF25, and IL23A. Senescent cell-associated proteins also include cell surface proteins (or receptors) that are expressed on senescent cells, which include proteins that are present at a detectably lower amount or are not present on the cell surface of a non-senescent cell.

In certain embodiments, the antibodies, antibody fragments and polypeptides of the disclosure are capable of prohibiting, inhibiting or reducing the formation of at least senescent preadipocytes may be useful for treatment of diabetes (particularly type 2 diabetes), metabolic syndrome, or obesity. In other embodiments, the antibodies, antibody fragments and polypeptides of the disclosure are capable of prohibiting or reducing the formation of at least senescent endothelial cells, senescent smooth muscle cells, and/or senescent macrophages. The antibodies, antibody fragments and polypeptides of the disclosure may be useful for treatment of a cardiovascular disease (e.g., atherosclerosis). In other particular embodiments, the antibodies, antibody fragments and polypeptides of the disclosure are capable of prohibiting or reducing the formation of at least senescent fibroblasts. In still another embodiment, the antibodies, antibody fragments and polypeptides of the disclosure are capable of prohibiting or reducing the formation of at least senescent neurons, including dopamine-producing neurons. In still another embodiment, the antibodies, antibody fragments and polypeptides of the disclosure are capable of prohibiting or reducing the formation of at least senescent retinal pigmented epithelial cells or other senescent epithelial cells (e.g., pulmonary senescent epithelial cells or senescent kidney (renal) epithelial cells). Prohibiting or reducing the formation of at least senescent pulmonary epithelial cells may be useful for treating pulmonary diseases, such as chronic obstructive pulmonary disease or idiopathic pulmonary fibrosis. In yet other embodiments, the antibodies, antibody fragments and polypeptides of the disclosure are capable of prohibiting or reducing the formation of at least senescent immune cells (such as senescent macrophages). In still another embodiment, the antibodies, antibody fragments and polypeptides of the disclosure are capable of prohibiting or reducing the formation of at least senescent chondrocytes, which may be useful for treatment of an inflammatory disorder, such as osteoarthritis.

Thus, the antibodies, antibody fragments and polypeptides of the disclosure can be used to treat inflammatory diseases and disorders, cardiovascular diseases, liver diseases and disorder (e.g., NASH) and diseases associated with oxidative stress and damage.

For diagnostic applications, the antibody or antibody fragments of the disclosure will be labeled with a detectable moiety. The detectable moiety can be any one which is capable of producing, either directly or indirectly, a detectable signal. For example, the detectable moiety may be a radioisotope, such as 3H, 14C, 32 P, $^{35}$S, or $^{131}$I; a fluorescent or chemiluminescent compound, such as fluorescein isothiocyanate, rhodamine, or luciferin; a magnetic or paramagnetic element or compound, or an enzyme, such as alkaline phosphatase, beta-galactosidase or horseradish peroxidase. In some embodiments, therapeutic or diagnostic radioisotopes or other labels (e.g., PET or SPECT labels) can be incorporated in the agent for conjugation to the EGFRvIII antibodies as described herein. Examples of a radioisotope or other labels include, but are not limited to, $^{11}$C, $^{13}$N, $^{15}$N, $^{15}$O, $^{35}$B, $^{18}$F, $^{33}$P, $^{47}$Sc, $^{51}$Cr, $^{57}$Co, $^{58}$Co, $^{53}$Fe, $^{62}$Cu, $^{64}$Cu, $^{67}$Cu, $^{67}$Ga, $^{68}$Ga, $^{75}$Se, $^{76}$Br, $^{77}$Br, $^{86}$Y, $^{89}$Zr, $^{90}$Y, $^{94}$Tc, $^{95}$Ru, $^{97}$Ru, $^{99}$Tc, $^{103}$Ru, $^{105}$Rh, $^{105}$Ru, $^{107}$Hg, $^{109}$Pd, $^{111}$Ag, $^{111}$In, $^{113}$In, $^{121}$Te, $^{122}$Te, $^{123}$I, $^{124}$I, $^{125}$I, $^{125}$Te, $^{126}$I, $^{131}$In, $^{131}$I, $^{142}$Pr, $^{143}$Pr, $^{153}$Pb, $1^{53}$Sm, $^{161}$Tb, $^{165}$Tm, $^{166}$Dy, $^{166}$H, $^{167}$Tm, $^{168}$Tm, $^{169}$Yb, $^{177}$Lu, $^{186}$Re, $^{188}$Re, $^{189}$Re, $^{197}$Pt, $^{198}$Au, $^{199}$Au, $^{201}$Tl, $^{203}$Hg, $^{211}$At, $^{212}$Bi, $^{212}$Pb, $^{213}$Bi, $^{223}$Ra, $^{224}$Ac, or $^{225}$Ac.

Any method known in the art for conjugating the antibody or fragment to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The antibodies or fragment thereof of the disclosure also are useful for in vivo imaging, wherein an antibody labeled with a detectable moiety such as a magnetic, paramagnetic, radio-opaque agent or radioisotope is administered to a subject, typically into the bloodstream, and the presence and location of the labeled antibody in the host is assayed. This imaging technique is useful in identifying oxidized phospholipid deposition for the determination of fatty liver disease, NASH, atherosclerotic plaques and cardiovascular diseases or disorders. Such methods can be used to determine the existence of a disease and/or to follow the disease progression and treatment (e.g., imaging before and then after a round of treatment to determine a therapeutic effect and/or progression of the disease). The antibody may be labeled with any moiety that is detectable in a host, whether by nuclear magnetic resonance, radiology, or other detection means known in the art.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, a scFv (humanized or non-humanized) of the disclosure or a humanized antibody of the disclosure are used to delay development of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the disclosure, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Therapeutic and/or diagnostic formulations/preparations comprising an antibody or fragment thereof of the disclosure are prepared for storage by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Anti-MAA-OSE antibodies of the disclosure can be produced transgenically through the generation of a mammal or plant that is transgenic for the immunoglobulin heavy and light chain sequences of interest and production of the antibody in a recoverable form therefrom. In connection with the transgenic production in mammals, anti-MAA-adduct antibodies can be produced in, and recovered from, the milk of goats, cows, or other mammals. See, e.g., U.S. Pat. Nos. 5,827,690, 5,756,687, 5,750,172, and 5,741,957, incorporated herein by reference.

In some embodiments, non-human transgenic animals or plants are produced by introducing one or more nucleic acid molecules encoding an anti-MAA-adduct antibody or fragment thereof of the disclosure into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999), all incorporated herein by reference. In some embodiments, the transgenic non-human animals have a targeted disruption and replacement by a targeting construct that encodes a heavy chain and/or a light chain of interest. In another embodiment, the transgenic animals comprise and express nucleic acid molecules encoding heavy and light chains that specifically bind to MAA epitopes or other MAA adducts. In some embodiments, the transgenic animals comprise nucleic acid molecules encoding a modified antibody such as a single-chain antibody, a chimeric antibody or a humanized antibody. The antibodies may be made in any transgenic animal. In another embodiment, the non-human animals are mice, rats, sheep, pigs, goats, cattle or horses. The non-human transgenic animal expresses said encoded polypeptides in blood, milk, urine, saliva, tears, mucus and other bodily fluids.

The following examples are intended to illustrate but not limit the disclosure. While they are typical of those that might be used, other procedures known to those skilled in the art may alternatively be used.

EXAMPLES

Cloning and characterization of LA25. Human LDL was freshly isolated from plasma of healthy donors after an overnight fast by sequential ultra-centrifugation. LDL (or bovine serum albumin (BSA)) was modified with MAA, MDA or $CuSO_4$ to generate MAA-LDL, MAA-BSA, MDA-LDL or copper-oxidized LDL (Cu-OxLDL) respectively. In MAA and MDA preparations, >90% of the lysines were modified as judged using the trinitrobenzenesulfonic acid assay.

To enrich for antibodies, a library (κ/λ) was constructed from lymphocytes of umbilical cord blood of 7 newborn babies and used in the first round of screening. The selecting epitope was MAA-BSA. MAA is a specific advanced MDA-type adduct that has been shown as an immunodominant MDA epitope. After 4 rounds of panning with each library, an enrichment in the newborn library of fully or very near germline sequences, consistent with minimal non-templated insertions in the CDR3 region was obtained. The resultant Fabs were cloned into the phagemid pComb3X. LA25 was identified as a leading candidate due to its specificity for MAA epitopes and optimal expression characteristics. LA24 was identified from the same library, but did not bind any relevant oxidation-specific epitopes present in vivo. Specificity of individual phage Fab and soluble Fab were assessed by ELISA. The specificity of Fab binding was further determined by competition chemiluminescent ELISA and data expressed as $B/B_0$, where B represents binding in the presence and $B_o$ in the absence of competitor. High-titer clone LA25 and control LA24 were selected and converted to the plasmid producing soluble Fab. Nucleotide and amino acid sequences of Fab clones were compared to those contained in public databases by using Ig-BLAST and IMGT/VQUEST. LA25 and LA24 plasmid from selected Fab phage clones were codon optimized and transformed into *E. coli* C41 (DE3) (Lucigen) for production of soluble Fab.

Mouse and Rabbit atherosclerosis models. Female $Apoe^{-/-}$ mice (B6.129P2-$Apoe^{tm1Unc}$/J, 8-10 weeks old) were purchased from the Jackson Laboratory (Bar Harbor, Me.) and fed a Western diet (Harlan Teklad TD.88137, 42% calories from fat) for 22 weeks. Male New Zealand White rabbits (2.5-3.0 months old) were purchased from Charles River Laboratories (Wilmington, Mass.). To promote the formation of atherosclerotic plaques, endothelial denudation of the aorta was performed after intramuscular (i.m.) administration of ketamine (20 mg/kg) (Fort Dodge Animal Health, Overland Park, Kansas, USA) and Xylazine (5 mg/kg) (Bayer AG, Leverkusen, Germany). A 4F-Fogarty embolectomy catheter (Edwards Lifesciences, Irvine, CA) was inflated at the level of the left subclavian artery and slowly deflated while retracting until the iliac bifurcation, under X-ray guidance (Philips Allura Xper FD20/10, Philips Healthcare, Best, The Netherlands). The procedure was repeated using the contralateral femoral artery as point of entry 4 weeks after the first procedure, i.e., 6 weeks after the initiation of a high cholesterol diet (regular chow diet enriched with 0.3% cholesterol, 4.7% coconut oil, Research diets, Inc., Brunswick, NJ). After 8 weeks, diet was changed to a 0.15% enriched cholesterol diet and continued for the remaining 2.5 months before the experiments were performed. Untreated healthy rabbits were fed a regular chow diet and age-matched to serve as controls.

All animal experiments were performed in accordance with protocols approved by the Institutional Animal Care and Use Committees of the institution and followed National Institutes of Health guidelines for animal welfare.

Immunostaining of human specimens. Hearts of patients who had died suddenly with coronary artery disease were obtained. Cases were identified retrospectively by the presence of early and late fibroatheroma, thin cap fibroatheroma and plaque rupture. Formalin-fixed, paraffin embedded coronary segments were cut at 5-μm thick sections, mounted on charged slides, and stained with hematoxylin and eosin (H&E) or the modified Movat pentachrome method.

Paraffin embedded tissue sections were deparaffinized with Histoclear®, rehydrated through graded ethanol, and blocked with 5% normal goat serum/1% BSA/TBS for 30 minutes. Tissues were incubated overnight at 4° C. with the human monoclonal antibody Fab LA25 or LA24 diluted with blocking buffer. Using the avidin-biotin-alkaline phosphatase method, tissues were incubated for 30 minutes with biotinylated monoclonal anti-HA antibody diluted with blocking buffer in a ratio of 1:1000 (Sigma B9183). Tissues were then incubated with ABC Alkaline phosphatase reagent (Vector AK-5000) for 30 minutes and visualized with Vector Red substrate (Vector SK-5100). Finally, slides were then counterstained with hematoxylin for 30 seconds, dehydrated through graded ethanol, cleared with Histoclear and a coverslip was adhered using histomount. Immunostaining of adjacent sections in the absence of primary Fab were used as negative controls.

Distal protection devices were obtained from 24 patients undergoing clinically indicated coronary and peripheral procedures. At the end of the procedure, the recovered filters from the distal protection devices were placed in ice-cold phosphate buffered solution containing EDTA/BHT (4 µM/20 µM). The filter bottom was cut off, the filter inverted and the material was paraffin embedded en bloc. Filters were chosen that had visible (yellow/white) material at bottom of filter. Seven µm serial sections were prepared, rehydrated, and immunostained with antibodies LA25 and LA24. The collection of materials was approved by the UCSD Human Research Subjects Protection Program.

Radiolabeling of Fab LA25 and non-specific isotype control Fab LA24. Modification of LA24 and LA25 for labeling with $^{89}$Zr was carried. Briefly, to a solution of LA24 or LA25 Fab (1-2 mg/ml) in 0.1 M carbonate buffer, pH 8.7-8.9, was added p-isothiocyanatobenzyl-desferrioxamine (Macrocyclics, Plano, Tex.; 5 mg/ml in DMSO) until a 2:1 mol ratio was achieved. The mixture was reacted at 37° C. for 2 h, then allowed to cool down to room temperature. The DFO-modified Fab was purified by centrifugal filtration using 10 kDa molecular weight cut-off (MWCO) filter tubes and washing twice with ample fresh PBS to prevent excessive concentration. For radiolabeling, the DFO-bearing Fabs were reacted with [$^{89}$Zr] Zirconium (IV) oxalate in PBS pH 7.1-7.4 for 2 h. After cooling down, the radiolabeled Fabs were purified by gel filtration using PD-10 columns and PBS as eluent. The radiochemical yield was 86±9% (n=5), and the radiochemical purity 96±9% (n=5), as assessed by size exclusion chromatography. The specific activities were 2.7±0.1 mCi/mg (n=2) and 3.8±0.4 mCi/mg (n=3) for $^{89}$Zr-LA24 or $^{89}$Zr-LA25, respectively.

Pharmacokinetics and biodistribution of $^{89}$Zr-LA24 and $^{89}$Zr-LA25 in mice. Pharmacokinetic profile and biodistribution evaluation of the PET tracer $^{89}$Zr-LA25 was carried out in Apoe mice (n=13, mean weight 30.8±6.8 g), using $^{89}$Zr-LA24 as chemical control. Radioactivity half-life was determined in blood after lateral tail-vein injection. Animals were injected with $^{89}$Zr-LA25 or $^{89}$Zr-LA24 (23±1 µCi, 6-8 µg). Blood was drawn from the tail vein at 1, 30, 60, 120, 180, and 240 minutes after injection. Blood was weighted and counted using a Wizard$^2$ 2480 automatic gamma counter (Perkin Elmer, Waltham, MA). At 4 hours after injection, all mice were sacrificed using an overdose of Isofluorane (Baxter, Deerfield, IL) and perfused through the heart with 20 ml saline. The following organs were harvested: brain, heart, lung, spleen, liver, kidneys, skeletal muscle and bone were harvested and weighted before counting using a Wizard$^2$ 2480 automatic gamma counter. Radioactivity concentration in tissues was calculated as percentage of injected dose per gram (% ID/g).

Immunofluorescence of mouse aortic roots. Aortic mouse roots were harvested 4 hours after injection, put in optimal cutting temperature (OCT) and cut in 7 µm thick sections. The first slide was subjected to autoradiography, while adjacent sections were stained for cell nuclei (DAPI, blue), macrophages (CD68, red) and endothelial cells (CD31, green). All antibodies for immunofluorescence staining were ordered from Bio-Rad, Herculus, CA, USA.

Immunostaining of mouse and rabbit livers. Rabbit and mouse livers were harvested and put in formalin before re-embedding in paraffin <72 hours after harvest. Animal liver specimens were subsequently stained according to the same protocol as described for human specimen.

PET/MR imaging. Rabbits (n=12, mean weights: 3.4±0.9 kg for rabbits with atherosclerosis, and 3.2±0.1 kg for healthy control rabbits). A 24G-catheter was introduced in the marginal ear vein for injection with either $^{83}$Zr-LA25 or $^{83}$Zr-LA24 (0.94±0.22 mCi, 0.3-0.4 mg). In the contralateral ear, a 22G-catheter was used for the administration of the gadolinium based contrast agent; gadopentetate dimeglumine (Magnevist, Bayer Healthcare). Anesthesia was induced by intramuscular injection of Ketamine (20 mg/kg) (Fort Dodge Animal Health, Overland Park, Kansas, USA), together with Xylazine (0.5 mg/kg) (Bayer, Shawnee Mission, Kansas, USA). All rabbits received a urine catheter to prevent any disruptions from signal in the bladder.

Rabbits were placed in a body matrix coil and received isoflurane anesthesia at 1.5% by inhalation and were oxygenated for the remaining of the PET/MR imaging experiment, while vital parameters were monitored. Shortly after injection, images were acquired in a dynamic fashion for the duration of 1 hour using a clinical 3 Tesla PET/MRI Biograph mMR (Siemens, Munchen, Germany). After scout scans, the PET scan was initiated and co-acquired with a radial VIBE MR sequence with the following imaging parameters: TR, 20 ms; TE, 1.89 ms; flip angle, 10 degrees; slice thickness, 1.1 mm$^3$. Attenuation correction of PET images was done using the built-in MR-based attenuation correction (MR-AC) map and images reconstructed using the OP-OSEM algorithm. In addition, a time-of-flight (TOF) non-contrast enhanced angiography was performed for localization of arterial anatomical landmarks (renal arteries and iliac bifurcation). Imaging parameters were: TR, 1600 ms; TE, 118 ms; flip angle, 140 degrees; ETL, 83; slice thickness, 0.6 mm.

A dynamic contrast-enhanced MRI (DCE-MRI) scan was performed. Black blood was obtained using a double inversion recovery (DIR) technique. A 3D turbo field echo (TFE) sequence with motion sensitized driven equilibrium (MSDE) preparation for black blood imaging was used to quantify the uptake of a FDA approved gadolinium based CA; gadopentetate diemglumine (Magnevist, Bayer Healthcare) from the right renal artery to the iliac bifurcation. Imaging parameters were: TR, 6.2 ms; TE, 2.8 ms; flip angle, 20 degrees; ETL, 80; spatial resolution, 0.6 mm$^3$; FOV, 160 mm$^2$; 20 slices; orientation, sagittal. This sequence was used before and 10 minutes after CA injection to quantify the CA accumulation in the vessel wall and thus to measure the permeability of the vessel wall. Before and during CA injection, the same sequence was used with 3 signal averages (time resolution 32s) to perform 3D DCE-MRI, and quantify the rate of uptake of CA in the vessel wall. The next day, 24±1.5 hours after injection, all rabbits received a 20 minutes static PET-scan, again using a TOF and MR-AC.

Pharmacokinetics and biodistribution $^{89}$Zr-LA25 or $^{89}$Zr-LA24 in rabbits. Radioactivity half-lives were determined by drawing blood from the ear arteries at 1 and 30 minutes, and at 1, 2, 4, 20, 24 and at sacrifice after 28 hours. All rabbits were sacrificed by an i.v. injected overdose of 100 mg/kg sodium pentobarbital and subsequently perfused with 500 ml saline. After sacrifice, all animals were perfused to make sure no blood or blood clots remained in the aorta and other organs before excision. Aortas were excised and divided in thoracic, form the aortic root until the diaphragm and the abdominal aorta, infra-diaphragmatic until iliac bifurcation, the latter with celiac trunk and renal arteries attached, serving as landmarks. The following organs were harvested: heart, lungs, liver, spleen, kidneys, one adrenal gland, muscle and bone-marrow and were weighted. All tissues were weighted before counting with a Wizard2 2480 automatic gamma counter. Radioactivity concentration in tissues was calculated as percentage of injected dose per gram (% ID/g).

Near-infrared fluorescence imaging. Twenty-four hours before sacrifice, all rabbits received fluorescently labeled high-density lipoprotein (Cy5.5-HDL, ~1 mg dye per rabbit) in 5 ml PBS solution via the marginal ear vein. After sacrifice all aortas, thoracic and abdominal, were placed on thick black paper and imaged with a Xenogen IVIS-200 optical imaging system (Perkin Elmer, Waltham, Mass.). Fluorescence images were acquired with excitation and emission wavelengths of 680 and 720 nm and a field of view (FOV) of 6.5 cm and 22.8 cm using different exposure times.

Autoradiography. Aortas were placed in a film cassette against a phosphorimaging plate (BASMS-2325, Fujifilm, Valhalla, N.Y.) for 48 h (mouse aortas, rabbit organs) or 72 h (rabbit aortas) at −20° C. to determine radiotracer distribution. Luminal autoradiography was performed for 96 h, after one of the harvested aortas was cut into 20 µm thick sections. Phosphorimaging plates were read at a pixel resolution of 25 µm with a Typhoon 7000IP plate reader (GE Healthcare, Pittsburgh, Pa.).

Image analysis. Image analysis for PET-imaging was performed after all data were processed and divided in different time frames using a custom-made program written in Matlab (Mathworks, Natick, Mass.). All data was subsequently processed using OsiriX Imaging Software (OsiriX Foundation, Geneva, Switzerland) by drawing regions of interest (ROIs) on the infrarenal abdominal aorta, and major organs (liver, spleen and kidneys). By averaging all acquired ROIs per organ (≥10 per organ), mean $SUV_{max}$ values in each tissue were obtained. All images acquired with DCE-MRI were reformatted in the axial plane for tracing. The vessel wall tracing was made on the average image of the dynamic series of DCE-MRI using Osirix software (OsiriX Foundation, Geneva, Switzerland). By drawing an inner and an outer vessel wall contour and computing the difference between these two, the vessel wall area or Region of Interest (ROI) was measured.

The area under the normalized signal intensity curve (IAUC) was calculated after two minutes, serving as a time point for data analysis, with a custom-made program written in Matlab (Mathworks, Natick, MA). IAUC is a measure of contrast agent extravasation and uptake in the (atherosclerotic) vessel wall. IAUC was calculated on a pixel-by-pixel basis. MR signal intensity over time was normalized to vertebral muscle signal intensity before the injection of contrast agent. NIRF analysis was done using Living Image Software (Perkin Elmer, Waltham, MA). All thoracic and abdominal aortas were divided in 10 equal regions of interest and quantified as Total Radiant Efficiency in $[p/s]/[\mu W/cm^2]$.

Histological analysis and immunostaining of rabbit aortic sections. Sections of 0.5 cm from the excised abdominal aorta were placed in optimal cutting temperature (OCT) compound and were cut into 7 µm thick sections that were adjacent to the luminal autoradiography cut section. Sections were stained for hematoxylin and eosin, RAM-11 for macrophages or Oil red O for lipids (Dako, Santa Clara, CA). Detailed images were made with a Nikon Eclipse E400 microscope, a Nikon DS-LT' camera box, and a Nikon DS-5 M camera while whole luminal aorta images were made using an Olympus Stereoscope MVX10.

Statistics. Statistical analysis was conducted using unpaired t-tests. Linear regression was used for the correlative measures, computing Pearson's r coefficients to determine the degree of correlation. Data are reported as mean±standard deviation. P values of <0.05 were considered statistically significant. For the calculation of the different statistical parameters, Prism (version 6.0, GraphPad Software Inc., La Jolla, CA) was used.

Figure 1B:
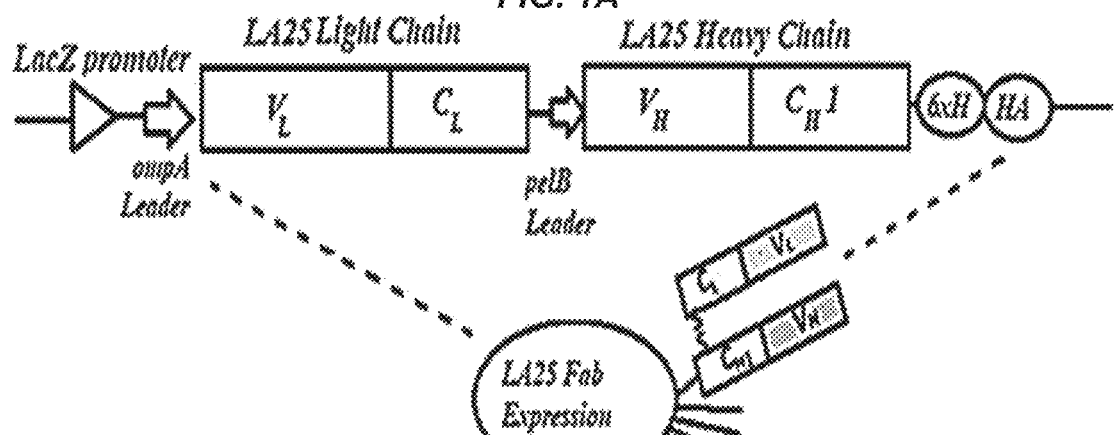

Cloning and characterization of LA25. LDL was modified with MAA, MDA or $CuSO_4$ to generate MAA-LDL (FIG. 1A), MDA-LDL or copper-oxidized LDL (Cu-OxLDL) respectively. MAA is a specific advanced MDA-type adduct that is an immunodominant MDA epitope. To enrich for antibodies, a Fab library was constructed (κ/λ) from lymphocytes isolated from umbilical cord blood of 7 newborns and screened these with MAA-BSA. After 4 rounds of panning with each library, an enrichment in the newborn library of fully or very near germline sequences was identified, consistent with minimal non-templated insertions in the CDR3 region (FIG. 1B). The resultant Fabs were cloned into the phagemid pComb3X and LA25 was identified as a leading candidate due to its specificity for MAA epitopes and optimal expression characteristics. LA24 was identified from the same library, but did not bind any relevant oxidation-specific epitopes present in vivo. LA25 and LA24 plasmids from selected Fab phage clones were codon optimized and transformed into E. coli C41 (DE3) for production of soluble Fab.

Figure 1C:
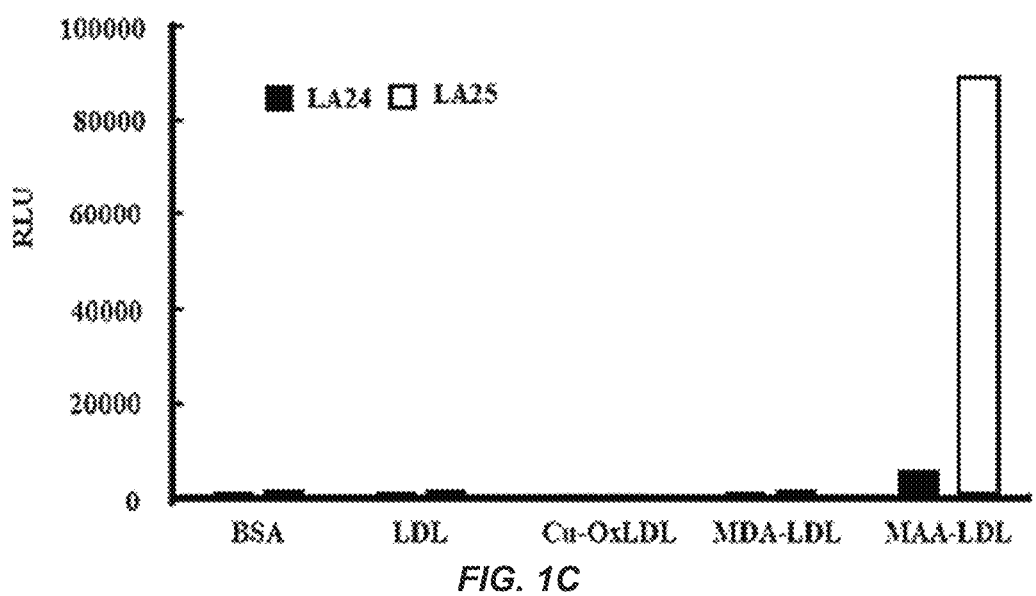
Figure 1D:
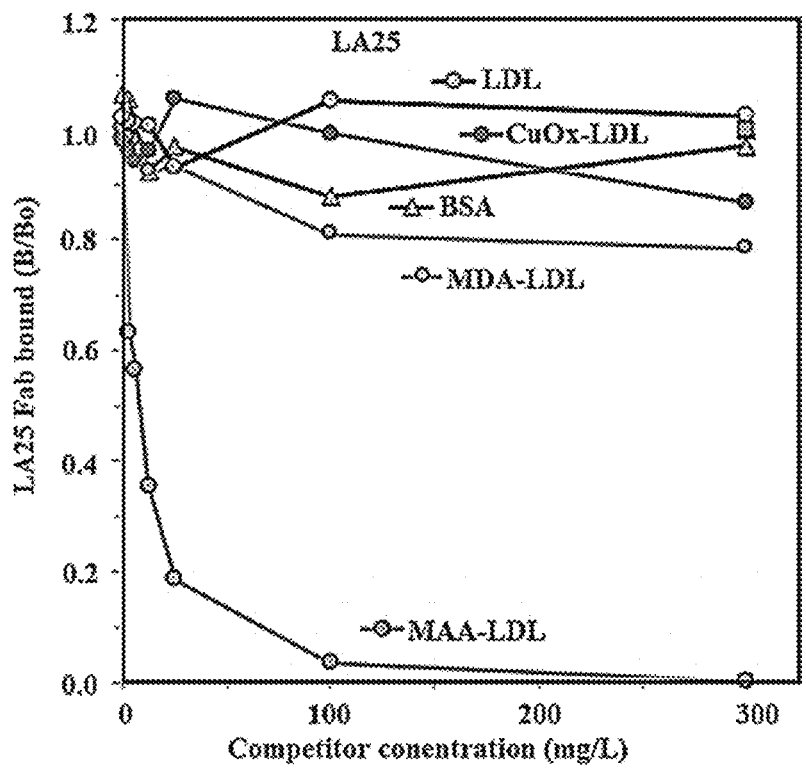
Figure 2:
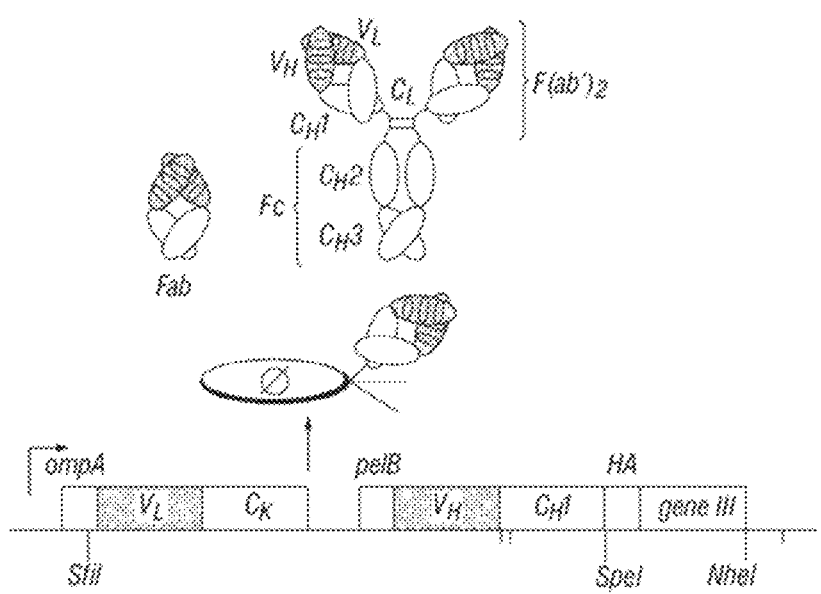
Figure 5:
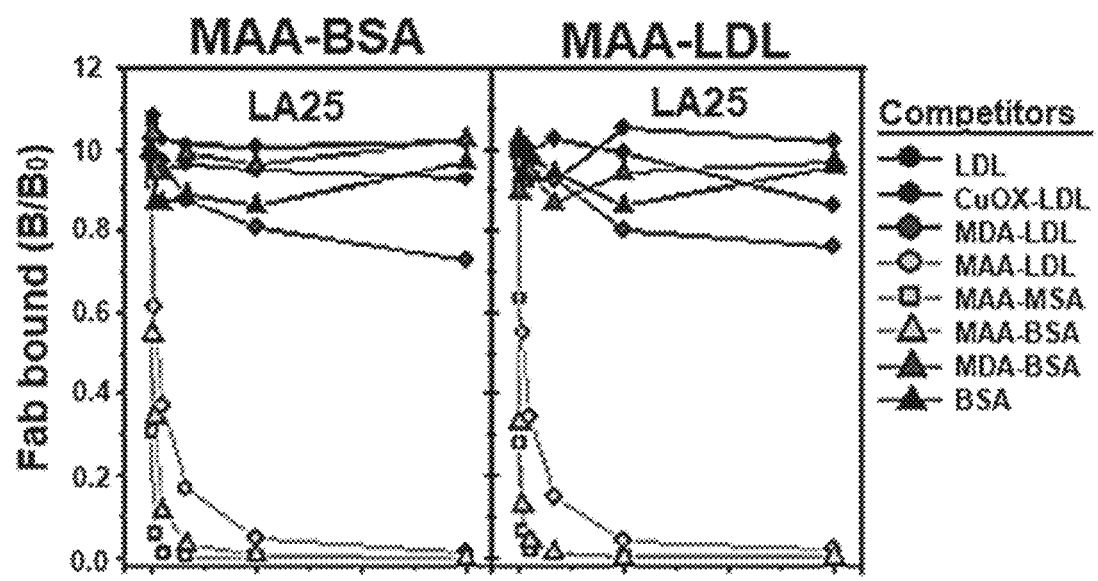
FIG. 5 shows MAA specificity of LA25 antibody.
Figure 6:
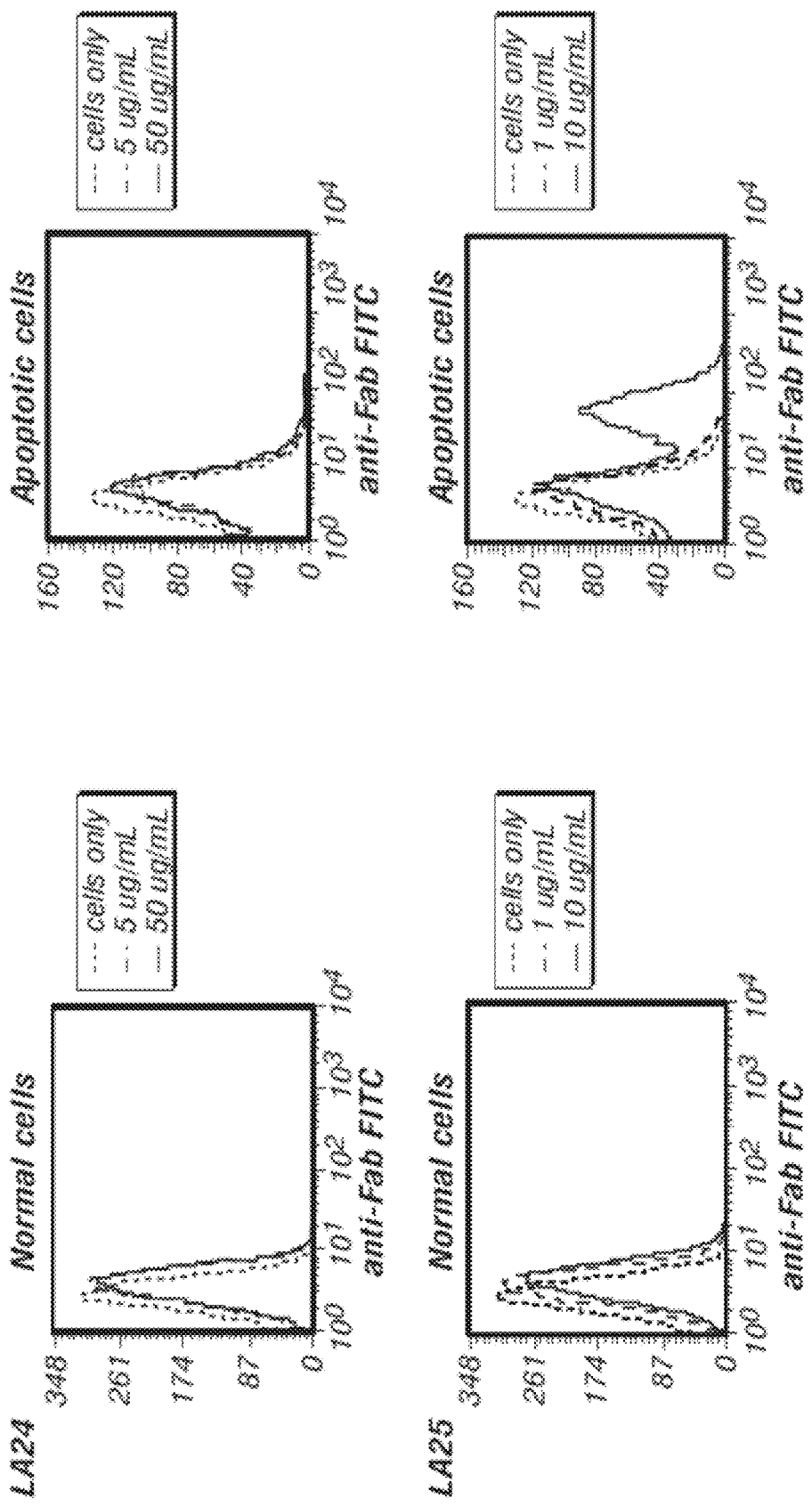
FIG. 6 shows the binding of LA25, KA2 and ML7 Fab to apoptotic cells, which was also confirmed by ELISA. Other panels show, e.g., LA25 does not bind normal cells, and that LA24 does not bind normal or apoptotic cells.
Figure 6:
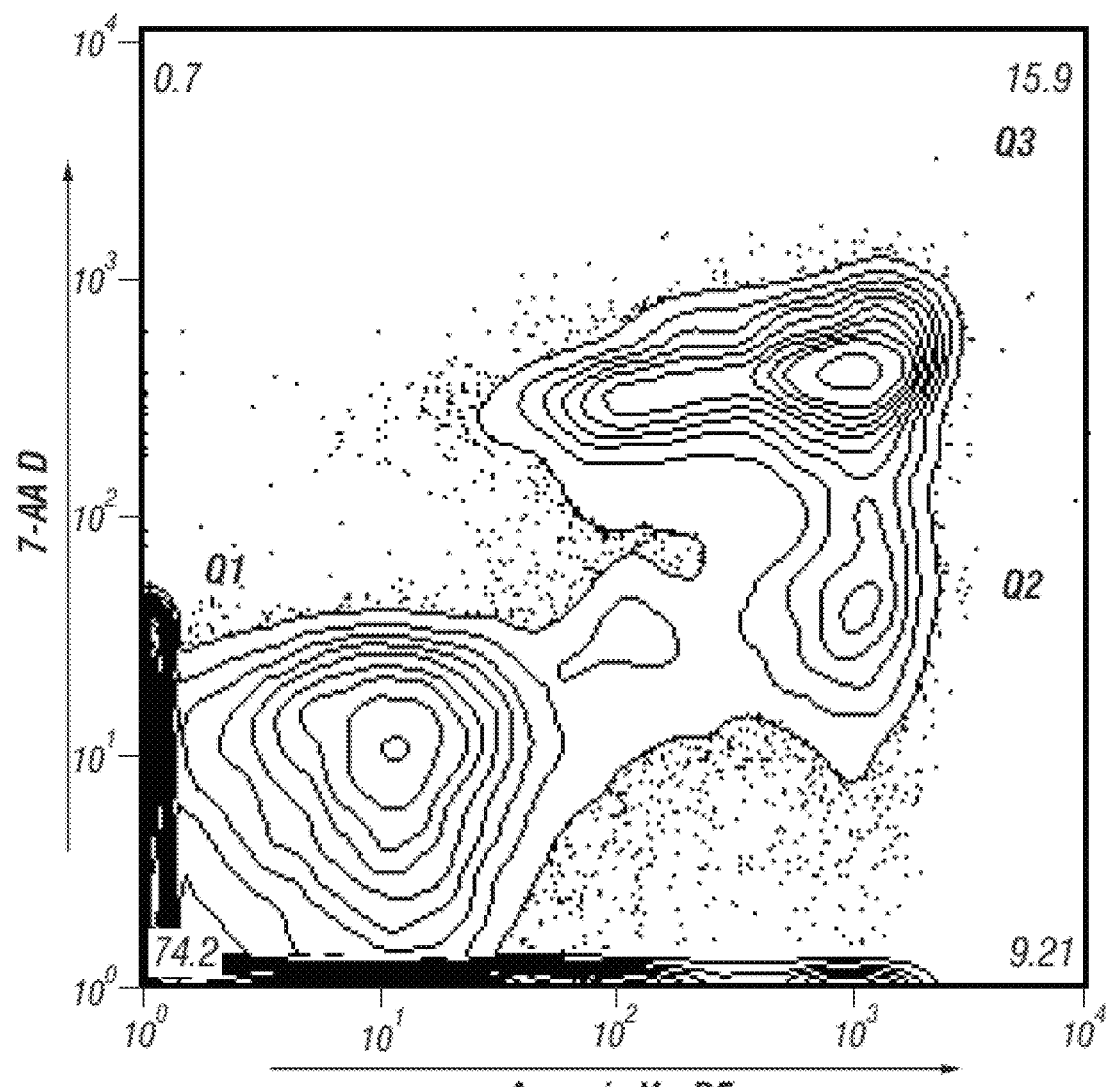
Figure 6:
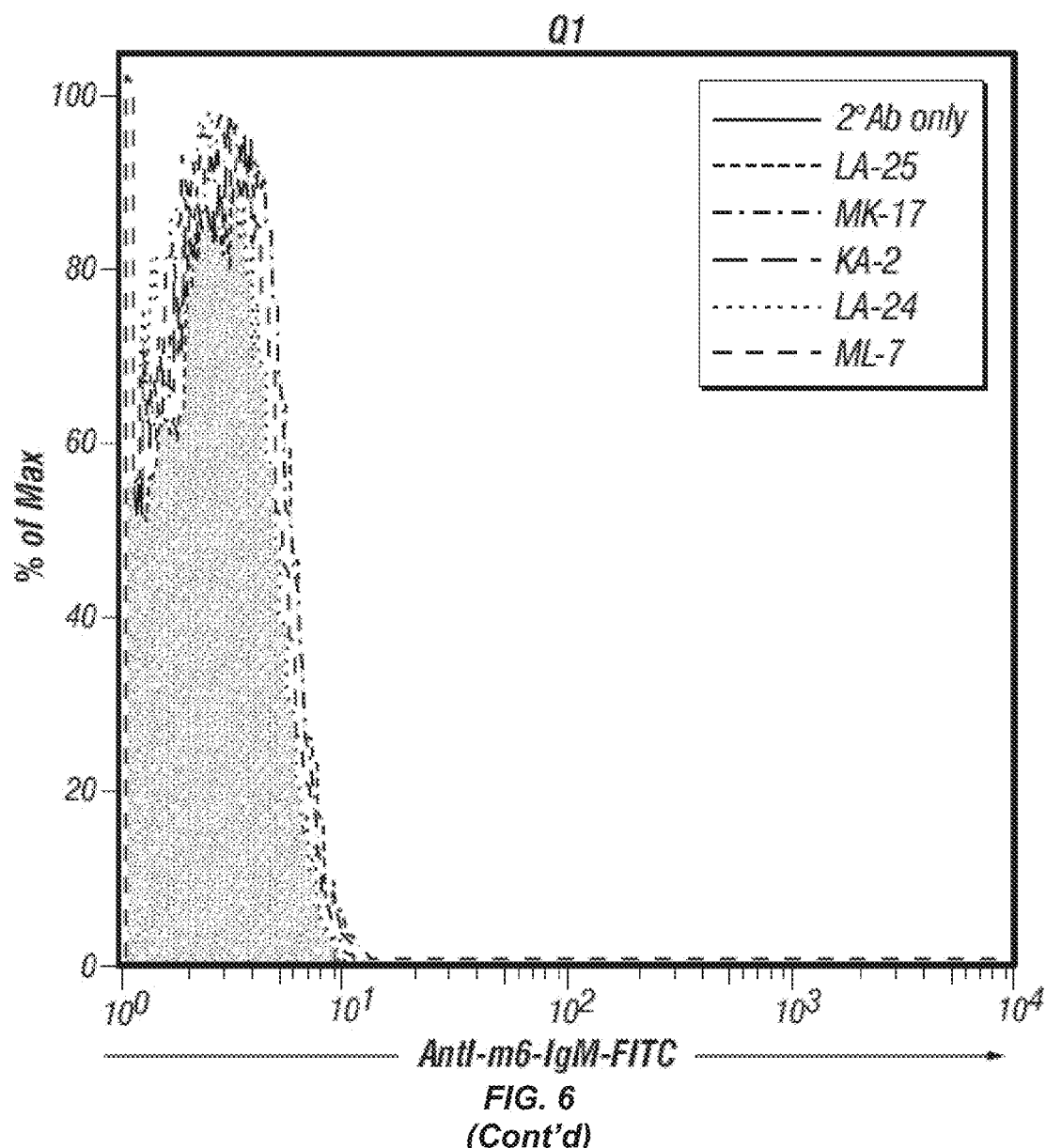
Figure 6:
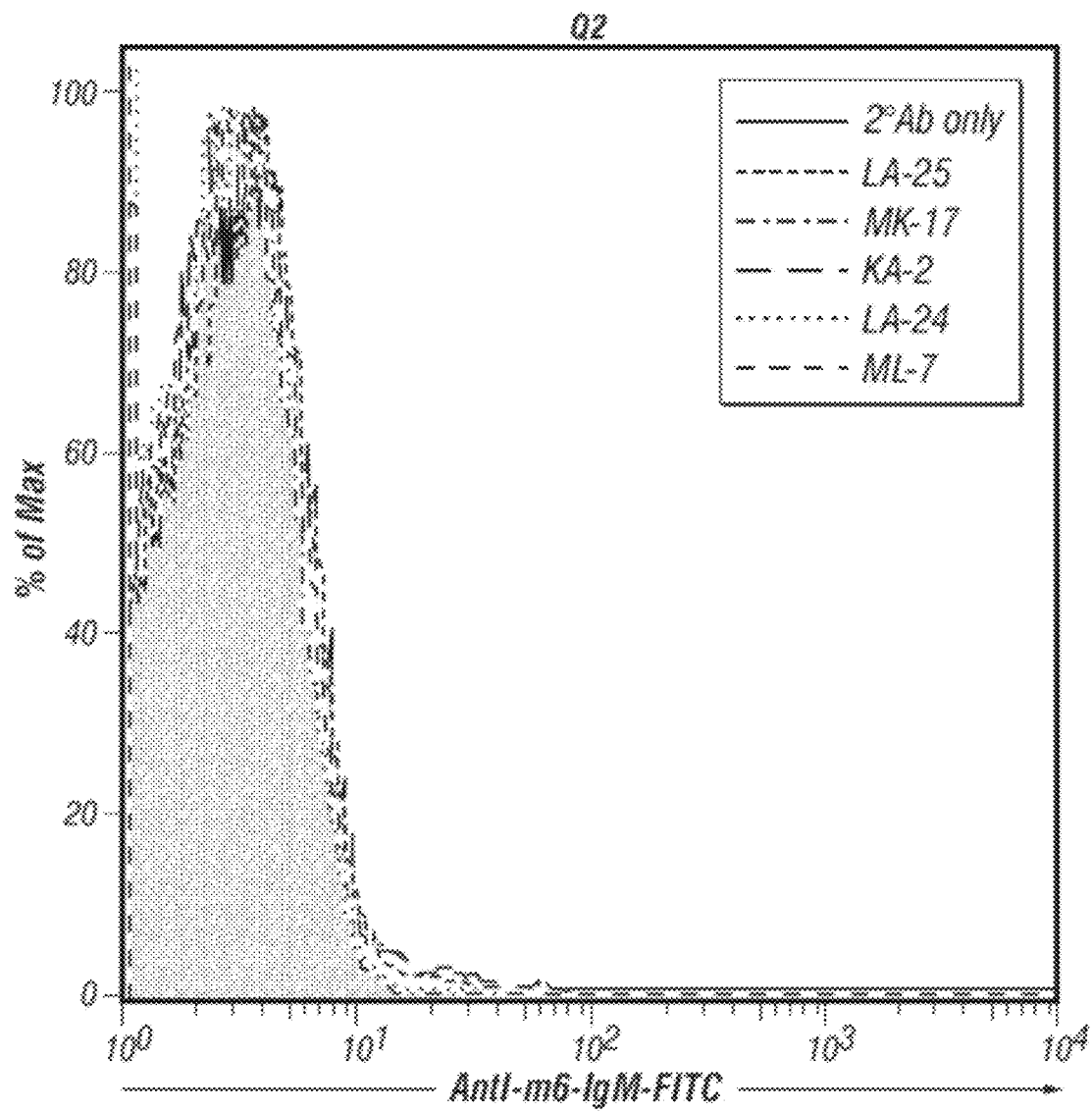
Figure 6:
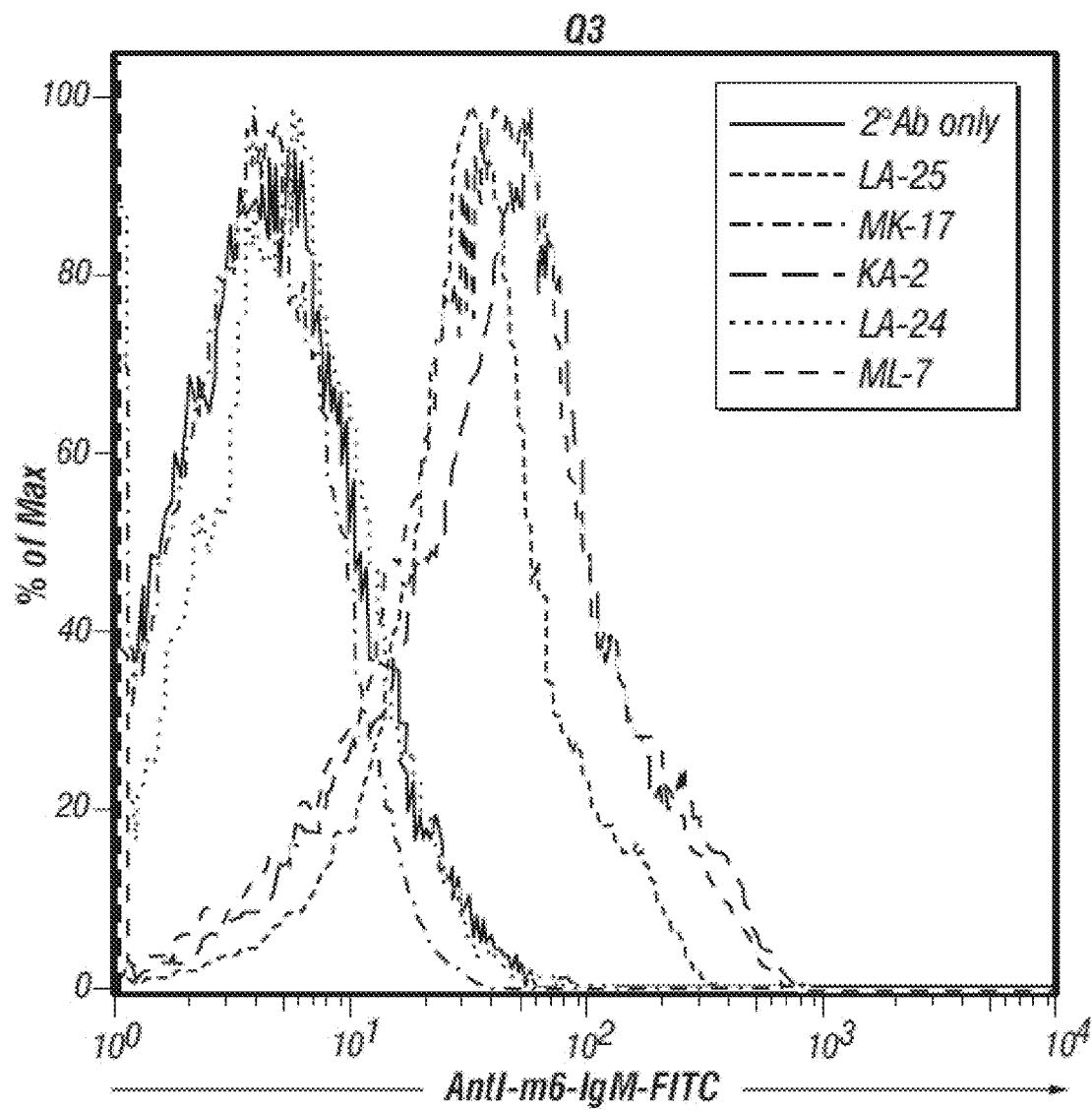
Figure 9:
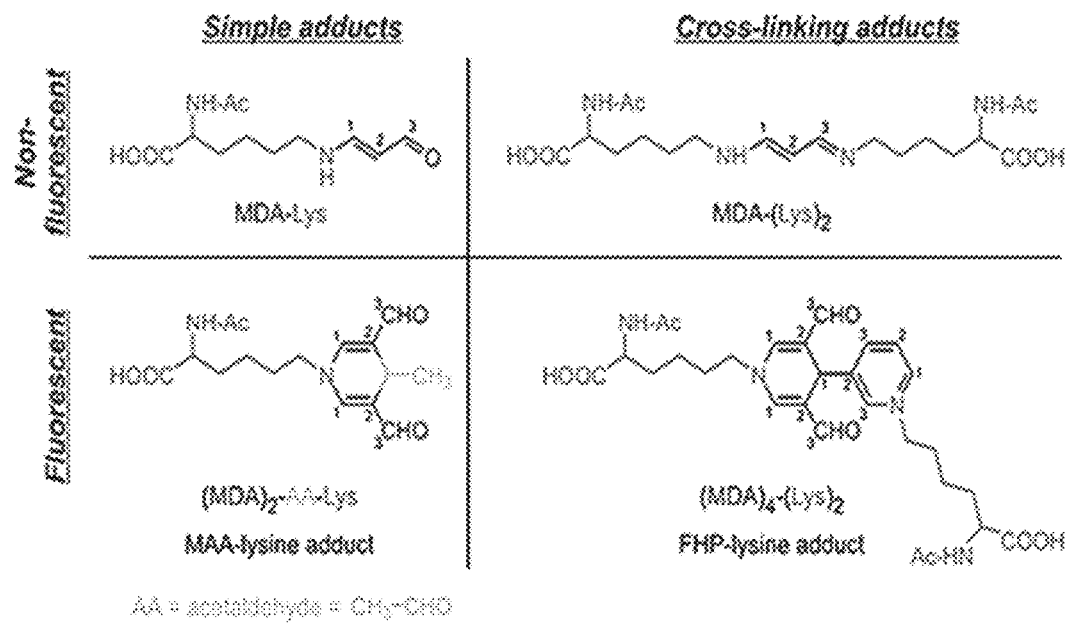
FIG. 9 provides a schematic illustration of MDA-lysine adducts.
Figure 10:
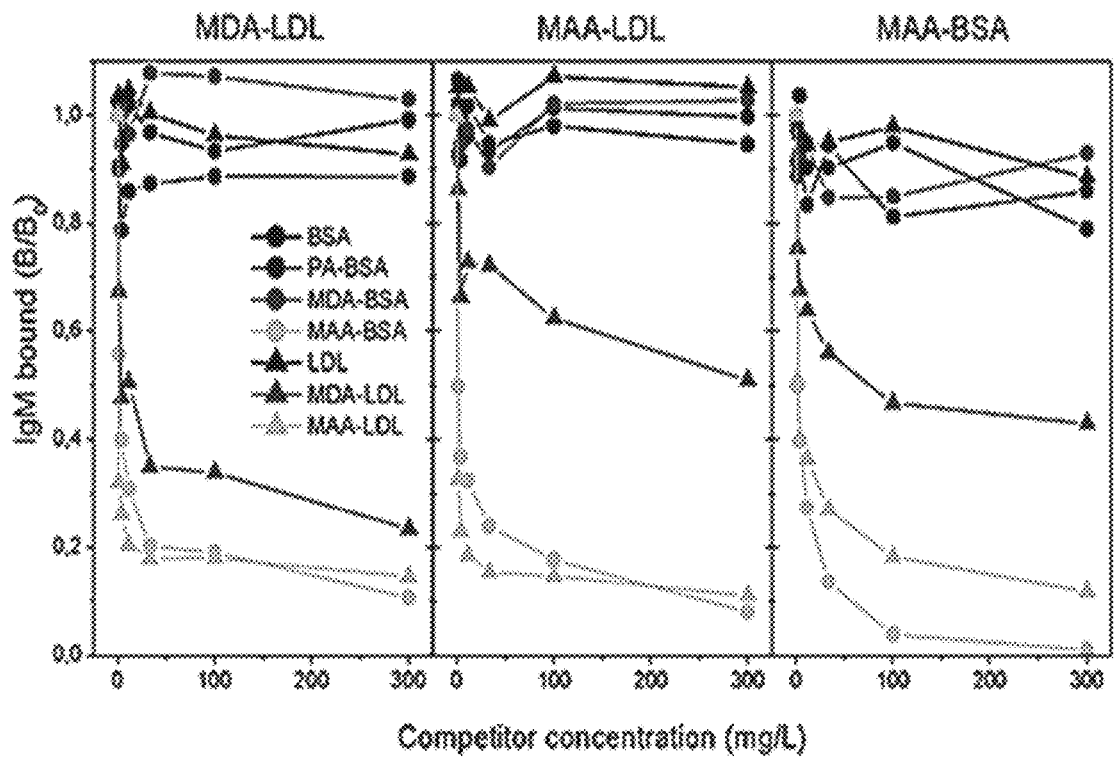
FIG. 10 presents competition by oxidation-specific antigens to the binding of pooled umbilical cord plasma IgM (n=7) to MDA-LDL, MAA-LDL, and MAA-BSA respectively.
Figure 11:
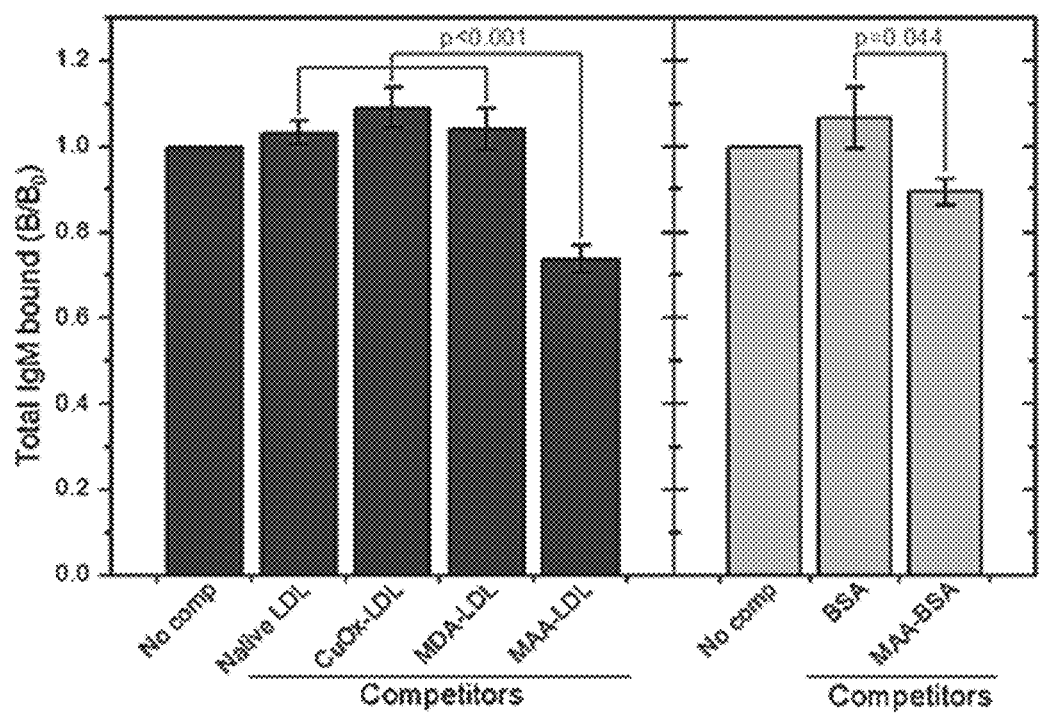
FIG. 11 demonstrates that complex MDA-derived epitopes are a major target for IgM in human newborn plasma. As shown, preabsorption of IgM in human umbilical cord plasma with oxidation-specific antigens shows that the MAA-derived adducts constitute a dominant target for natural antibodies (Nabs) in newborn babies. Data shown as mean±SEM (n=7 plasmas).
Figure 12:
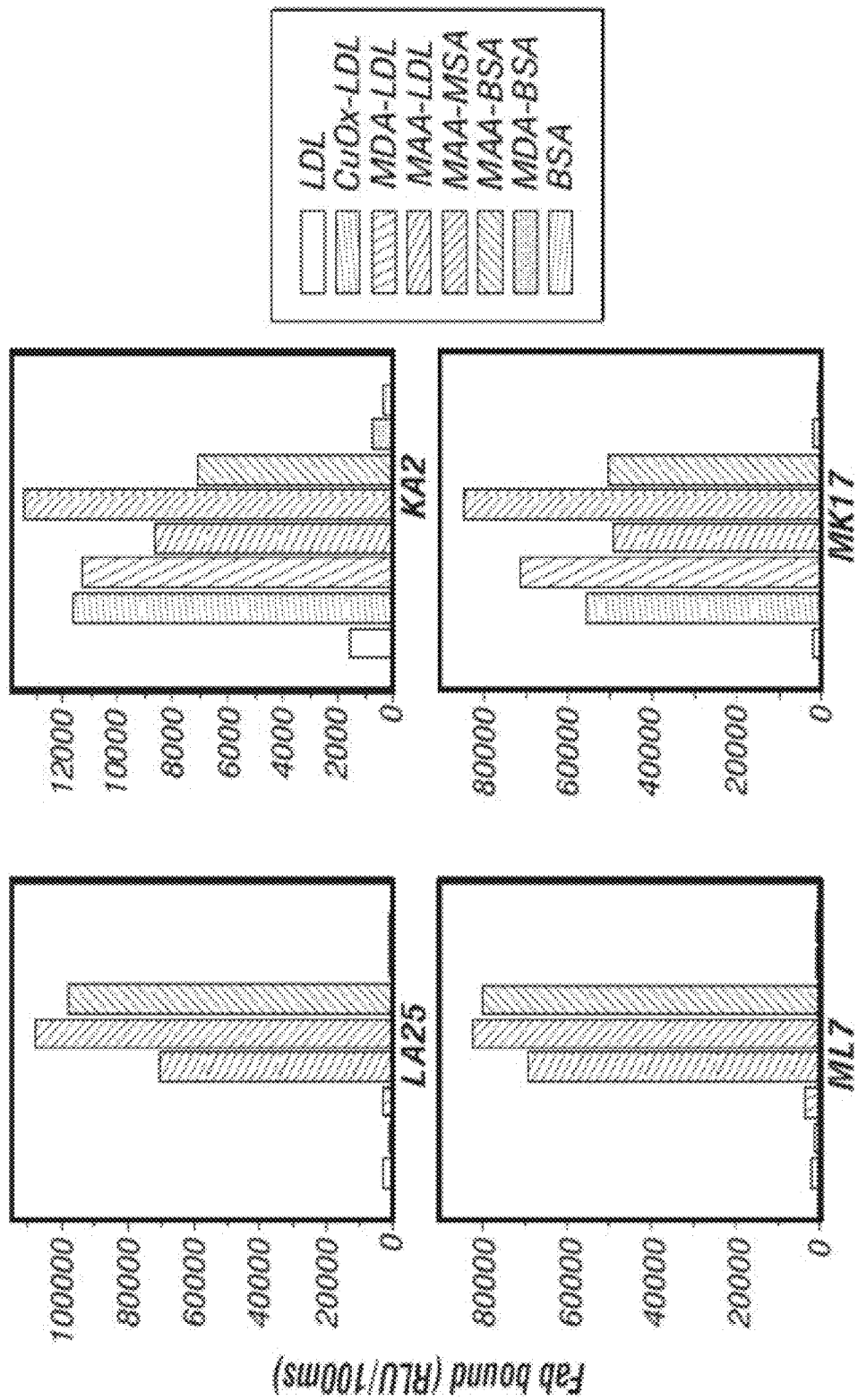
FIG. 12 demonstrates that human Fabs bind to different oxidation-specific epitopes in OxLDL. Antigen-profiling and competition ELISA revealed that LA24 is not hapten-specific in contrast to the other Fabs. LA25 and ML7 recognize a MAA-lysine epitope. KA2 and MK17 share binding specificity, but to different, though related, epitopes present in various OxLDL antigens.
Figure 13:
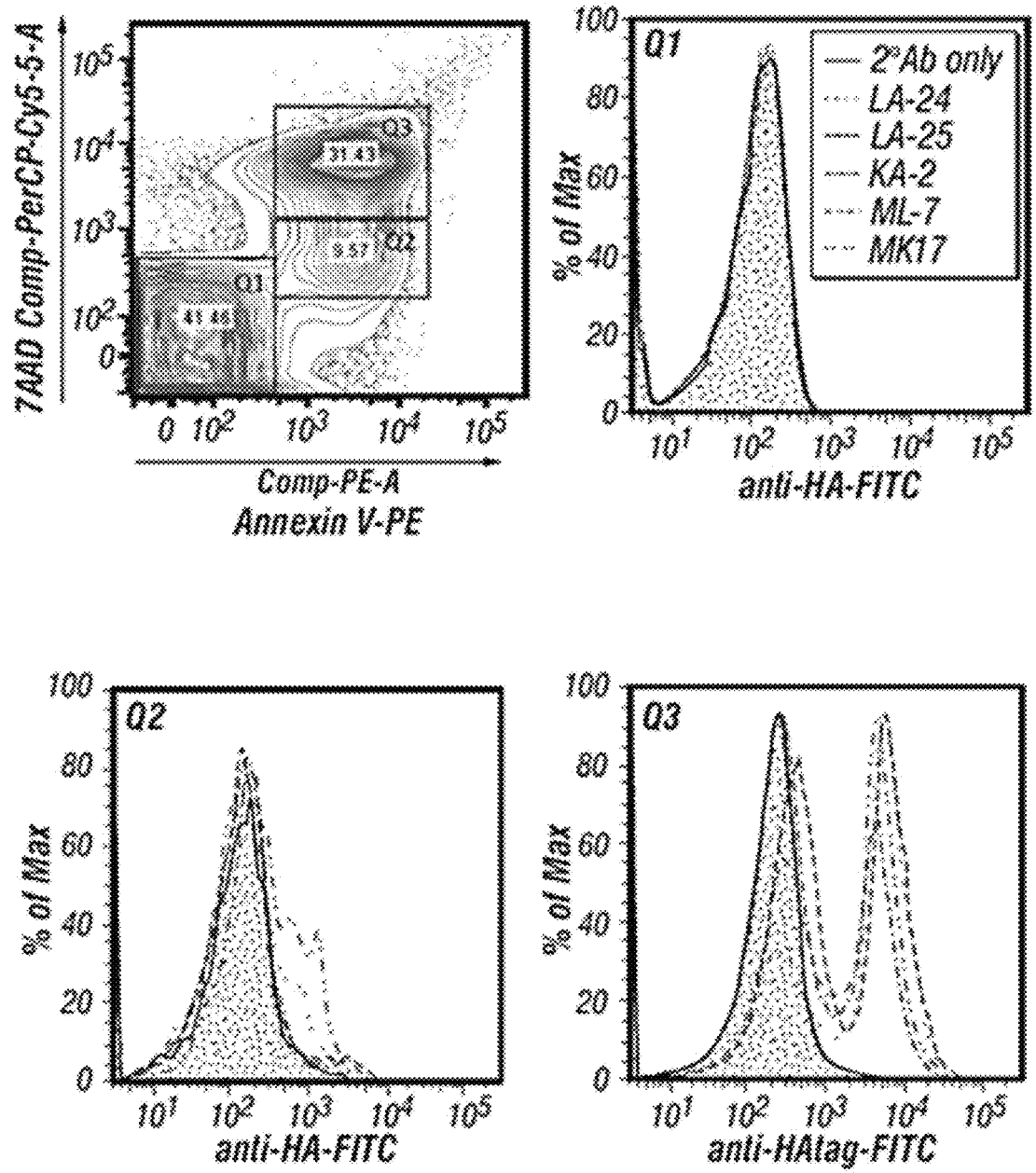
FIG. 13 demonstrates that hapten-specific Fabs (LA25, KA2, ML7, and MK17) bind to apoptotic cells and stain rabbit atherosclerotic lesions and inflamed human rheumatoid synovial tissue, suggesting the presence of 'complex' MDA-derived epitopes. As shown, Fab binding to apoptotic murine thymocytes by FACS.
Figure 14:
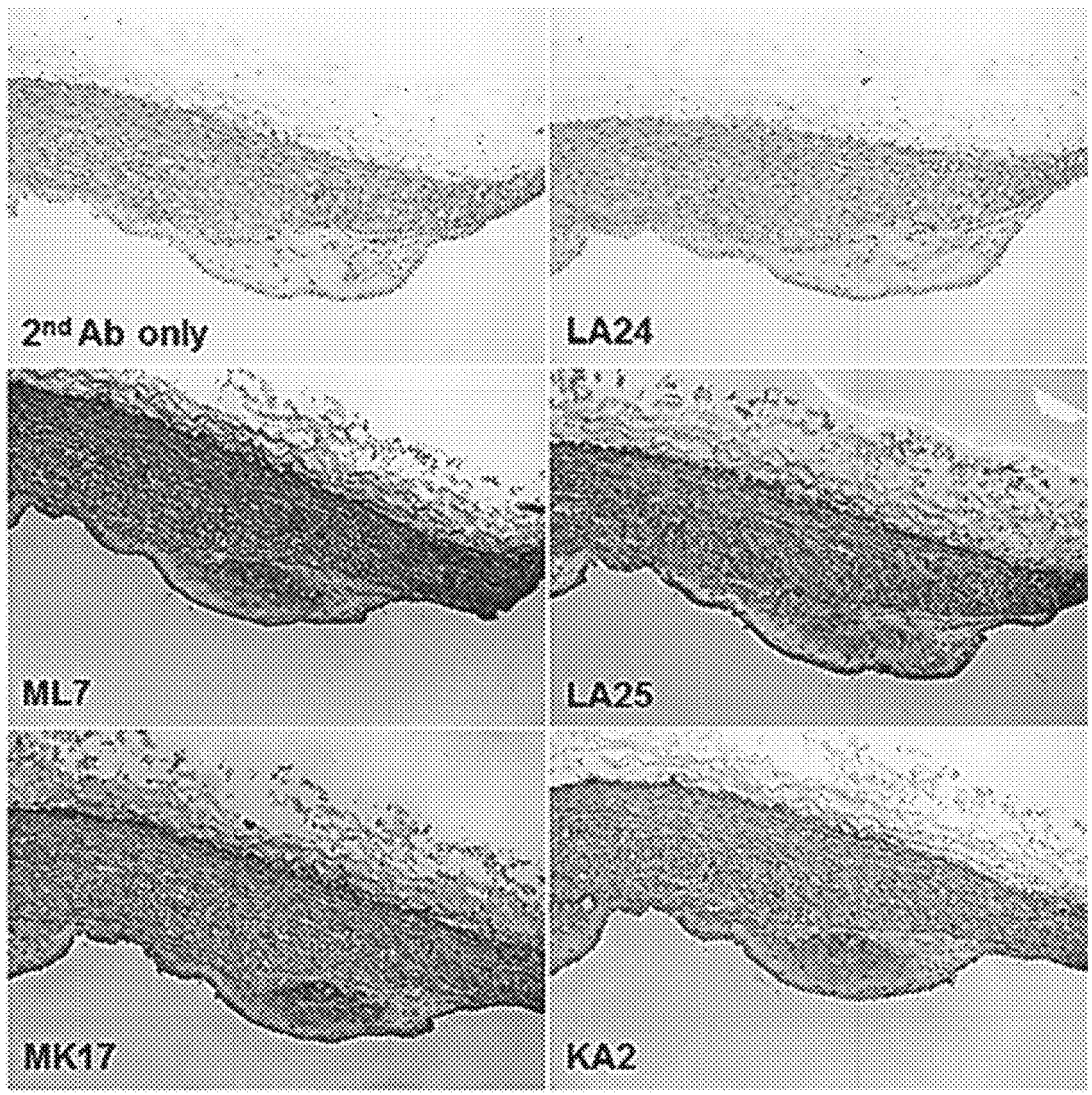
FIG. 14 presents immunostaining of frozen rabbit aorta. Human Fabs were visualized using biotinylated F(ab')$_2$ fragments of anti-huIgG [F(ab')$_2$-specific], ABC-AP VectaStain, and Vector RED substrate. Nuclei were counterstained using Hematoxylin.
Figure 15:
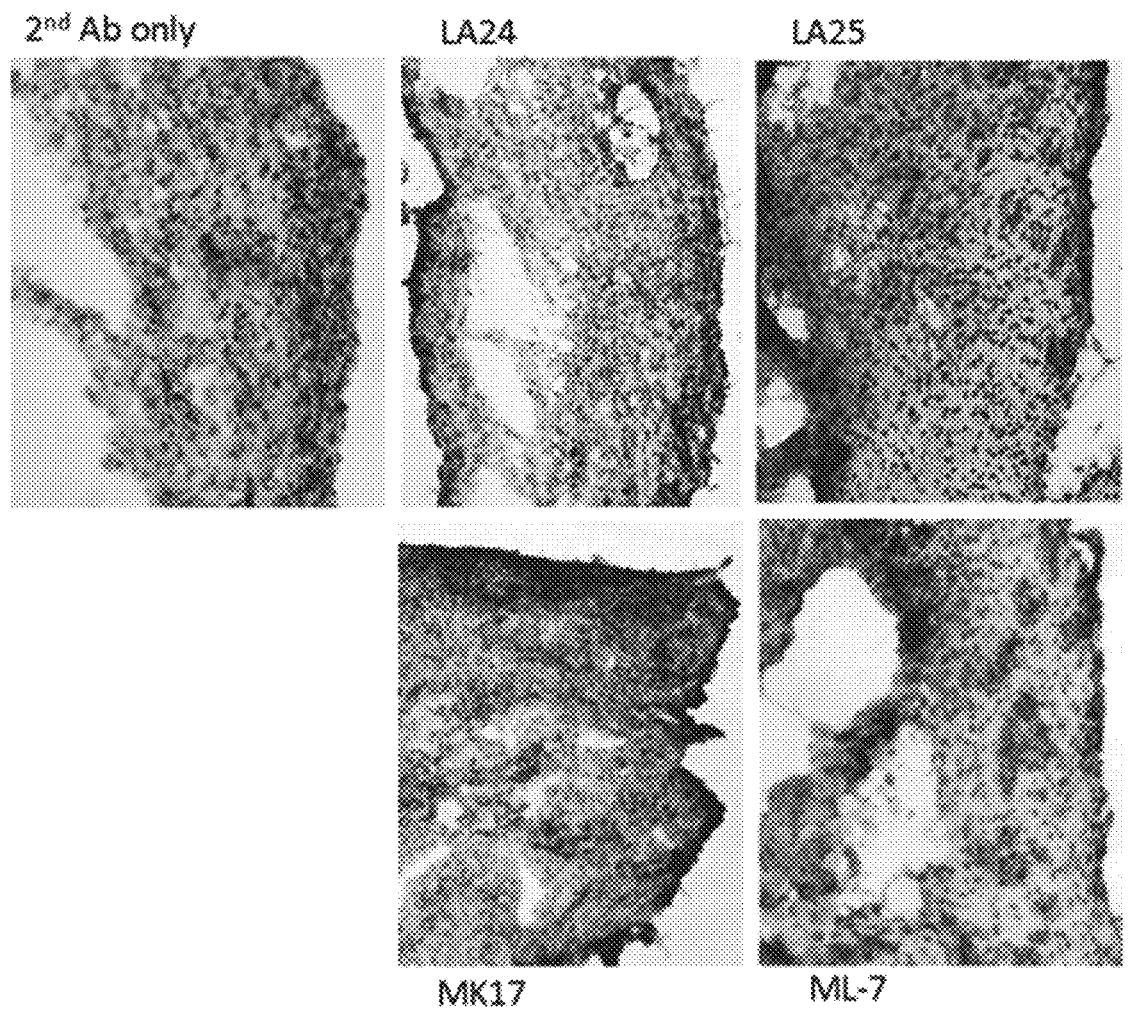
FIG. 15 presents immunostaining of oxidation-specific epitopes in human inflamed rheumatoid synovial tissue with Fabs of the disclosure. The human Fabs were visualized as described in FIG. 14, except an anti-HA-tag $2^{nd}$ Ab was used.
Figure 16:
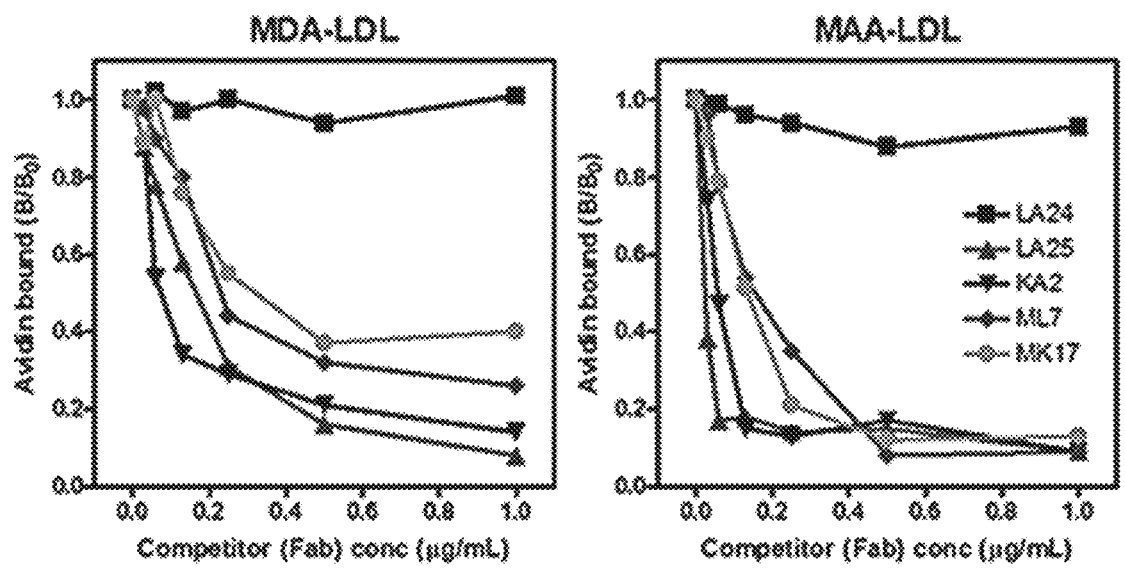
FIG. 16 demonstrates that the Fabs are specific for 'complex' MDA-derived epitopes compete for modified LDL binding to scavenger receptors of macrophages. As shown, Fab competition of biotinylated OxLDL ligand binding to J774 macrophages were assessed in a microtiter plate-based assay.
Figure 17:
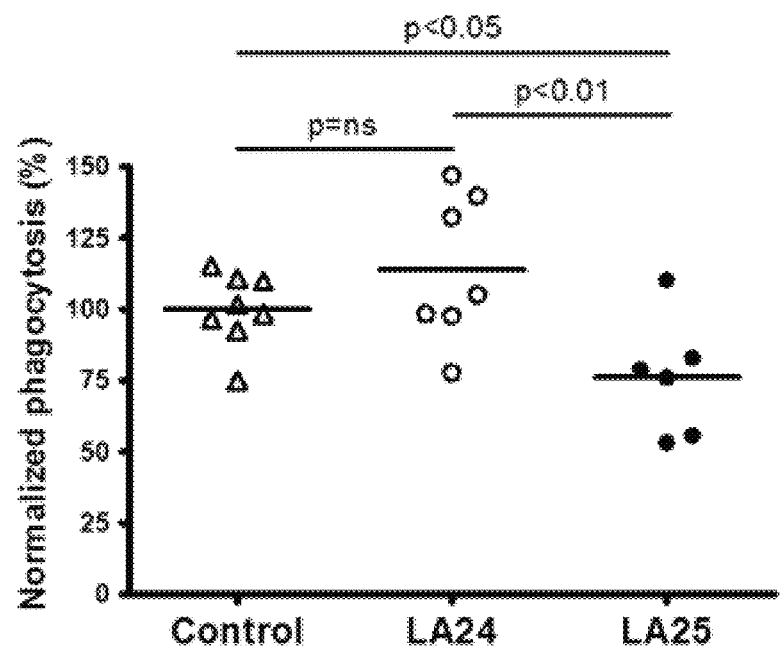
FIG. 17 demonstrates that LA25 inhibits in vivo-phagocytosis of apoptotic cells by macrophages. As shown, LA25, but not LA24, inhibits in vivo-phagocytosis of apoptotic murine thymocytes by elicited peritoneal macrophages in Rag1$^{-/-}$xLdlr$^{-/-}$ mice.
Figure 18:
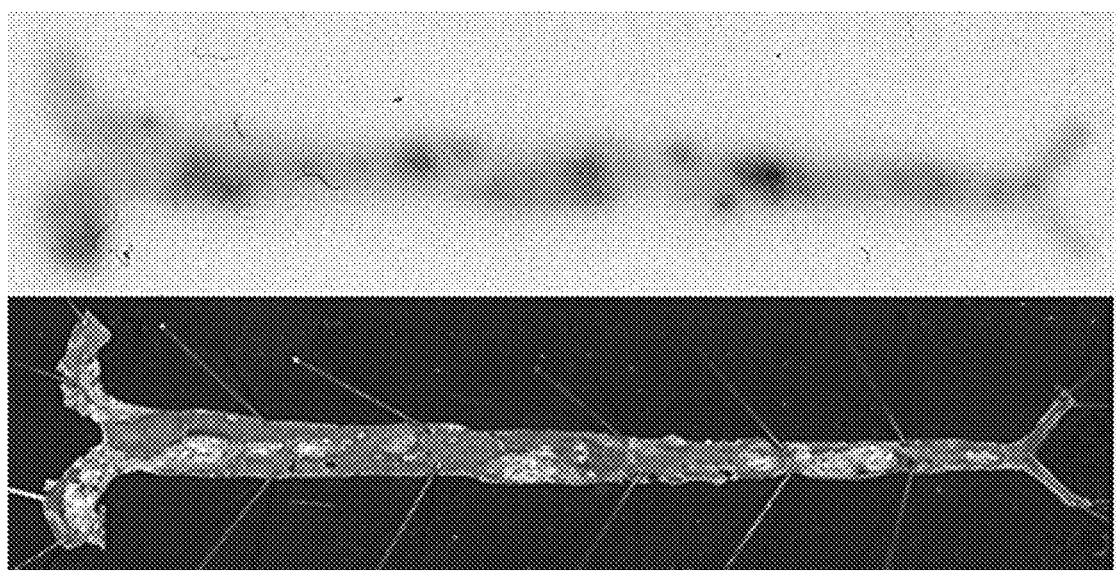
FIG. 18 demonstrates the in vivo aortic uptake of radio-labeled LA25. As shown, an en face preparation of a Sudan IV-stained aorta (bottom) and corresponding autoradiograph (top) from a male ApoE$^{-/-}$ mouse after tail vein injection of 10 mCi $^{125}$I-LA25.
Figure 19:
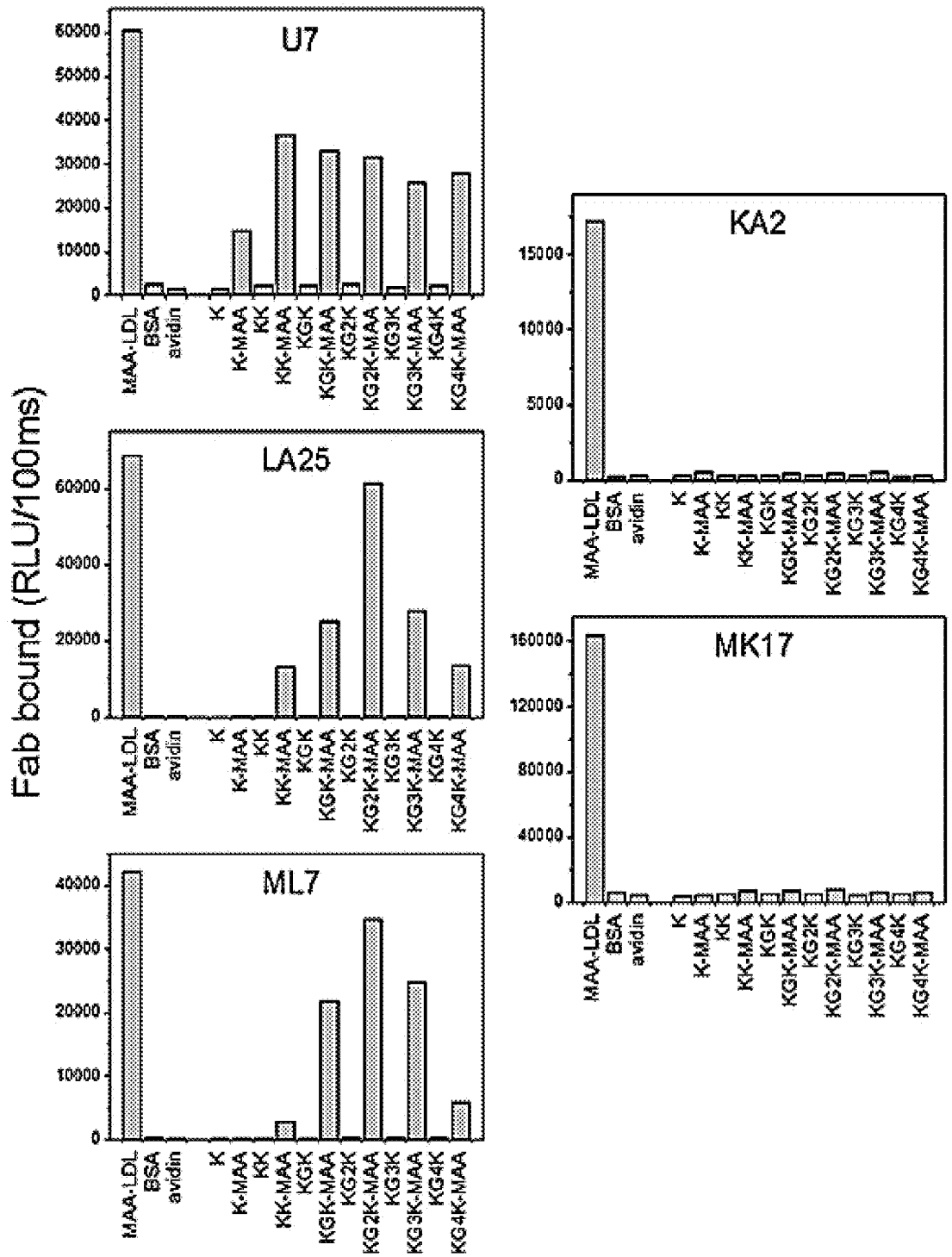
FIG. 19 demonstrates that antibodies of the disclosure bind to unique MAA-epitope. Various biotin modified peptides with different number of lysine residues defined by x were modified with MAA and bound to avidin-coated wells.

LA25 detected MAA-LDL, but did not detect LDL, Cu-OxLDL or MDA-LDL (FIG. 1C). LA24 did not detect any of these epitopes. To assess specificity for MAA-LDL, competition experiments were performed of LA25 binding to MAA-LDL, which demonstrated specific and near complete ability of MAA-LDL, but not other competitors, to compete LA25 binding (FIG. 1D).

Figure 20:
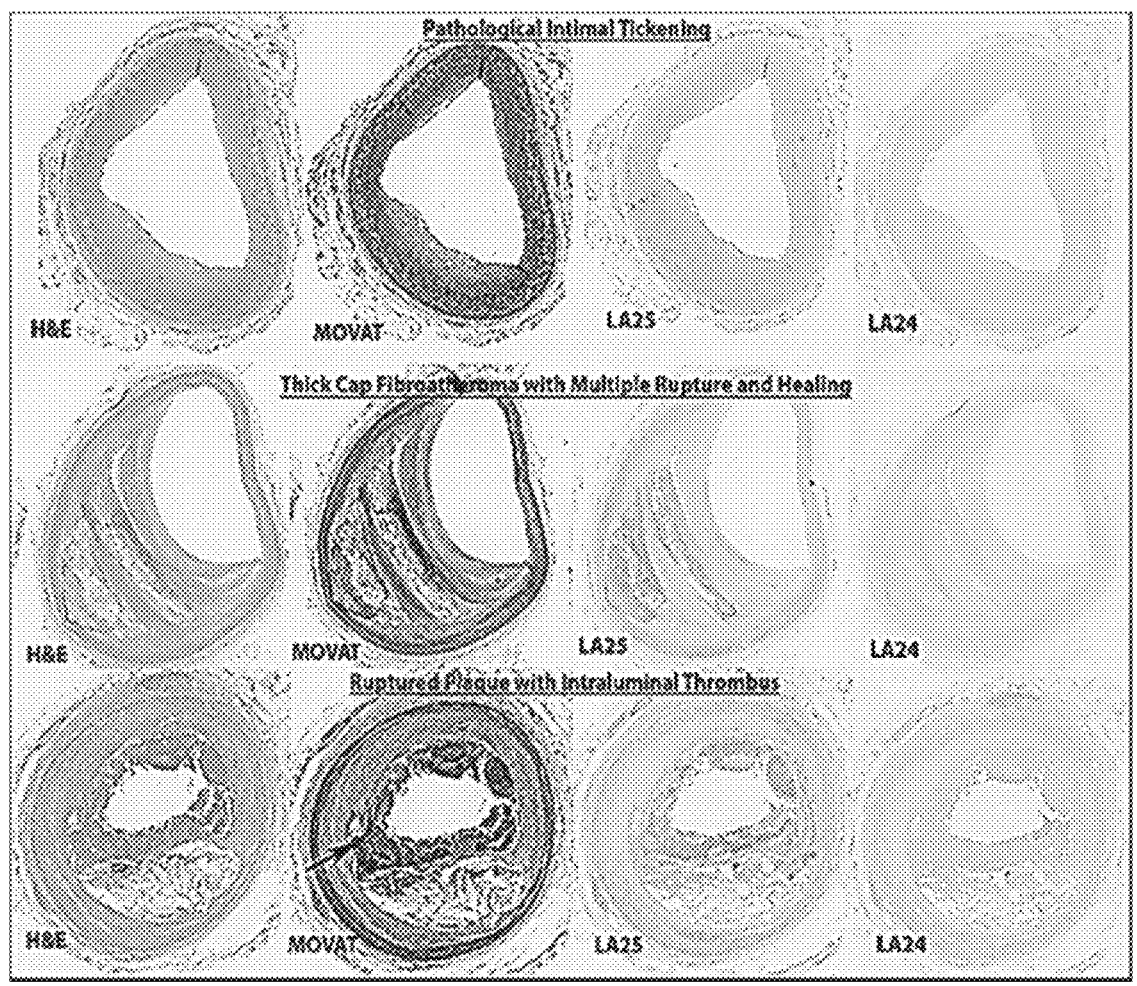
FIG. 20 shows immunostaining of an early fibroatheroma, a thick cap fibroatheroma with multiple rupture and healing and a ruptured plaque with LA25. The top row displays an early fibroatheroma, the middle row a complex thick cap fibroatheroma and bottom row a ruptured thin cap fibroatheroma stained with H&E, Movat pentachrome, LA25 and LA24 antibody control. Note the presence of thrombus in this section (arrow), which also stains with LA25.
Figure 21:
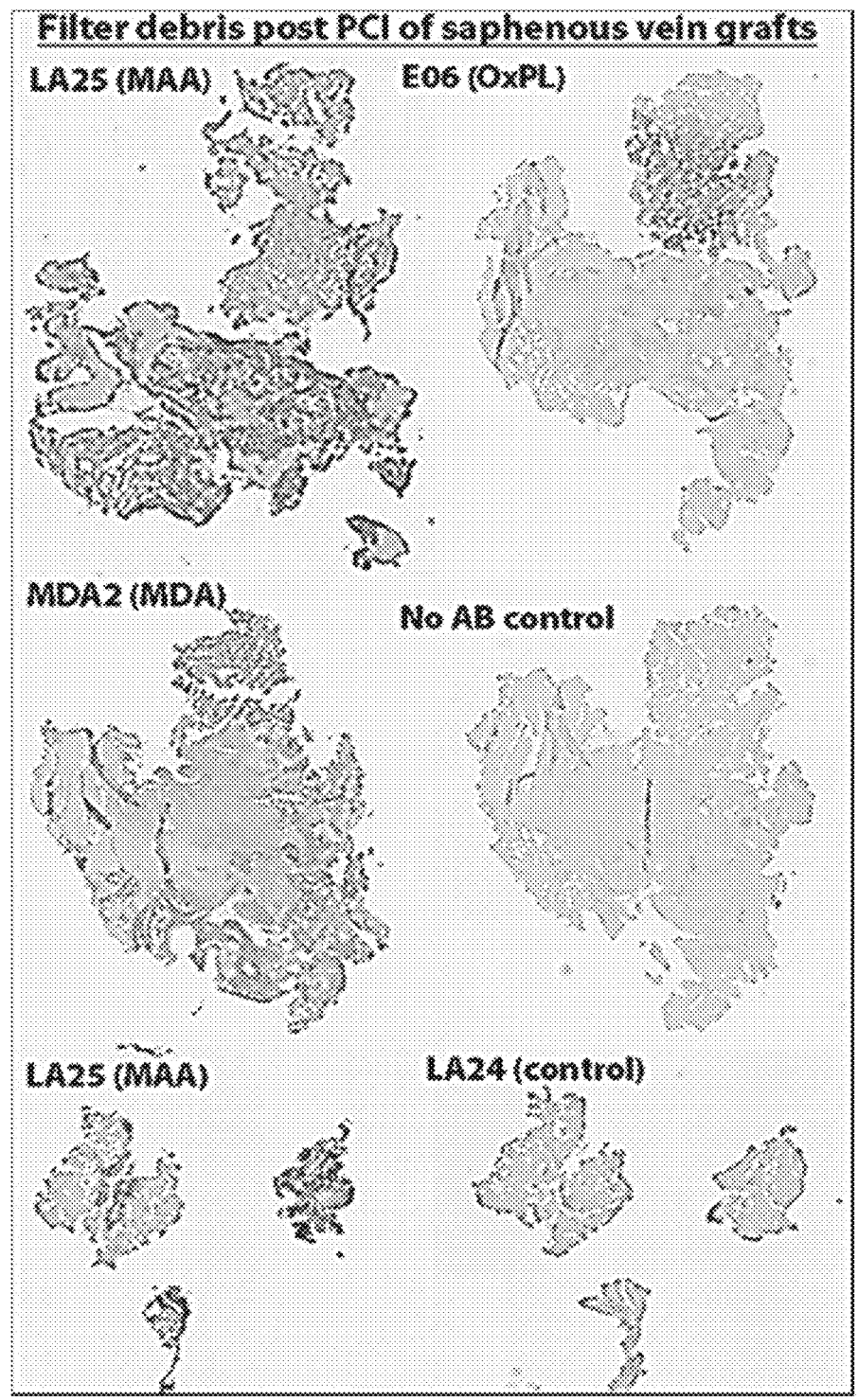
FIG. 21 shows immunostaining of LA25 in debris from distal protection devices. The bottom row displays serial sections of embolized plaque debris captured with a distal protection device following percutaneous coronary intervention of a stenotic 12-year old coronary saphenous vein graft in a patient with crescendo angina. The material is stained with LA25 for MAA epitopes, antibody MDA3 for MDA epitopes, antibody E06 for OxPL epitopes and a no-antibody control section. The material is stained with LA25 for MAA epitopes, antibody MDA3 for MDA epitopes, antibody E06 for OxPL epitopes and a LA24 antibody control.

Immunostaining of human advanced and ruptured plaques and debris from distal protection devices with LA25. Immunostaining of human advanced fibroatheromas and ruptured coronary plaques with LA25 showed specificity in the necrotic core (FIG. 20). Interestingly, LA25 also stained the thrombus adjacent to the plaque rupture. Thrombi are known to express MDA/MAA epitopes, likely through secretion by activated platelets. Debris from distal protection devices also stained strongly with LA25, as well as MDA and OxPL epitopes (FIG. 20). MAA epitopes did not co-localize with OxPL epitopes in these specimens, but MDA epitopes co-localized partially with both MAA and OxPL epitopes.

Pharmacokinetics, biodistribution and plaque specificity $^{89}$Zr-LA25 in mice. Initially, the $^{89}$Zr-labeled Fabs were tested in $Apoe^{-/-}$ mice (22 weeks on high-fat diet) to investigate their in vivo behavior and specificity for MAA epitopes in atherosclerotic plaques. Mice were intravenously injected with either $^{89}$Zr-LA25 or $^{89}$Zr-LA24, which was used as chemical control. The blood radioactivity half-lives were 29 and 13 minutes for LA25 and LA24 respectively, and blood radioactivity concentrations differed significantly starting from 30 minutes after injection (FIG. 22A).

Radioactivity distribution in selected tissues was determined by gamma counting at 4 hours post injection (p.i.). Aortic uptake was significantly higher in mice injected with $^{89}$Zr-LA25 compared with $^{89}$Zr-LA24, 1.56±0.35 vs. 0.41±0.13% ID/g, P<0.0001 (FIG. 22B). Representative autoradiographs of mouse aortas showed homogenous radioactivity distribution in those injected with $^{89}$Zr-LA24 compared with $^{89}$Zr-LA25, which showed a heterogeneous pattern of uptake with more intense depositions at the level of typical lesion sites such as the aortic root and the abdominal aorta (indicated by arrows, FIG. 22C).

A high kidney accumulation was found in all mice, indicative of renal clearance (FIG. 22D). Despite the higher renal uptake for $^{89}$Zr-LA24, the difference between the two groups was not statistically significant, 85.5±20.0 vs. 64.2±16.3, P=0.06. Furthermore, uptake in liver and spleen was significantly lower in mice injected with $^{89}$Zr-LA24 compared to $^{89}$Zr-LA25, 0.53±0.12 vs. 3.50±1.67% injected dose/gram tissue (% ID/g), P=0.0006, and 0.63±0.16 vs. 2.69±1.03% ID/g, P=0.0003, respectively.

Dynamic PET/MR imaging with ex vivo confirmation. Atherosclerotic rabbits were dynamically scanned for one hour immediately after intravenous injection of either $^{89}$Zr-LA25 or $^{89}$Zr-LA24 (FIG. 23A top and bottom, respectively). Standardized uptake values (SUV) were measured in kidney, liver and spleen, at 0-60 minutes and 24 hours after injection, showing an increase in kidney uptake and a slight decrease in liver and spleen uptake for both Fabs (FIG. 23B). Liver uptake was significantly higher over the course of the first hour and at 24 hours after injection in rabbits injected with $^{89}$Zr-LA25 compared to $^{89}$Zr-LA24. Splenic uptake was also significantly higher at 30 and 40 minutes and 24 hours after injection in rabbits injected with $^{89}$Zr-LA25. Kidney uptake, on the other hand, was significantly higher for $^{89}$Zr-LA24 during the first hour and 24 hours post injection. Indeed, blood radioactivity half-life was longer for $^{89}$Zr-LA25, 2.2 h vs. 1.1 h for $^{89}$Zr-LA24 (FIG. 23C). Thus, as was seen in mice (FIG. 22A), the blood time-activity curve for $^{89}$Zr-LA25 in rabbits also showed delayed clearance. Importantly, PET/MR quantification results were corroborated by ex vivo gamma counting, with a significantly higher kidney uptake for $^{89}$Zr-LA24 compared to $^{89}$Zr-LA25.

Figure 23D:
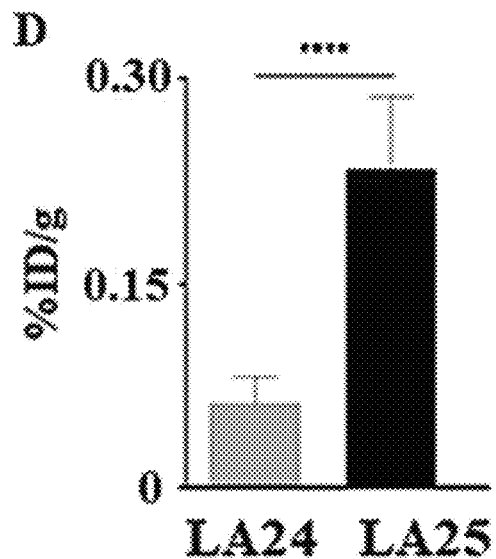
Figure 23E:
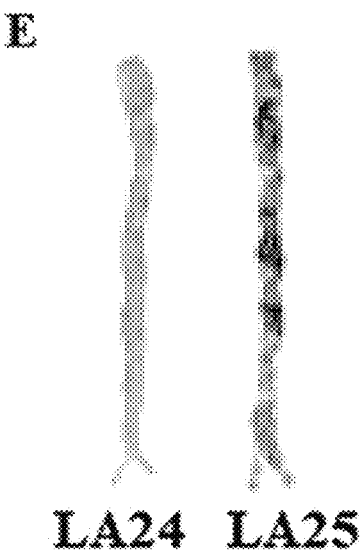

All rabbits were sacrificed 28 hours post injection and tissues harvested after thorough perfusion. Radioactivity counting revealed a significantly higher aortic uptake for $^{89}$Zr-LA25 compared to $^{89}$Zr-LA24 in rabbits with atherosclerosis, 0.022±0.003 vs. 0.006±0.001% ID/g, P<0.0001 (FIG. 23D). Autoradiography corroborated earlier results in mice, and a heterogeneous radioactivity distribution pattern was found in the $^{89}$Zr-LA25 group in contrast with a homogenous distribution found for $^{89}$Zr-LA24 (FIG. 23E).

Phenotyping of atherosclerotic plaques in rabbits. To non-invasively assess disease burden in healthy NZW rabbits versus NZW rabbits with atherosclerosis, the novel tracer $^{89}$Zr-LA25 was combined with previously validated non-invasive imaging protocols for clinical PET/MR imaging. In addition, different hallmarks of advanced atherosclerotic plaques, i.e. oxidation specific epitopes, plaque area, inflammation and neovascularization, and assessed inflammation in an earlier session by FDG-PET were simultaneously measured.

Uptake of $^{89}$Zr-LA25 was evaluated in vivo by an additional PET/MR static scan 24 hours after injection, when blood signal was low based on pharmacokinetic data.

Figure 24A:
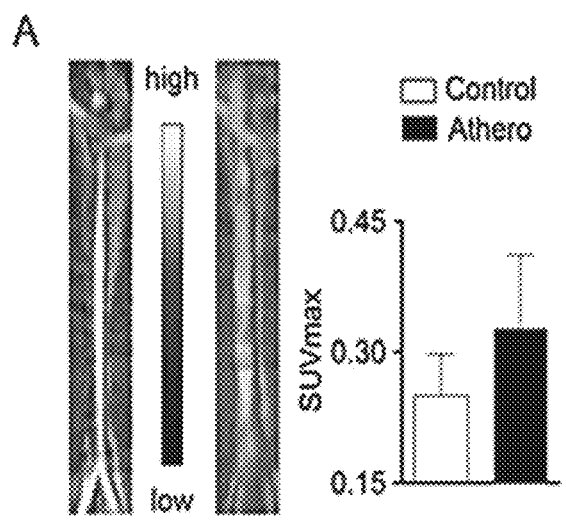
Figure 24B:
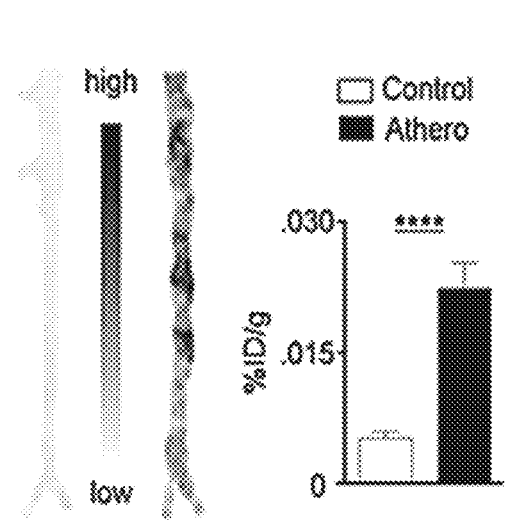

Representative aortic coronal fused PET/MR images are shown in FIG. 24A (left), in control and atherosclerotic rabbits injected with $^{89}$Zr-LA25. Uptake in the vessel wall was quantified by drawing regions of interest (ROI) on the aorta from the left renal artery to the iliac bifurcation. Radioactivity uptake was significantly higher for $^{89}$Zr-LA25 in rabbits with atherosclerosis compared with healthy controls, 0.33±0.1 vs. 0.25±0.08 g/ml, P=0.0003 (FIG. 24A, right). The PET/MR findings were confirmed by autoradiography, showing a heterogeneous deposition pattern in atherosclerotic aortas compared with the homogenous lower uptake found in control aortas (FIG. 24B, left) and ex vivo gamma counting (28 hours post injection) revealed a significantly higher uptake for $^{89}$Zr-LA25 in atherosclerotic aortas (0.022±0.003 vs. 0.005±0.001% ID/g, P<0.0001, FIG. 24B right). Moreover, correlations between the target-to-blood ratio (TBR) of aortas as determined by PET (as ratio to withdrawn blood) and gamma counting showed a significant positive correlation (r=0.92, P<0.0001).

A significantly larger plaque area in the abdominal aorta was measured for rabbits with atherosclerosis compared to their healthy control counterparts (0.29±0.06 vs. 0.11±0.03 mm$^2$, P=0.0014, FIG. 24C). Forty-eight hours prior to $^{89}$Zr-LA25 injection, inflammation was assessed by quantifying $^{18}$F-FDG uptake in the abdominal aorta by drawing ROIs on the same aortic regions as performed for $^{89}$Zr-LA25-PET. Uptake was significantly higher in atherosclerotic rabbits compared to healthy controls (1.95±0.19 vs. 0.36±0.02 g/ml, P<0.0001, FIG. 24D). Dynamic contrast enhanced MRI (DCE-MRI) was used to evaluate vascular permeability, by quantifying the uptake of Magnevist in the abdominal aorta, which was significantly higher in atherosclerotic rabbits compared to controls (4.28±1.52 vs. 1.81±1.42, P<0.0001), measured as the intensity area under the curve (IAUC) 2 minutes after injection (FIG. 24E). A fluorescently labeled reconstituted high-density lipoprotein (rHDL) nanoparticle was used as a macrophage mapping agent that was injected 24 hours before sacrifice. After euthanasia, all aortas were excised after thorough perfusion to prevent blood clots and imaged by near infrared fluorescence (NIRF). Fluorescence intensity revealed an approximately 100-fold significant increase in atherosclerotic aortas compared to controls (95±36×10$^9$ vs. 1.14±0.31×10$^9$ μW/cm, P<0.0001, FIG. 24F). In addition, NIRF imaging showed a heterogeneous fluorescence signal distribution in aortas from diseased rabbits, indicative of accumulation in atherosclerotic lesions.

Of note, a strong correlation between $^{89}$Zr-LA25 radioactivity and rHDL NIRF intensity in aortas (r=0.94, P=0.0005) was observed, possibly suggesting a certain degree of macrophage uptake of $^{89}$Zr-LA25. In addition, uptake of $^{89}$Zr-LA24 by gamma counting and rHDL NIRF intensity showed a significant negative correlation (r=−0.83 P=0.01). Furthermore, FDG uptake has been correlated with macrophage burden in plaques. In line with this, strong correlations was found between rHDL fluorescence intensity and PET-derived FDG uptake (r=0.85, P<0.0001), and ex vivo quantified $^{89}$Zr-LA25 uptake and PET-derived FDG uptake (r=0.97, P<0.0001). Moreover, a significant correlation between $^{89}$Zr-LA25 radioactivity and plaque area, as determined by T2-weighted MRI, was found (r=0.91, P=0.02). However, uptake of $^{89}$Zr-LA25 in the aorta showed no correlation with permeability as determined by DCE-MRI (IAUC), Pearson r=0.62, P=0.1.

Figure 25:
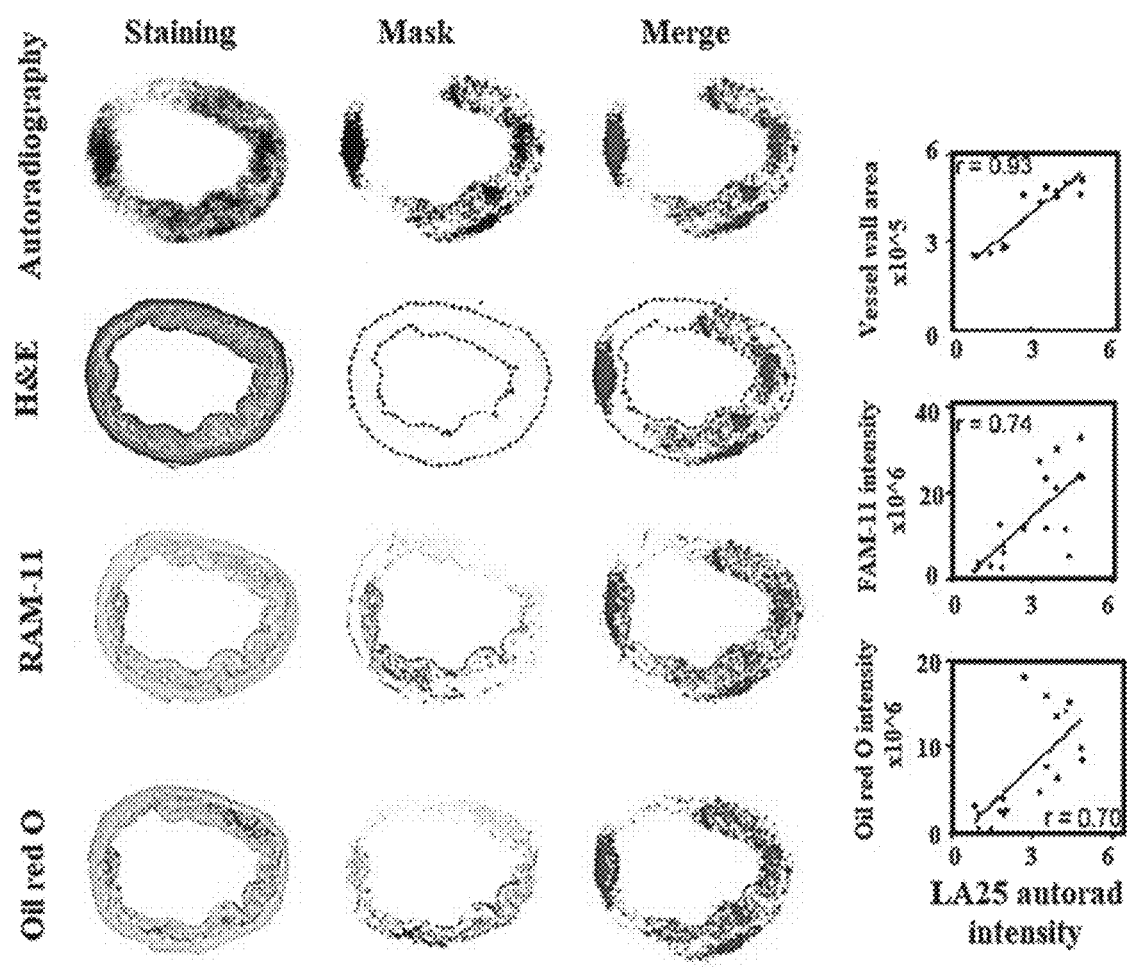
FIG. 25 shows digital autoradiography of atherosclerotic rabbit aorta sections with adjacent slides stained for H&E, RAM-11 and Oil red O, with corresponding masks and merged images with autoradiography. On the right Pearson correlations are shown for autoradiography with vessel wall area (r=0.93, P<0.0001), RAM-11 (r=0.74, P=0.0004) and Oil red O (r=0.70, P=0.0008).
Figure 26:
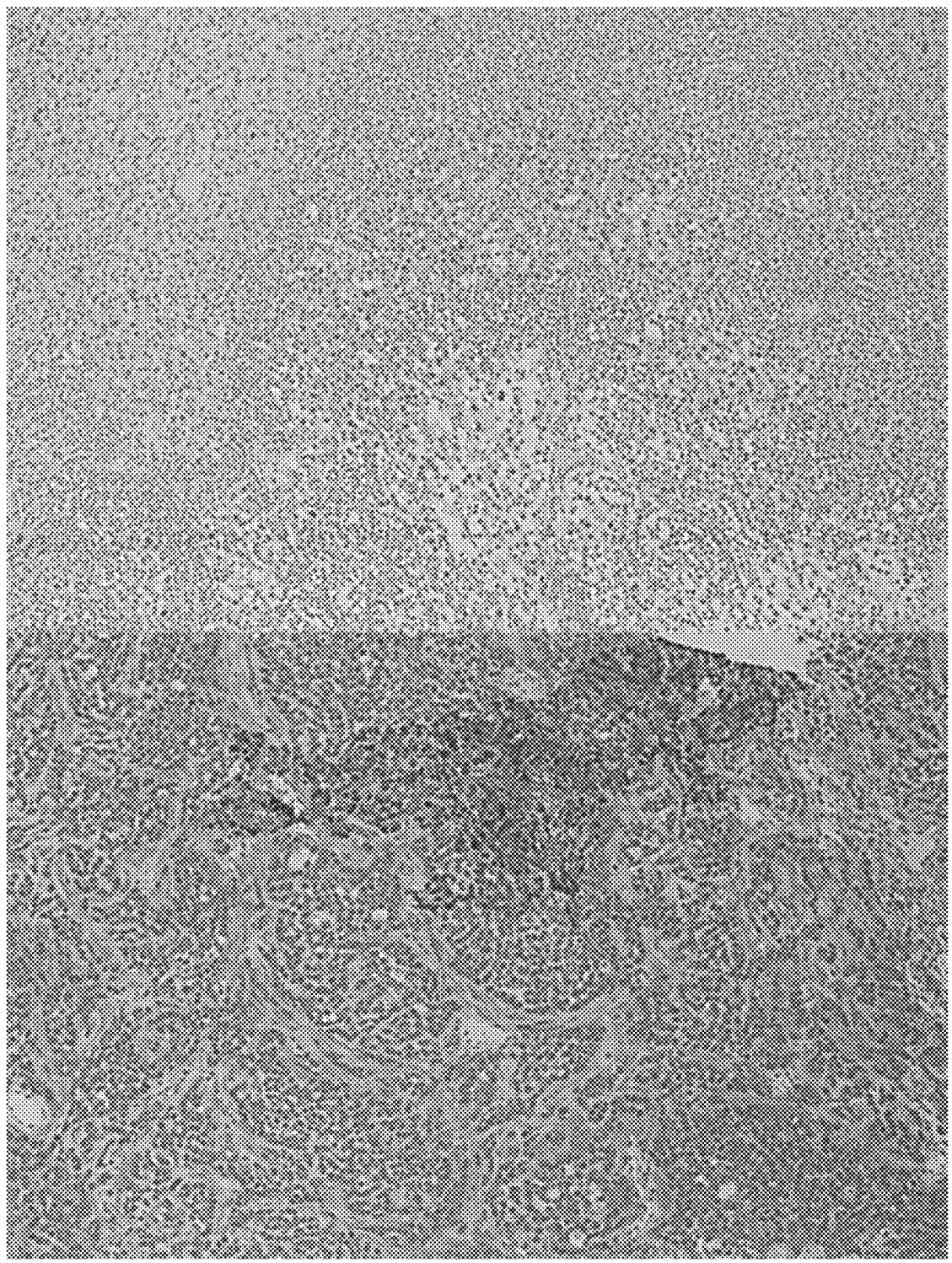
FIG. 26 shows staining of brain tissue for with an antibody of the disclosure against MAA adducts. The image shows that MAA adducts are stained in glioblastoma multiforme (GBM).

Ex vivo plaque characterization. After rabbits were sacrificed for ex vivo validation, one abdominal aorta was divided into several different pieces and processed for histology. The first section in a set of slides was used for luminal autoradiography and adjacent sections were stained for vessel wall area with conventional hematoxylin & eosin (H&E), RAM-11 for macrophages and Oil red O for lipid content; representative images are shown in FIG. 25. After the integrated density (mean grey value) area of $^{89}$Zr-LA25 was determined for all luminal autoradiography, correlations on the adjacent sections were calculated to be r=0.93 (P<0.0001) for vessel wall area, r=0.74 (P=0.0004) for macrophages and r=0.70 (P=0.0008) for lipids (FIG. 25).

A number of embodiments have been described herein. Nevertheless, it will be understood that various modifications may be made without departing from the spirit and scope of this disclosure. Accordingly, other embodiments are within the scope of the following claims.

What is claimed is:

1. An isolated antibody or antibody fragment that binds to an MAA oxidized specific epitope (MAA-OSE), wherein the antibody or antibody fragment comprises: a variable heavy chain (VH) domain and a variable light chain (VL) domain, wherein the VH and VL, respectively, comprise the three heavy chain complementarity determining region (CDR) amino acid sequences and the three light chain CDR amino acid sequences of the VH and VL set forth in SEQ ID NOs: 8 and 6; 16 and 14; or 20 and 18.

2. The antibody or antibody fragment of claim 1, wherein: the VH comprises the CDR amino acid sequences set forth in SEQ ID NOs: 25, 26 and 27; 31, 32, and 33; or 34, 35 and 36; and/or the VL comprises the CDR amino acid sequences set forth in SEQ ID NOs: 40, 41 and 4; 46, 47, and 48; or 49, 50 and 51.

3. The antibody or antibody fragment of claim 1, wherein:
(a) the VH comprises the CDR amino acid sequences set forth in SEQ ID NOs: 25, 26 and 27, and the VL comprises the CDR amino acid sequences set forth in SEQ ID NOs: 40, 41 and 42;
(b) the VH comprises the CDR amino acid sequences set forth in SEQ ID NOs: 31, 32 and 33, and the VL comprises the CDR amino acid sequences set forth in SEQ ID NOs: 46, 47 and 48; or
(c) the VH comprises the CDR amino acid sequences set forth in SEQ ID NOs: 34, 35 and 36, and the VL comprises the CDR amino acid sequences set forth in SEQ ID NOs: 49, 50 and 51.

4. The antibody or antibody fragment of claim 1, wherein: the VH comprises the amino acid sequence of SEQ ID NO: 8, 16, or 20; and/or the VL comprises the amino acid sequence of SEQ ID NO: 6, 14, or 18.

5. The antibody or antibody fragment of claim 1, wherein the VH and VL, respectively, comprise the amino acid sequences of SEQ ID NOs: 8 and 6; 16 and 14; or 20 and 18.

6. The antibody or antibody fragment of claim 1, wherein the antibody or fragment is a chimeric antibody or a humanized antibody.

7. The antibody or antibody fragment of claim 1, which is an scFv, a Fab, a Fab', a F (ab')$_2$, or a diabody.

8. The antibody or antibody fragment of claim 1, wherein the antibody or fragment comprises an Fc region, optionally wherein the Fc region is from an IgG, IgM, IgA, IgD, IgE antibody, or any subclass thereof, optionally wherein the Fc region is a variant Fc region.

9. A polynucleotide or a plurality of polynucleotides encoding a VH and a VL of the antibody or antibody fragment of claim 1.

10. A vector comprising the polynucleotide of claim 9.

11. A recombinant host cell comprising the polynucleotide of claim 9.

12. A pharmaceutical composition comprising the antibody or antibody fragment of claim 1 and a pharmaceutically acceptable carrier.

13. A method of producing an antibody that binds to MAA-OSE, the method comprising culturing the host cell of claim 11 under conditions such that the antibody is produced.

* * * * *

UNITED STATES PATENT AND TRADEMARK OFFICE
CERTIFICATE OF CORRECTION

| | | |
|---|---|---|
| PATENT NO. | : 12,351,649 B2 | Page 1 of 1 |
| APPLICATION NO. | : 17/500794 | |
| DATED | : July 8, 2025 | |
| INVENTOR(S) | : Sotirios Tsimikas, Joseph Witztum and Xuchu Que | |

It is certified that error appears in the above-identified patent and that said Letters Patent is hereby corrected as shown below:

In the Claims

At Column 77, Line 45, please delete "SEQ ID NOs: 40, 41 and 4" and insert --SEQ ID NOs: 40, 41, and 42--.

Signed and Sealed this
Seventh Day of October, 2025

John A. Squires
*Director of the United States Patent and Trademark Office*

SEQUENCE LISTING

<160> NUMBER OF SEQ ID NOS: 54

<210> SEQ ID NO 1
<211> LENGTH: 333
<212> TYPE: DNA
<213> ORGANISM: Artificial Sequence
<220> FEATURE:
<223> OTHER INFORMATION: LA25 VL sequence human
<220> FEATURE:
<221> NAME/KEY: CDS
<222> LOCATION: (1)..(333)

<400> SEQUENCE: 1

```
gag ctc ggc ctg act cag cct ccc tcc gtg tct ggg tct cct gga cag      48
Glu Leu Gly Leu Thr Gln Pro Pro Ser Val Ser Gly Ser Pro Gly Gln
1               5                   10                  15 tcg atc acc atc tcc tgc act gga acc agc agt gac gtt ggt ggt tat      96
Ser Ile Thr Ile Ser Cys Thr Gly Thr Ser Ser Asp Val Gly Gly Tyr
                20                  25                  30 aac tat gtc tcc tgg tac caa cag cac cca ggc aaa gcc ccc aaa ctc     144
Asn Tyr Val Ser Trp Tyr Gln Gln His Pro Gly Lys Ala Pro Lys Leu
            35                  40                  45 atg att tat gag gtc agt aat cgg ccc tca ggg gtt tct aat cgc ttc     192
Met Ile Tyr Glu Val Ser Asn Arg Pro Ser Gly Val Ser Asn Arg Phe
        50                  55                  60 tct ggc tcc aag cct ggc aac acg gcc tcc ctg acc atc tct ggg ctc     240
Ser Gly Ser Lys Pro Gly Asn Thr Ala Ser Leu Thr Ile Ser Gly Leu
65                  70                  75                  80 cag gct gag gat gag gct gat tat tac tgc agc tca tat gca ggc agc     288
Gln Ala Glu Asp Glu Ala Asp Tyr Tyr Cys Ser Ser Tyr Ala Gly Ser
                85                  90                  95 aac aat tat tgg gtg ttc ggc gga ggg acc aag ctg acc gtc cta         333
Asn Asn Tyr Trp Val Phe Gly Gly Gly Thr Lys Leu Thr Val Leu
            100                 105                 110
```

<210> SEQ ID NO 2
<211> LENGTH: 111
<212> TYPE: PRT
<213> ORGANISM: Artificial Sequence
<220> FEATURE:
<223> OTHER INFORMATION: Synthetic Construct

<400> SEQUENCE: 2

```
Glu Leu Gly Leu Thr Gln Pro Pro Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Pro Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Asn Asn Tyr Trp Val Phe Gly Gly Gly Thr Lys Leu Thr Val Leu
            100                 105                 110
```

<210> SEQ ID NO 3
<211> LENGTH: 351
<212> TYPE: DNA
<213> ORGANISM: Artificial Sequence
<220> FEATURE:
<223> OTHER INFORMATION: LA25 VH sequence human
<220> FEATURE:
<221> NAME/KEY: CDS
<222> LOCATION: (1)..(351)

<400> SEQUENCE: 3

```
cag gtg cag cgg cag gag tcg ggg gga ggc tta gtt cag cct ggg ggg      48
Gln Val Gln Arg Gln Glu Ser Gly Gly Gly Leu Val Gln Pro Gly Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg     192
Ala Val Ile Trp Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg aga ggc cgc tgg ggg ggg tac ttc gat ctc tgg ggc cgt gga acc     336
Ala Arg Gly Arg Trp Gly Gly Tyr Phe Asp Leu Trp Gly Arg Gly Thr
            100                 105                 110 ctg gtc acc gtc tcc                                                  351
Leu Val Thr Val Ser
        115
```

<210> SEQ ID NO 4
<211> LENGTH: 117
<212> TYPE: PRT
<213> ORGANISM: Artificial Sequence
<220> FEATURE:
<223> OTHER INFORMATION: Synthetic Construct

<400> SEQUENCE: 4

```
Gln Val Gln Arg Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Trp Gly Gly Tyr Phe Asp Leu Trp Gly Arg Gly Thr
            100                 105                 110

Leu Val Thr Val Ser
        115
```

<210> SEQ ID NO 5
<211> LENGTH: 334
<212> TYPE: DNA
<213> ORGANISM: Artificial Sequence

```
<220> FEATURE:
<223> OTHER INFORMATION: KA2 VL sequence human
<220> FEATURE:
<221> NAME/KEY: CDS
<222> LOCATION: (1)..(333)

<400> SEQUENCE: 5 gag ctc gtg atg act cag tct cca ctc tcc ctg ccc gtc acc cct gga      48
Glu Leu Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act cac agt ttt ggc cag ggg acc aag ctg gag atc aaa c       334
Leu Gln Thr His Ser Phe Gly Gln Gly Thr Lys Leu Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: Synthetic Construct

<400> SEQUENCE: 6

Glu Leu Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr His Ser Phe Gly Gln Gly Thr Lys Leu Glu Ile Lys
            100                 105                 110

<210> SEQ ID NO 7
<211> LENGTH: 343
<212> TYPE: DNA
<213> ORGANISM: Artificial Sequence
<220> FEATURE:
<223> OTHER INFORMATION: KA2 VH sequence human
<220> FEATURE:
<221> NAME/KEY: CDS
<222> LOCATION: (1)..(342)

<400> SEQUENCE: 7
```

```
cag gtg cag cgg cag gag tcg ggg gga ggc tta gtt cag cct ggg ggg      48
Gln Val Gln Arg Gln Glu Ser Gly Gly Gly Leu Val Gln Pro Gly Gly
1               5                   10                  15 tcc ctg aga ctc tcc tgt gca gcc tct gga ttc acc ttc agt agc tac      96
Ser Leu Arg Leu Ser Cys Ala Ala Ser Gly Phe Thr Phe Ser Ser Tyr
            20                  25                  30 tgg atg cac tgg gtc cgc caa gct cca ggg aag ggg ctg gtg tgg gtc     144
Trp Met His Trp Val Arg Gln Ala Pro Gly Lys Gly Leu Val Trp Val
        35                  40                  45 tca cgt att aat agt gat ggg agt agc aca agc tac gcg gac tcc gtg     192
Ser Arg Ile Asn Ser Asp Gly Ser Ser Thr Ser Tyr Ala Asp Ser Val
    50                  55                  60 aag ggc cga ttc acc atc tcc aga gac aac gcc aag aac acg ctg tat     240
Lys Gly Arg Phe Thr Ile Ser Arg Asp Asn Ala Lys Asn Thr Leu Tyr
65                  70                  75                  80 ctg caa atg aac agt ctg aga gcc gag gac acg gct gtg tat tac tgt     288
Leu Gln Met Asn Ser Leu Arg Ala Glu Asp Thr Ala Val Tyr Tyr Cys
                85                  90                  95 gca aga gat tat agc agc agc tgg tac ttt gac tac tgg ggc cag gga     336
Ala Arg Asp Tyr Ser Ser Ser Trp Tyr Phe Asp Tyr Trp Gly Gln Gly
            100                 105                 110 acc ctg g                                                            343
Thr Leu <210> SEQ ID NO 8
<211> LENGTH: 114
<212> TYPE: PRT
<213> ORGANISM: Artificial Sequence
<220> FEATURE:
<223> OTHER INFORMATION: Synthetic Construct

<400> SEQUENCE: 8

Gln Val Gln Arg Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Ser Ser Trp Tyr Phe Asp Tyr Trp Gly Gln Gly
            100                 105                 110

Thr Leu

<210> SEQ ID NO 9
<211> LENGTH: 331
<212> TYPE: DNA
<213> ORGANISM: Artificial Sequence
<220> FEATURE:
<223> OTHER INFORMATION: LRO4 VL sequence mouse
<220> FEATURE:
<221> NAME/KEY: CDS
<222> LOCATION: (1)..(330)

<400> SEQUENCE: 9 gac att ttg atg aca cag gct gca ccc tct gta cct gtc act cct gga      48
```

```
                Asp Ile Leu Met Thr Gln Ala Ala Pro Ser Val Pro Val Thr Pro Gly
                1               5                   10                  15 gag tca gta tcc atc tcc tgc agg tct agt aag agt ctc ctg cat agt           96
Glu Ser Val Ser Ile Ser Cys Arg Ser Ser Lys Ser Leu Leu His Ser
                20                  25                  30 aat ggc aac act tac ttg tat tgg ttc ctg cag agg cca ggc cag tct          144
Asn Gly Asn Thr Tyr Leu Tyr Trp Phe Leu Gln Arg Pro Gly Gln Ser
            35                  40                  45 cct cag ctc ctg ata tat cgg atg tcc aac ctt gcc tca gga gtc cca          192
Pro Gln Leu Leu Ile Tyr Arg Met Ser Asn Leu Ala Ser Gly Val Pro
        50                  55                  60 gac agg ttc agt ggc agt ggg tca gga act gct ttc aca ctg aga atc          240
Asp Arg Phe Ser Gly Ser Gly Ser Gly Thr Ala Phe Thr Leu Arg Ile
65                  70                  75                  80 agt aga gtg gag gct gag gat gtg ggt gtt tat tac tgt atg caa cat          288
Ser Arg Val Glu Ala Glu Asp Val Gly Val Tyr Tyr Cys Met Gln His
                85                  90                  95 cta gaa tat cct tac acg ttc gga ggg ggg acc aag ctg gaa a                331
Leu Glu Tyr Pro Tyr Thr Phe Gly Gly Gly Thr Lys Leu Glu
            100                 105                 110
```

<210> SEQ ID NO 10
<211> LENGTH: 110
<212> TYPE: PRT
<213> ORGANISM: Artificial Sequence
<220> FEATURE:
<223> OTHER INFORMATION: Synthetic Construct

<400> SEQUENCE: 10

```
Asp Ile Leu Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu
            100                 105                 110
```

<210> SEQ ID NO 11
<211> LENGTH: 359
<212> TYPE: DNA
<213> ORGANISM: Artificial Sequence
<220> FEATURE:
<223> OTHER INFORMATION: LRO4 VH sequence mouse
<220> FEATURE:
<221> NAME/KEY: CDS
<222> LOCATION: (1)..(342)

<400> SEQUENCE: 11

```
cag atc cag ttg gtg cag tct gga cct gag ctg aag aag cct gga gag           48
Gln Ile Gln Leu Val Gln Ser Gly Pro Glu Leu Lys Lys Pro Gly Glu
1               5                   10                  15 aca gtc aag atc tcc tgc aag gct tct ggg tat acc ttc aca acc tat           96
Thr Val Lys Ile Ser Cys Lys Ala Ser Gly Tyr Thr Phe Thr Thr Tyr
                20                  25                  30
```

```
gga atg agc tgg gtg aaa cag gct cca gga aag ggt tta aag tgg atg      144
Gly Met Ser Trp Val Lys Gln Ala Pro Gly Lys Gly Leu Lys Trp Met
        35                  40                  45 ggc tgg ata aac acc tac tct gga gtg cca aca tat gct gat gac ttc      192
Gly Trp Ile Asn Thr Tyr Ser Gly Val Pro Thr Tyr Ala Asp Asp Phe
 50                  55                  60 aag gga cgg ttt gcc ttc tct ttg gaa acc tct gcc agc act gcc tat      240
Lys Gly Arg Phe Ala Phe Ser Leu Glu Thr Ser Ala Ser Thr Ala Tyr
 65                  70                  75                  80 ttg cag atc aac aac ctc aaa aat gag gac acg gct aca tat ttc tgt      288
Leu Gln Ile Asn Asn Leu Lys Asn Glu Asp Thr Ala Thr Tyr Phe Cys
                 85                  90                  95 gca aaa ctg ggg ttt gct tac tgg ggc caa ggg act ctg gtc act gtc      336
Ala Lys Leu Gly Phe Ala Tyr Trp Gly Gln Gly Thr Leu Val Thr Val
            100                 105                 110 tct gca gagagtcagt ccttccc                                            359
Ser Ala <210> SEQ ID NO 12
<211> LENGTH: 114
<212> TYPE: PRT
<213> ORGANISM: Artificial Sequence
<220> FEATURE:
<223> OTHER INFORMATION: Synthetic Construct

<400> SEQUENCE: 12

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Lys Leu Gly Phe Ala Tyr Trp Gly Gln Gly Thr Leu Val Thr Val
            100                 105                 110

Ser Ala

<210> SEQ ID NO 13
<211> LENGTH: 331
<212> TYPE: DNA
<213> ORGANISM: Artificial Sequence
<220> FEATURE:
<223> OTHER INFORMATION: ML7 VL sequence human
<220> FEATURE:
<221> NAME/KEY: CDS
<222> LOCATION: (1)..(330)

<400> SEQUENCE: 13 gag ctc gtg ctg act cag cca ccc tca gcg tct ggg acc ccc ggg cag       48
Glu Leu Val Leu Thr Gln Pro Pro Ser Ala Ser Gly Thr Pro Gly Gln
 1               5                  10                  15 agg gtc acc atc tct tgt tct gga agc agc tcc aac atc gga agt aat       96
Arg Val Thr Ile Ser Cys Ser Gly Ser Ser Ser Asn Ile Gly Ser Asn
            20                  25                  30 tat gta tat tgg tac cag cag ctc cca gga acg gcc ccc aaa ctc ctc      144
Tyr Val Tyr Trp Tyr Gln Gln Leu Pro Gly Thr Ala Pro Lys Leu Leu
```

```
           35                  40                  45
atc tat agt aat aat cag cgg ccc tca ggg gtc cct gac cga ttc tct    192
Ile Tyr Ser Asn Asn Gln Arg Pro Ser Gly Val Pro Asp Arg Phe Ser
     50                  55                  60 ggc tcc aag cct ggc acc tca gcc tcc ctg gcc atc agt ggg ctc cag    240
Gly Ser Lys Pro Gly Thr Ser Ala Ser Leu Ala Ile Ser Gly Leu Gln
 65                  70                  75                  80 tct gac gat gag gct gat tat tat tgt gca gcg tgg gac gtc agc ctg    288
Ser Asp Asp Glu Ala Asp Tyr Tyr Cys Ala Ala Trp Asp Val Ser Leu
                 85                  90                  95 aga caa tgg ctg ttc ggc gga ggg acc aag ctg acc gtc cta g          331
Arg Gln Trp Leu Phe Gly Gly Gly Thr Lys Leu Thr Val Leu
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: Synthetic Construct

<400> SEQUENCE: 14

Glu Leu Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
     50                  55                  60

Gly Ser Lys Pro Gly Thr Ser Ala Ser Leu Ala Ile Ser Gly Leu Gln
 65                  70                  75                  80

Ser Asp Asp Glu Ala Asp Tyr Tyr Cys Ala Ala Trp Asp Val Ser Leu
                 85                  90                  95

Arg Gln Trp Leu Phe Gly Gly Gly Thr Lys Leu Thr Val Leu
            100                 105                 110

<210> SEQ ID NO 15
<211> LENGTH: 349
<212> TYPE: DNA
<213> ORGANISM: Artificial Sequence
<220> FEATURE:
<223> OTHER INFORMATION: ML7 VH sequence human
<220> FEATURE:
<221> NAME/KEY: CDS
<222> LOCATION: (1)..(348)

<400> SEQUENCE: 15 cag gtg gag cgg gtg cag tct ggg gga ggc gtg gtc cag cct ggg agg     48
Gln Val Glu Arg Val Gln Ser Gly Gly Gly Val Val Gln Pro Gly Arg
 1               5                  10                  15 tcc ctg aga ctc tcc tgt gca gcg tct gga ttc acc ttc agt agc tat     96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
         35                  40                  45 gca gtt ata tgg tat gat gga agt aat aaa tac tat gca gac tcc gtg    192
Ala Val Ile Trp Tyr Asp Gly Ser Asn Lys Tyr Tyr Ala Asp Ser Val
     50                  55                  60 aag ggc cga ttc acc atc tcc aga gac aat tcc aag aac acg ctg tat    240
```

```
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
             85                  90                  95 gcg aga ggt tca tta tcc ggg ctg gac gtc tgg ggc caa gga acc ctg     336
Ala Arg Gly Ser Leu Ser Gly Leu Asp Val Trp Gly Gln Gly Thr Leu
            100                 105                 110 gtc acc gtc tcc t                                                   349
Val Thr Val Ser
            115

<210> SEQ ID NO 16
<211> LENGTH: 116
<212> TYPE: PRT
<213> ORGANISM: Artificial Sequence
<220> FEATURE:
<223> OTHER INFORMATION: Synthetic Construct

<400> SEQUENCE: 16

Gln Val Glu Arg Val Gln Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Gly Ser Leu Ser Gly Leu Asp Val Trp Gly Gln Gly Thr Leu
            100                 105                 110

Val Thr Val Ser
            115

<210> SEQ ID NO 17
<211> LENGTH: 322
<212> TYPE: DNA
<213> ORGANISM: Artificial Sequence
<220> FEATURE:
<223> OTHER INFORMATION: MK17 VL sequence human
<220> FEATURE:
<221> NAME/KEY: CDS
<222> LOCATION: (1)..(321)

<400> SEQUENCE: 17 gag ctc gtg ttg acg cag tct cca tcc ttc ctg tct gca tct ata gga     48
Glu Leu Val Leu Thr Gln Ser Pro Ser Phe Leu Ser Ala Ser Ile Gly
 1               5                   10                  15 gac aga gtc acc atc act tgc cgg gcc agt cag ggc att ggc aat tat     96
Asp Arg Val Thr Ile Thr Cys Arg Ala Ser Gln Gly Ile Gly Asn Tyr
             20                  25                  30 tta gcc tgg tat cag caa aaa cca ggg aaa gcc cct aag ctc ctg att    144
Leu Ala Trp Tyr Gln Gln Lys Pro Gly Lys Ala Pro Lys Leu Leu Ile
         35                  40                  45 tat gct gca tcc act ttg caa agt ggg gtc cca tca agg ttc agc ggc    192
Tyr Ala Ala Ser Thr Leu Gln Ser Gly Val Pro Ser Arg Phe Ser Gly
     50                  55                  60 agt aaa tct ggg aca gag ttc act ctc aca atc agc agc ctt cag cct    240
```

```
Ser Lys Ser Gly Thr Glu Phe Thr Leu Thr Ile Ser Ser Leu Gln Pro
 65                  70                  75                  80 gag gat tct gca act tat tac tgt cag caa ctt aac ggt tac cct ctc        288
Glu Asp Ser Ala Thr Tyr Tyr Cys Gln Gln Leu Asn Gly Tyr Pro Leu
                     85                  90                  95 act ttc ggc cct ggg acc aaa gtg gat atc aaa c                          322
Thr Phe Gly Pro Gly Thr Lys Val Asp Ile Lys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

```
Glu Leu Val Leu Thr Gln Ser Pro Ser Phe Leu Ser Ala Ser Ile Gly
1               5                   10                  15

Asp Arg Val Thr Ile Thr Cys Arg Ala Ser Gln Gly Ile Gly Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Lys Ser Gly Thr Glu Phe Thr Leu Thr Ile Ser Ser Leu Gln Pro
65                  70                  75                  80

Glu Asp Ser Ala Thr Tyr Tyr Cys Gln Gln Leu Asn Gly Tyr Pro Leu
                85                  90                  95

Thr Phe Gly Pro Gly Thr Lys Val Asp Ile Lys
            100                 105
```

<210> SEQ ID NO 19
<211> LENGTH: 367
<212> TYPE: DNA
<213> ORGANISM: Artificial Sequence
<220> FEATURE:
<223> OTHER INFORMATION: MK17 VH sequence human
<220> FEATURE:
<221> NAME/KEY: CDS
<222> LOCATION: (1)..(363)

<400> SEQUENCE: 19

```
cag ctg gtg cag tct ggg gga ggc gtg gtc cag cct ggg cgg tcc ctg        48
Gln Leu Val Gln Ser Gly Gly Gly Val Val Gln Pro Gly Arg Ser Leu
1               5                   10                  15 aga ctc tcc tgt gca gcg tct gga ttc acc ttc agt agc tat ggc atg        96
Arg Leu Ser Cys Ala Ala Ser Gly Phe Thr Phe Ser Ser Tyr Gly Met
            20                  25                  30 cac tgg gtc cgc cag gct cca ggc aag ggg ctg gag tgg gtg gca gtt        144
His Trp Val Arg Gln Ala Pro Gly Lys Gly Leu Glu Trp Val Ala Val
        35                  40                  45 ata tgg tat gat gga agt aat aaa tac tat gca gac tcc gtg aag ggc        192
Ile Trp Tyr Asp Gly Ser Asn Lys Tyr Tyr Ala Asp Ser Val Lys Gly
50                  55                  60 cga ttc acc atc tcc aga gac aat tcc aag aac acg ctg tat ctg caa        240
Arg Phe Thr Ile Ser Arg Asp Asn Ser Lys Asn Thr Leu Tyr Leu Gln
65                  70                  75                  80 atg aac agc ctg aga gcc gag gac acg gct gtg tat tac tgt gcg aga        288
Met Asn Ser Leu Arg Ala Glu Asp Thr Ala Val Tyr Tyr Cys Ala Arg
                85                  90                  95
```

```
gat cgg ggt tat ccg tgg cta cga tcc cgg ggc ggt atg gac gtc tgg         336
Asp Arg Gly Tyr Pro Trp Leu Arg Ser Arg Gly Gly Met Asp Val Trp
            100                 105                 110 ggc caa ggc acc ctg gtc acc gtc tcc ctg                                 367
Gly Gln Gly Thr Leu Val Thr Val Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: Synthetic Construct

<400> SEQUENCE: 20

Gln Leu Val Gln Ser Gly Gly Val Val Gln Pro Gly Arg Ser Leu
1               5                   10                  15

Arg Leu Ser Cys Ala Ala Ser Gly Phe Thr Phe Ser Ser Tyr Gly Met
                20                  25                  30

His Trp Val Arg Gln Ala Pro Gly Lys Gly Leu Glu Trp Val Ala Val
            35                  40                  45

Ile Trp Tyr Asp Gly Ser Asn Lys Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Arg Gly Tyr Pro Trp Leu Arg Ser Arg Gly Gly Met Asp Val Trp
            100                 105                 110

Gly Gln Gly Thr Leu Val Thr Val Ser
        115                 120

<210> SEQ ID NO 21
<211> LENGTH: 326
<212> TYPE: DNA
<213> ORGANISM: Artificial Sequence
<220> FEATURE:
<223> OTHER INFORMATION: LA24 VL sequence human
<220> FEATURE:
<221> NAME/KEY: CDS
<222> LOCATION: (1)..(324)

<400> SEQUENCE: 21 gag ctc aca ctc acg cag tct cca ggc acc ctg tct ttg tct cca ggg         48
Glu Leu Thr Leu Thr Gln Ser Pro Gly Thr Leu Ser Leu Ser Pro Gly
1               5                   10                  15 gaa aga gcc acc ctc tcc tgc agg gcc agt cag agt gtt agc agc agc         96
Glu Arg Ala Thr Leu Ser Cys Arg Ala Ser Gln Ser Val Ser Ser Ser
                20                  25                  30 tac tta gcc tgg tac cag cag aaa cct ggc cag gct ccc agg ctc ctc         144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt         192
Ile Tyr Gly Ala Ser Ser Arg Ala Thr Gly Ile Pro Asp Arg Phe Ser
        50                  55                  60 ggc agt ggg tct ggg aca gat ttc act ctc acc atc agc agc ctg cag         240
Gly Ser Gly Ser Gly Thr Asp Phe Thr Leu Thr Ile Ser Ser Leu Gln
65                  70                  75                  80 cct gaa gat gtt gca act tat tac tgt caa aag tat aac agt gcc ccg         288
Pro Glu Asp Val Ala Thr Tyr Tyr Cys Gln Lys Tyr Asn Ser Ala Pro
                85                  90                  95
```

```
ctc act ttc ggc gga ggg acc aag gtg gag atc aaa cg            326
Leu Thr Phe Gly Gly Gly Thr Lys Val Glu Ile Lys
            100                 105
```

<210> SEQ ID NO 22
<211> LENGTH: 108
<212> TYPE: PRT
<213> ORGANISM: Artificial Sequence
<220> FEATURE:
<223> OTHER INFORMATION: Synthetic Construct

<400> SEQUENCE: 22

```
Glu Leu Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Lys Tyr Asn Ser Ala Pro
                85                  90                  95

Leu Thr Phe Gly Gly Gly Thr Lys Val Glu Ile Lys
            100                 105
```

<210> SEQ ID NO 23
<211> LENGTH: 358
<212> TYPE: DNA
<213> ORGANISM: Artificial Sequence
<220> FEATURE:
<223> OTHER INFORMATION: LA24 VH sequence human
<220> FEATURE:
<221> NAME/KEY: CDS
<222> LOCATION: (1)..(357)

<400> SEQUENCE: 23

```
gag gtg cag ctg ttg gag tct ggg gga ggc ttg gta aag cct ggg ggg     48
Glu Val Gln Leu Leu Glu Ser Gly Gly Gly Leu Val Lys Pro Gly Gly
1               5                   10                  15 tcc ctt aga ctc tcc tgt gca gcg tct gga ttc acc ttc ggt agc tat     96
Ser Leu Arg Leu Ser Cys Ala Ala Ser Gly Phe Thr Phe Gly Ser Tyr
                20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
            35                  40                  45 gca ttt ata cgg tat gat gga agt aat aaa tac tat gca gac tcc gtg    192
Ala Phe Ile Arg Tyr Asp Gly Ser Asn Lys Tyr Tyr Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt    288
Leu Gln Met Asn Ser Leu Arg Ala Glu Asp Thr Ala Val Tyr Tyr Cys
                85                  90                  95 gcg aaa ccc ggg ccc tgg ggc tgg tac ttt gac tac tgg ggc cag gga    336
Ala Lys Pro Gly Pro Trp Gly Trp Tyr Phe Asp Tyr Trp Gly Gln Gly
            100                 105                 110 acc ctg gtc acc gtc tcc tca g                                      358
Thr Leu Val Thr Val Ser Ser
            115
```

```
<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Pro Trp Gly Trp Tyr Phe Asp Tyr Trp Gly Gln Gly
            100                 105                 110

Thr Leu Val Thr Val Ser Ser
        115

<210> SEQ ID NO 25
<211> LENGTH: 8
<212> TYPE: PRT
<213> ORGANISM: Artificial Sequence
<220> FEATURE:
<223> OTHER INFORMATION: KA2 VH CDR1

<400> SEQUENCE: 25

Gly Phe Thr Phe Ser Ser Tyr Trp
1               5

<210> SEQ ID NO 26
<211> LENGTH: 8
<212> TYPE: PRT
<213> ORGANISM: Artificial Sequence
<220> FEATURE:
<223> OTHER INFORMATION: KA2 VH CDR2

<400> SEQUENCE: 26

Ile Asn Ser Asp Gly Ser Ser Thr
1               5

<210> SEQ ID NO 27
<211> LENGTH: 14
<212> TYPE: PRT
<213> ORGANISM: Artificial Sequence
<220> FEATURE:
<223> OTHER INFORMATION: KA2 VH CDR3

<400> SEQUENCE: 27

Cys Ala Arg Asp Tyr Ser Ser Trp Tyr Phe Asp Tyr Trp
1               5                   10

<210> SEQ ID NO 28
<211> LENGTH: 8
<212> TYPE: PRT
<213> ORGANISM: Artificial Sequence
```

```
<220> FEATURE:
<223> OTHER INFORMATION: LRO4 VH CDR1

<400> SEQUENCE: 28

Gly Tyr Thr Phe Thr Thr Tyr Gly
1               5

<210> SEQ ID NO 29
<211> LENGTH: 8
<212> TYPE: PRT
<213> ORGANISM: Artificial Sequence
<220> FEATURE:
<223> OTHER INFORMATION: LRO4 VH CDR2

<400> SEQUENCE: 29

Ile Asn Thr Tyr Ser Gly Val Pro
1               5

<210> SEQ ID NO 30
<211> LENGTH: 9
<212> TYPE: PRT
<213> ORGANISM: Artificial Sequence
<220> FEATURE:
<223> OTHER INFORMATION: LRO4 VH CDR3

<400> SEQUENCE: 30

Cys Ala Lys Leu Gly Phe Ala Tyr Trp
1               5

<210> SEQ ID NO 31
<211> LENGTH: 8
<212> TYPE: PRT
<213> ORGANISM: Artificial Sequence
<220> FEATURE:
<223> OTHER INFORMATION: ML7 VH CDR1

<400> SEQUENCE: 31

Gly Phe Thr Phe Ser Ser Tyr Gly
1               5

<210> SEQ ID NO 32
<211> LENGTH: 8
<212> TYPE: PRT
<213> ORGANISM: Artificial Sequence
<220> FEATURE:
<223> OTHER INFORMATION: ML7 VH CDR2

<400> SEQUENCE: 32

Ile Trp Tyr Asp Gly Ser Asn Lys
1               5

<210> SEQ ID NO 33
<211> LENGTH: 12
<212> TYPE: PRT
<213> ORGANISM: Artificial Sequence
<220> FEATURE:
<223> OTHER INFORMATION: ML7 VH CDR3

<400> SEQUENCE: 33

Cys Ala Arg Gly Ser Leu Ser Gly Leu Asp Val Trp
1               5                   10

<210> SEQ ID NO 34
<211> LENGTH: 8
<212> TYPE: PRT
<213> ORGANISM: Artificial Sequence
<220> FEATURE:
```

```
<223> OTHER INFORMATION: MK17 VH CDR1

<400> SEQUENCE: 34

Gly Phe Thr Phe Ser Ser Tyr Gly
1               5

<210> SEQ ID NO 35
<211> LENGTH: 8
<212> TYPE: PRT
<213> ORGANISM: Artificial Sequence
<220> FEATURE:
<223> OTHER INFORMATION: MK17 VH CDR2

<400> SEQUENCE: 35

Ile Trp Tyr Asp Gly Ser Asn Lys
1               5

<210> SEQ ID NO 36
<211> LENGTH: 18
<212> TYPE: PRT
<213> ORGANISM: Artificial Sequence
<220> FEATURE:
<223> OTHER INFORMATION: MK17 VH CDR3

<400> SEQUENCE: 36

Cys Ala Arg Asp Arg Gly Tyr Pro Trp Leu Arg Ser Arg Gly Gly Met
1               5                   10                  15

Asp Val

<210> SEQ ID NO 37
<211> LENGTH: 8
<212> TYPE: PRT
<213> ORGANISM: Artificial Sequence
<220> FEATURE:
<223> OTHER INFORMATION: LA25 VH CDR1

<400> SEQUENCE: 37

Gly Phe Thr Phe Ser Ser Tyr Gly
1               5

<210> SEQ ID NO 38
<211> LENGTH: 8
<212> TYPE: PRT
<213> ORGANISM: Artificial Sequence
<220> FEATURE:
<223> OTHER INFORMATION: LA25 VH CDR2

<400> SEQUENCE: 38

Ile Trp Tyr Asp Gly Ser Asn Lys
1               5

<210> SEQ ID NO 39
<211> LENGTH: 13
<212> TYPE: PRT
<213> ORGANISM: Artificial Sequence
<220> FEATURE:
<223> OTHER INFORMATION: LA25 VH CDR3

<400> SEQUENCE: 39

Cys Ala Arg Gly Arg Trp Gly Gly Tyr Phe Asp Leu Trp
1               5                   10

<210> SEQ ID NO 40
<211> LENGTH: 11
<212> TYPE: PRT
<213> ORGANISM: Artificial Sequence
```

```
<220> FEATURE:
<223> OTHER INFORMATION: KA2 VL CDR1

<400> SEQUENCE: 40

Gln Ser Leu Leu His Ser Asn Gly Tyr Asn Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: KA2 VL CDR2

<400> SEQUENCE: 41

Leu Gly Ser
1

<210> SEQ ID NO 42
<211> LENGTH: 10
<212> TYPE: PRT
<213> ORGANISM: Artificial Sequence
<220> FEATURE:
<223> OTHER INFORMATION: KA2 VL CDR3

<400> SEQUENCE: 42

Cys Met Gln Ala Leu Gln Thr His Ser Phe
1               5                   10

<210> SEQ ID NO 43
<211> LENGTH: 11
<212> TYPE: PRT
<213> ORGANISM: Artificial Sequence
<220> FEATURE:
<223> OTHER INFORMATION: LRO4 VL CDR1

<400> SEQUENCE: 43

Lys Ser Leu Leu His Ser Asn Gly Asn Thr Tyr
1               5                   10

<210> SEQ ID NO 44
<211> LENGTH: 3
<212> TYPE: PRT
<213> ORGANISM: Artificial Sequence
<220> FEATURE:
<223> OTHER INFORMATION: LRO4 VL CDR2

<400> SEQUENCE: 44

Arg Met Ser
1

<210> SEQ ID NO 45
<211> LENGTH: 11
<212> TYPE: PRT
<213> ORGANISM: Artificial Sequence
<220> FEATURE:
<223> OTHER INFORMATION: LRO4 VL CDR3

<400> SEQUENCE: 45

Cys Met Gln His Leu Glu Tyr Pro Tyr Thr Phe
1               5                   10

<210> SEQ ID NO 46
<211> LENGTH: 8
<212> TYPE: PRT
<213> ORGANISM: Artificial Sequence
<220> FEATURE:
```

```
<223> OTHER INFORMATION: ML7 VL CDR1

<400> SEQUENCE: 46

Ser Ser Asn Ile Gly Ser Asn Tyr
1               5

<210> SEQ ID NO 47
<211> LENGTH: 3
<212> TYPE: PRT
<213> ORGANISM: Artificial Sequence
<220> FEATURE:
<223> OTHER INFORMATION: ML7 VL CDR2

<400> SEQUENCE: 47

Ser Asn Asn
1

<210> SEQ ID NO 48
<211> LENGTH: 13
<212> TYPE: PRT
<213> ORGANISM: Artificial Sequence
<220> FEATURE:
<223> OTHER INFORMATION: MK7 VL CDR3

<400> SEQUENCE: 48

Cys Ala Ala Trp Asp Val Ser Leu Arg Gln Trp Leu Phe
1               5                   10

<210> SEQ ID NO 49
<211> LENGTH: 6
<212> TYPE: PRT
<213> ORGANISM: Artificial Sequence
<220> FEATURE:
<223> OTHER INFORMATION: MK17 VL CDR1

<400> SEQUENCE: 49

Gln Gly Ile Gly Asn Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: MK17 VL CDR2

<400> SEQUENCE: 50

Ala Ala Ser
1

<210> SEQ ID NO 51
<211> LENGTH: 11
<212> TYPE: PRT
<213> ORGANISM: Artificial Sequence
<220> FEATURE:
<223> OTHER INFORMATION: MK17 VL CDR3

<400> SEQUENCE: 51

Cys Gln Gln Leu Asn Gly Tyr Pro Leu Thr Phe
1               5                   10

<210> SEQ ID NO 52
<211> LENGTH: 9
<212> TYPE: PRT
<213> ORGANISM: Artificial Sequence
<220> FEATURE:
<223> OTHER INFORMATION: LA25 VL CDR1
```

```
<400> SEQUENCE: 52

Ser Ser Asp Val Gly Gly Tyr Asn Tyr
1               5

<210> SEQ ID NO 53
<211> LENGTH: 3
<212> TYPE: PRT
<213> ORGANISM: Artificial Sequence
<220> FEATURE:
<223> OTHER INFORMATION: LA25 VL CDR2

<400> SEQUENCE: 53

Glu Val Ser
1

<210> SEQ ID NO 54
<211> LENGTH: 12
<212> TYPE: PRT
<213> ORGANISM: Artificial Sequence
<220> FEATURE:
<223> OTHER INFORMATION: LA25 VL CDR3

<400> SEQUENCE: 54

Cys Ser Ser Tyr Ala Gly Ser Asn Asn Tyr Trp Val
1               5                   10
```